United States Patent [19]

Thøgersen et al.

[11] Patent Number: 5,917,018

[45] Date of Patent: Jun. 29, 1999

[54] ITERATIVE METHOD OF AT LEAST FIVE CYCLES FOR THE REFOLDING OF PROTEINS

[75] Inventors: Christian Thøgersen, Mundelstrup; Thor Las Holtet, Aarhus V; Michael Etzerodt, Hinnerup, all of Denmark

[73] Assignee: Denzyme APS, Aarhus C, Denmark

[21] Appl. No.: 08/469,658

[22] Filed: Sep. 18, 1995

Related U.S. Application Data

[62] Division of application No. 08/102,060, Feb. 4, 1994, abandoned, filed as application No. PCT/GB98/02492, Dec. 3, 1993.

[30] Foreign Application Priority Data

Feb. 4, 1993 [DK] Denmark ................................. 130/93
Feb. 5, 1993 [DK] Denmark ................................. 139/93

[51] Int. Cl.$^6$ .......................... C07K 14/00; C07K 14/47; C07K 14/745; C12P 21/00
[52] U.S. Cl. .......................... 530/350; 530/402; 530/412; 530/427; 530/384; 435/183
[58] Field of Search .................................. 530/350, 402, 530/412, 417, 427, 408, 409, 300, 384; 435/183

[56] References Cited

U.S. PATENT DOCUMENTS

| | | | |
|---|---|---|---|
| 4,444,878 | 4/1984 | Paulus ....................................... | 435/7.5 |
| 4,656,255 | 4/1987 | Seely ....................................... | 530/417 |
| 4,977,248 | 12/1990 | Creigton ................................. | 530/412 |
| 4,999,422 | 3/1991 | Galliher ................................ | 530/351 |
| 5,074,977 | 12/1991 | Cheung et al. ......................... | 435/7.1 |
| 5,077,392 | 12/1991 | Rudolph et al. ........................ | 530/402 |
| 5,231,168 | 7/1993 | Dziegel et al. ......................... | 530/350 |
| 5,284,933 | 2/1994 | Dobeli et al. ........................... | 530/413 |
| 5,324,436 | 6/1994 | John et al. ............................... | 210/638 |

FOREIGN PATENT DOCUMENTS

| | | |
|---|---|---|
| 0 035 384 A2 | 9/1981 | European Pat. Off. . |
| 0 161 937 A2 | 12/1985 | European Pat. Off. . |
| 0 432 419 A1 | 9/1991 | European Pat. Off. . |
| 2138004 | 10/1984 | United Kingdom . |
| 86/05809 | 9/1986 | WIPO . |
| 94/18227 | 8/1994 | WIPO . |

OTHER PUBLICATIONS

Buchner, J., et al., "Renaturation, Purification and Characterization of Recombinant F$^{ab}$ –Fragments Produced in Escherichica Coli", 1991, *Biotechnology*, vol. 9, pp. 157–162.

Dalbooge, H., et al., "A Novel Enzymatic Method For Production of Authentic hGH From an Escherichia Coli Produced HGH–Procursor", 1987, *Bio/Technology*, vol. 5, pp. 161–164.

Fung, M., et al., "Blood Coagulation Factor X mRNA Encodes a Single Polypeptide Chain Containing a Prepro Leader Sequence", 1984, *Nucleic Acids Research*, vol. 12, pp. 4481–4492.

Jaenicke, R., et al., MRC Lab. of Molec. Biol., Cambridge, UK, "Folding Proteins", 1989, *Protein Structure, A Practical Approach*, IRL Press, pp. 191–223.

Nagai, K., et al., "Synthesis and Sequence–Specific Proteolysis of Hybrid Proteins Produced in Escherichia Coli", 1987, *Methods in Enzymology*, vol. 153, pp. 461–481.

Schein, C., "Solubility as a Function of Protein Structure and Solvent Components", 1990 *Bio/Technology*, vol. 8, pp. 308–317.

Holtet, T.H. et al., FEBS Letters, vol. 344, No. 2,3 May 16, 1994, pp. 242–246.

Zhang et al., "Reconstitution of the Diiron Sites in Hemerythuin & Myohemerythrin", *Biochem.* 30:583–589, 1991.

Katagiri et al., "Bovine endothelial cell plasminogen activator inhibitor", *Eur. J. Biochem.* 176:81–87. 1988.

Holliger et al., "Diabodies: Small bivalent and bispecific antibody fragments", *PNAS* 90:6444–6448, 1993.

Messier et al., "Cloning and Expression in COS–1 cells of a full–length CDNA encoding human coagulation factor X", *GENE* 99:291–294, 1991.

Morita et al., "Localization of the Structural Difference between Bovine Blood Coagulation Factors $X_1$ and $X_2$" *J. Biol. Chem.* 261(9):4008–4014, 1986.

Kaul et al., "Isolation and characterization of human factor X CDNA", *GENE* 41:311–314, 1986.

Hoffman et al., "Purification of his–tagged proteins . . .", *Nuc, Acids. Res.* 19(22):6337–6338, 1991.

Brey et al., "Dielectric Measurements of Water Sorbed on Ovalbumin and Lysozyme", *J. Coll. Interface Sci.* 30(1):13–20, 1969.

Mozhaev et al., *Chem Abst.* 91:248, abs#119, 502j, 1979.

*Primary Examiner*—Stephen Walsh
*Assistant Examiner*—Claire M. Kaufman
*Attorney, Agent, or Firm*—Fish & Richardson P.C.

[57] ABSTRACT

A novel, generally applicable method for producing correctly folded proteins from a mixture of misfolded proteins, e.g. bacterial inclusion-body aggregates. A major new aspect of the method is that over-all efficiency is achieved by subjecting proteins to a time-sequence of multiple denaturation-renaturation cycles, resulting in gradual accumulation of the correctly folded protein. The method has proven efficient for a variety of recombinant proteins. Also provided are novel encrypted recognition sites for bovine coagulation factor $X_a$. The encrypted recognition sites described may be activated in vitro by controlled oxidation or by reversible derivatization of cysteine residues and thereby generate new cleavage sites for factor $X_a$. Two new recombinant serine protease exhibiting narrow substrate specificity for factor $X_a$ recognition sites are also provided. They may replace natural coagulation factor $X_a$ for cleavage of chimeric proteins.

24 Claims, 28 Drawing Sheets

Human β2-microglobulin:

```
     -20                 -10                  -1 1                   10
      M S R S V A L A V L A L L S L S G L E A I Q R T P K I Q V Y
                        20                   30                   40
      S R H P A E N G K S N F L N C Y V S G F H P S D I E V D L L
                        50                   60                   70
      K N G E R I E K V E H S D L S F S K D W S F Y L L Y Y T E F
                        80                   90
      T P T E K D E Y A C R V N H V T L S Q P K I V K W D R D M
                                                          SEQ ID NO: 49
```

Fig. 3a

Murine β2-microglobulin:

```
     -20                 -10                  -1 1                   10
      M A R S V T L V F L V L V S L T G L Y A I Q K T P Q I Q V Y
                        20                   30                   40
      S R H P P E N G K P N I L N C Y V T Q F H P P H I E I Q M L
                        50                   60                   70
      K N G K K I P K V E M S D M S F S K D W S F Y I L A H T E F
                        80                   90
      T P T E T D T Y A C R V K H D S M A E P K T V Y W D R D M
                                                          SEQ ID NO: 50
```

Fig. 3b

Human Growth Hormone (Somatotropin).

```
      -26                                                      -11   -4
        M A T G S R T S L L L A F G L L C L P W L Q E G S A F P T I
                          10                      20                    30
        P L S R L F D N A S L R A H R L H Q L A F D T Y Q E F E E A
              40                      50                      60
        Y I P K E Q K Y S F L Q N P Q T S L C F S E S I P T P S N R
                    70                      80                      90
        E E T Q Q K S N L E L L R I S L L L I Q S W L E P V Q F L R
                100                     110                     120
        S V F A N S L V Y G A S D S N V Y D L L K D L E E G I Q T L
              130                     140                     150
        M G R L E D G S P R T G Q I F K Q T Y S K F D T N S H N D D
                    160                     170                     180
        A L L K N Y G L L Y C F R K D M D K V E T F L R I V Q C R S
              190
        V E G S C G F
```

SEQ ID NO: 51

```
        G S I E G R A I              C R *
#1      GATCCATCGAGGGTAGGCTATC ----- TGCCGATA

G S I E G R A I              K A *
#2      GATCCATCGAGGGTAGGCTATC ----- AAGGCCTA

G S I E G R A I              K K *
#3      GATCCATCGAGGGTAGGCTATC ----- AAGAAGTA
```

```
       M G S H H H H H H
       CATATGGGATCGCATCACCATCACCATCACG ----- AGCTTGAATTC
                                         BamHI   HindIII
```

SEQ ID NO: 52
SEQ ID NO: 38

α₂MR:

```
           G  S  I  E  G  R  G  T           L  D  *
    #4    GATCCATCGAGGGTAGGGCACC ----- CTGGACTA
```

SEQ ID NO: 52
SEQ ID NO: 38

```
           G  S  I  E  G  R  V  P           D  Q  *
    #5    GATCCATCGAGGGTAGGGTGCCT ----- GACCAGTA
```

```
           G  S  I  E  G  R  G  G  Q  C        F  K  *
    #6    GATCAATCGAGGGTAGGGGTGGTCAGTGC ---- TTTAAGTA
```

```
G  K  G  S  H  H  H  H  H  H
GGGAAGGGATCGCATCACCATCACCATCACG ----- AGCTTGGCGTA
                                      BamHI  HindIII
```

α2-Macroglobulin Receptor.  SEQ ID NO: 52

```
                           20
  1 MLTPPLLLLLPLLSALVAAAIDAPKTCSPKQFACRDQITCISKGWRCDGERDCPDGSDEA
                                                           109
 61 PEICPQSKAQRCQPNEHNCLGTELCVPMSRLCNGVQDCMDGSDEGPHCRELQGNCSRLGC
121 QHHCVPTLDGPTCYCNSSFQLQADGKTCKDFDECSVYGTCSQLCTNTDGSFICGCVEGYL
                          190
181 LQPDNRSCKAKNEPVDRPPVLLIANSQNILATYLSGAQVSTITPTSTRQTTAMDFSYANE
241 TVCWVHVGDSAAQTQLKCARMPGLKGFVDEHTINISLSLHHVEQMAIDWLTGNFYFVDDI
301 DDRIFVCNRNGDTCVTLLDLELYNPKGIALDPAMGKVFFTDYGQIPKVERCDMDGQNRTK
361 LVDSKIVFPHGITLDLVSRLVYWADAYLDYIEVVDYEGKGRQTIIQGILIEHLYGLTVFE
421 NYLYATNSDNANAQQKTSVIRVNRFNSTEYQVVTRVDKGGALHIYHQRRQPRVRSHACEN
                                          521
481 DQYGKPGGCSDICLLANSHKARTCRCRSGFSLGSDGKSCKKPEHELFLVYGKGRPGIIRG
541 MDMGAKVPDEHMIPIENLMNPRALDFHAETGFIYFADTTSYLIGRQKIDGTERETILKDG
601 IHNVEGVAVDWMGDNLYWTDDGPKKTISVARLEKAAQTRKTLIEGKMTHPRAIVVDPLNG
661 WMYWTDWEEDPKDSRRGRLERAWMDGSHRDIFVTSKTVLWPNGLSLDIPAGRLYVVDAFY
721 DRIETILLNGTDRKIVYEGPELNHAFGLCHHGNYLFWTEYRSGSVYRLERGVGGAPPTVT
                             803
781 LLRSERPPIFEIRMYDAQQQQVGTNKCRVNNGGCSSLCLATPGSRQCACAEDQVLDADGV
841 TCLANPSYVPPPQCQPGEFACANSRCIQERWKCDGDNDCLDNSDEAPALCHQHTCPSDRF
901 KCENNRCIPNRWLCDGDNDCGNSEDESNATCSARTCPPNQFSCASGRCIPISWTCDLDDD
961 CGDRSDESASCAYPTCFPLTQFTCNNGRCININWRCDNDNDCGDNSDEAGCSHSCSSTQF
1021 KCNSGRCIPEHWTCDGDNDCGDYSDETHANCTNQATRPPGGCHTDEFQCRLDGLCIPLRW
1081 RCDGDTDCMDSSDEKSCEGVTHVCDPSVKFGCKDSARCISKAWVCDGDNDCEDNSDEENC
                                                          1184
1141 ESLACRPPSHPCANNTSVCLPPDKLCDGNDDCGDGSDEGELCDQCSLNNGGCSHNCSVAP
1201 GEGIVCSCPLGMELGPDNHTCQIQSYCAKHLKCSQKCDQNKFSVKCSCYEGWVLEPDGES
     1265
1261 CRSLDPFKPFIIFSNRHEIRRIDLHKGDYSVLVPGLRNTIALDFHLSQSALYWTDVVEDK
1321 IYRGKLLDNGALTSFEVVIQYGLATPEGLAVDWIAGNIYWVESNLDQIEVAKLDGTLRTT
1381 LLAGDIEHPRAIALDPRDGILFWTDWDASLPRIEAASMSGAGRRTVHRETGSGGWPNGLT
1441 VDYLEKRILWIDARSDAIYSARYDGSGHMEVLRGHEFLSHPFAVTLYGGEVYWTDWRTNT
1501 LAKANKWTGHNVTVVQRTNTQPFDLQVYHPSRQPMAPNPCEANGGQGPCSHLCLINYNRT
     1582
1561 VSCACPHLMKLHKDNTTCYEFKKFLLYARQMEIRGVDLDAPYYNYIISFTVPDIDNVTVL
1621 DYDAREQRVYWSDVRTQAIKRAFINGTGVETVVSADLPNAHGLAVDWVSRNLFWTSYDTN
1681 KKQINVARLDGSFKNAVVQGLEQPHGLVVHPLRGKLYWTDGDNISMANMDGSNRTLLFSG
1741 QKGPVGLAIDFPESKLYWISSGNHTINRCNLDGSGLEVIDAMRSQLGKATALAIMGDKLW
1801 WADQVSEKMGTCSKADGSGSVVLRNSTTLVMHMKVYDESIQLDHKGTNPCSVNNGDCSQL
1861 CLPTSETTRSCMCTAGYSLRSGQQACEGVGSFLLYSVHEGIRGIPLDPNDKSDALVPVSG
1921 TSLAVGIDFHAENDTIYWVDMGLSTISRAKRDQTWREDVVTNGIGRVEGIAVDWIAGNIY
1981 WTDQGFDVIEVARLNGSFRYVVISQGLDKPRAITVHPEKGYLFWTEWGQYPRIERSRLDG
2041 TERVVLVNVSISWPNGISVDYQDGKLYWCDARTDKIERIDLETGENREVVLSSNNMDMFS
2101 VSVFEDFIYWSDRTHANGSIKRGSKDNATDSVPLRTGIGVQLKDIKVFNRDRQKGTNVCA
2161 VANGGCQQLCLYRGRGQRACACAHGMLAEDGASCREYAGYLLYSERTILKSIHLSDERNL
2221 NAPVQPFEDPEHMKNVIALAFDYRAGTSPGTPNRIFFSDIHFGNIQQINDDGSRRITIVE
2281 NVGSVEGLAYHRGWDTLYWTSYTTSTITRHTVDQTRPGAFERETVITMSGDDHPRAFVLD
2341 ECQNLMFWTNWNEQHPSIMRAALSGANVLTLIEKDIRTPNGLAIDHRAEKLYFSDATLDK
2401 IERCEYDGSHRYVILKSEPVHPFGLAVYGEHIFWTDWVRRAVQRANKHVGSNMKLLRVDI
                                                           2520
2461 PQQPMGIIAVANDTNSCELSPCRINNGGCQDLCLLTHQGHVNCSCRGGRILQDDLTCRAV
2521 NSSCRAQDEFECANGECINFSLTCDGVPHCKDKSDEKPSYCNSRRCKKTFRQCSNGRCVS
2581 NMLWCNGADDCGDGSDEIPCNKTACGVGEFRCRDGTCIGNSSRCNQFVDCEDASDEMNCS
2641 ATDCSSYFRLGVKGVLFQPCERTSLCYAPSWVCDGANDCGDYSDERDCPGVKRPRCPLNY
2701 FACPSGRCIPMSWTCDKEDDCEHGEDETHCNKFCSEAQFECQNHRCISKQWLCDGSDDCG
```

Fig. 9a

```
2761 DGSDEAAHCEGKTCGPSSFSCPGTHVCVPERWLCDGDKDCADGADESIAAGCLYNSTCDD
2821 REFMCQNRQCIPKHFVCDHDRDCADGSDESPECEYPTCGPSEFRCANGRCLSSRQWECDG
2881 ENDCHDQSDEAPKNPHCTSPEHKCNASSQFLCSSGRCVAEALLCNGQDDCGDSSDERGCH
     2941
2941 INECLSRKLSGCSQDCEDLKIGFKCRCRPGFRLKDDGRTCADVDECSTTFPCSQRCINTH
3001 GSYKCLCVEGYAPRGGDPHSCKAVTDEEPFLIFANRYYLRKLNLDGSNYTLLKQGLNNAV
3061 ALDFDYREQMIYWTDVTTQGSMIRRMHLNGSNVQVLHRTGLSNPDGLAVDWVGGNLYWCD
3121 KGRDTIEVSKLNGAYRTVLVSSGLREPRALVDVQNGYLYWTDWGDHSLIGRIGMDGSSR
3181 SVIVDTKITWPNGLTLDYVTERIYWADAREDYIEFASLDGSNRHVVLSQDIPHIFALTLF
3241 EDYVYWTDWETKSINRAHKTTGTNKTLLISTLHRPMDLHVFHALRQPDVPNHPCKVNNGG
     3331
3301 CSNLCLLSPGGGHKCACPTNFYLGSDGRTCVSNCTASQFVCKNDKCIPFWWKCDTEDDCG
3361 DHSDEPPDCPEFKCRPGQFQCSTGICTNPAFICDGDNDCQDNSDEANCDIHVCLPSQFKC
3421 TNTNRCIPGIFRCNGQDNCGDGEDERDCPEVTCAPNQFQCSITKRCIPRVWVCDRDNDCV
3481 DGSDEPANCTQMTCGVDEFRCKDSGRCIPARWKCDGEDDCGDGSDEPKEECDERTCEPYQ
3541 FRCKNNRCVPGRWQCDYDNDCGDNSDEESCTPRPCSESEFSCANGRCIAGRWKCDGDHDC
3601 ADGSDEKDCTPRCDMDQFQCKSGHCIPLRWRCDADADCMDGSDEEACGTVRTCPLDEFQ
3661 CNNTLCKPLAWKCDGEDDCGDNSDENPEECARFVCPPNRPFRCKNDRVCLWIGRQCDGTD
                                                         3778
3721 NCGDGTDEEDCEPPTAHTTHCKDKKEFLCRNQRCLSSLRCNMFDDCGDGSDEEDCSIDP
3781 KLTSCATNASICGDEARCVRTEKAAYCACRSGFHTVPGQPGCQDINECLRFGTCSQLCNN
3841 TKGGHLCSCARNFMKTHNTCKAEGSEYQVLYIADDNEIRSLFPGHPHSAYEQAFQGDESV
3901 RIDAMDVHVKAGRVYWTNWHTGTISYRSLPPAAPPTTSNRHRRQIDRGVTHLNISGLKMP
3961 RGIAIDWVAGNVYWTDSGRDVIEVAQMKGENRKTLISGMIDEPHAIVVDPLRGTMYWSDW
4021 GNHPKIETAAMDGTLRETLVQDNIQWPTGLAVDYHNERLYWADAKLSVIGSIRLNGTDPI
4081 VAADSKRGLSHPFSIDVFEDYIYGVTYINNRVFKIHKFGHSPLVNLTGGLSHASDVVLYH
4141 QHKQPEVTNPCDRKKCEWLCLLSPSGPVCTCPNGKRLDNGTCVPVPSPTPPDAPRPGTC
4201 NLQCFNGGSCFLNARRQPKCRCQPRYTGDKCELDQCWEHCRNGGTCAASPSGMPTCRCPT
4261 GFTGPKCTQQVCAGYCANNSTCTVNQGNQPQCRCLPGFLGDRCQYRQCSGYCENFGTCQM
4321 AADGSRQCRCTAYFEGSRCEVNKCSRCLEGACVVNKQSGDVTCNCTDGRVAPSCLTCVGH
4381 CSNGGSCTMNSKMMPECQCPPHMTGPRCEEHVFSQQQPGHIASILIPLLLLIVLVAGV
4441 VFWYKRRVQGAKGFQHQRMTNGAMNVEIGNPTYKMYEGGEPDDVGLLDADFALDPDKPT
4501 NFTNPVYATLYMGGHGSRHSLASTDEKRELLGRGPEDEIGDPLA

SEQ ID NO: 52
```

Fig. 9b

Bovine FX.

```
  1 M A G L L L H L V L L S T A L G G L L R P A G S V F L P R D Q
 31 A H R V L Q R A R R A N S F L E E V K Q G N L E R E C L E E
                                        82
 61 A C S L E E A R E V F E D A E Q T D E F W S K Y K D G D Q C
 91 E G H P C L N Q G H C K D G I G D Y T C T C A E G F E G K N
121 C E F S T R E I C S L D N G G C D Q F C R E E R S E V R C S
151 C A H G Y V L G D D S K S C V S T E R F P C G K F T Q G R S
181 R R W A I H T S E D A L D A S E L E H Y D P A D L S P T E S
211 S L D L L G L N R T E P S A G E D G S Q V V R I V G G R D C
241 A E G E C P W Q A L L V N E E N E G F C G G T I L N E F Y V
271 L T A A H C L H Q A K R F T V R V G D R N T E Q E E G N E M
301 A H E V E M T V K H S R E V K E T Y D E D I A V L R L K T P
331 I R F R R N V A P A C L P E K D W A E A T L M T Q K T G I V
361 S G F G R T H E K G R L S S T L K M L E V P Y V D R S T C K
391 L S S S F T I T P N M F C A G Y D T Q P E D A C Q G D S G G
421 P H V T R E K D T Y F V T G I V S W G E G C A R K G K F G V
451 Y T K V S N F L K W I D K I M K A R A G A A G S R G H S E A
                              484
481 P A T W T V P
```

Fig. 11                                    SEQ ID NO: 53

Fig. 14

Glu - Plasminogen.

SEQ ID NO: 54

Human α₂MRBDv.

(1299) V Y L Q T S L K Y N I L P E K E E F P F A L G V Q T L P Q T
C D E P K A H T S F Q I S L S V S Y T G S R S A S N M A I V
D V K M V S G F I P L K P T V K M L E R S N H V S R T E V S
S N H V L I Y L D K V S N Q T L S L F F T V L Q D V P V R D
L K P A I V K V V Y D Y Y E T D E F A I A E Y N A P C S K D L
153
G N A(1451)

SEQ ID NO: 55

Fig. 19

Human Tetranectin.

```
-21                                              -1 1
    M E L W G A Y L L L C L F S L L T Q V T T E P P T Q K P K K
          10              20              30
        I V N A K K D V V N T K M F E E L K S R L D T L A Q E V A L
     40              50              60
    L K E Q Q A L Q T V C L K G T K V H M K C F L A F T Q T K T
     70              80              90
    F H E A S E D C I S R G G T L S T P Q T G S E N D A L Y E Y
     100             110             120
    L R Q S V G N E A E I W L G L N D M A A E G T W V D M T G A
     130             140             150
    R I A Y K N W E T E I T A Q P D G G K T E N C A V L S G A A
     160             170             180
    N G K W F D K R C R D Q L P Y I C Q F G I V
```

SEQ ID NO: 56

```
  1 QVKLQQSGAELVKPGASVKMSCKASGYTFA
 31 SYWINWVKQRPGQGLEWIGHIYPVRSITKY
 61 NEKFKSKATLTLDTSSTAYMQLSSLTSED
 91 SAVYYCSRGDGSDYYAMDYWGQGTTVTVSS
121 GGGSSVSMHWYQQKPGSSPKPWIYATSNLAS
151 SSSSYMHWYQQKPGSSPKPWIYATSNLAS
181 GVPTRFSGSGTGSYSLTISRVEAEDAATY
211 YCQQWSRNPFTFGSGTKLEIKRAAAEQKLI
241 SEEDLN
```

SEQ ID NO: 57

Fig. 23

Human Psoriasin.

```
  1                   10                    20                    30
  M S N T Q A E R S I  I G M I D M F H K Y  T R R D D K I D K P
                        40                    50                    60
  S L L T M M K E N F  P N F L S A C D K K  G T N Y L A D V F E
                        70                    80                    90
  K K D K N E D K K I  D F S E F L S L L G  D I A T T D Y H K Q S
                       100
  H G A A P C S G G S  Q
```

SEQ ID NO: 58

Fig. 25

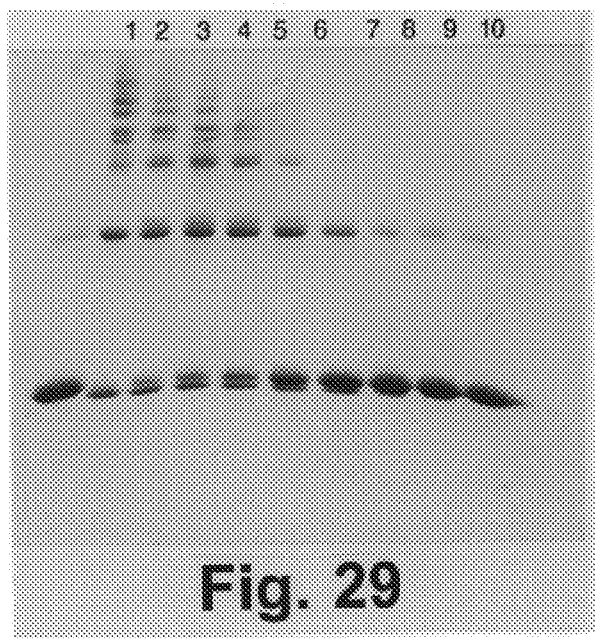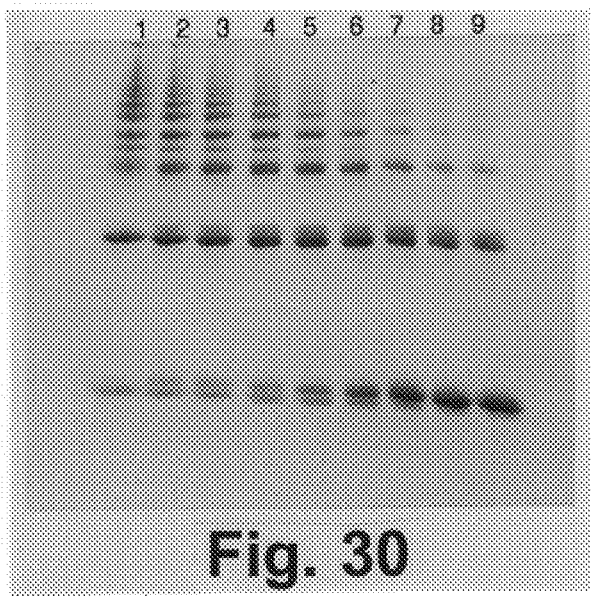

SEQUENCE LISTING (1) GENERAL INFORMATION:

(iii) NUMBER OF SEQUENCES: 58

(2) INFORMATION FOR SEQ ID NO: 1:

(i) SEQUENCE CHARACTERISTICS:
        (A) LENGTH: 1554 base pairs
        (B) TYPE: nucleic acid
        (C) STRANDEDNESS: double
        (D) TOPOLOGY: linear (ii) MOLECULE TYPE: cDNA (iii) HYPOTHETICAL: YES (iii) ANTI-SENSE: NO (vi) ORIGINAL SOURCE:
        (A) ORGANISM: Bos taurus (ix) FEATURE:
        (A) NAME/KEY: CDS
        (B) LOCATION: 76..1551

(xi) SEQUENCE DESCRIPTION: SEQ ID NO: 1:

```
AGCCTGGGCG AGCGGACCTT GCCCTGGAGG CCTGTTGCGG CAGGGACTCA CGGCTGTCCT           60

CGGAAGGGCC CCACC ATG GCG GGC CTG CTG CAT CTC GTT CTG CTC AGC ACC          111
                Met Ala Gly Leu Leu His Leu Val Leu Leu Ser Thr
                  1               5                          10

GCC CTG GGC GGC CTC CTG CGG CCG GCG GGG AGC GTG TTC CTG CCC CGG           159
Ala Leu Gly Gly Leu Leu Arg Pro Ala Gly Ser Val Phe Leu Pro Arg
             15                  20                  25

GAC CAG GCC CAC CGT GTC CTG CAG AGA GCC CGC AGG GCC AAC TCA TTC           207
Asp Gln Ala His Arg Val Leu Gln Arg Ala Arg Arg Ala Asn Ser Phe
         30                  35                  40

TTG GAG GAG GTG AAG CAG GGA AAC CTG GAG CGA GAG TGC CTG GAG GAG           255
Leu Glu Glu Val Lys Gln Gly Asn Leu Glu Arg Glu Cys Leu Glu Glu
     45                  50                  55                  60

GCC TGC TCA CTA GAG GAG GCC CGC GAG GTC TTC GAG GAC GCA GAG CAG           303
Ala Cys Ser Leu Glu Glu Ala Arg Glu Val Phe Glu Asp Ala Glu Gln
                 65                  70                  75

ACG GAT GAA TTC TGG AGT AAA TAC AAA GAT GGA GAC CAG TGT GAA GGC           351
Thr Asp Glu Phe Trp Ser Lys Tyr Lys Asp Gly Asp Gln Cys Glu Gly
                     80                  85                  90

CAC CCG TGC CTG AAT CAG GGC CAC TGT AAA GAC GGC ATC GGA GAC TAC           399
His Pro Cys Leu Asn Gln Gly His Cys Lys Asp Gly Ile Gly Asp Tyr
                 95                 100                 105
```

```
ACC TGC ACC TGT GCG GAA GGG TTT GAA GGC AAA AAC TGC GAG TTC TCC       447
Thr Cys Thr Cys Ala Glu Gly Phe Glu Gly Lys Asn Cys Glu Phe Ser
        110                 115                 120

ACG CGT GAG ATC TGC AGC CTG GAC AAT GGA GGC TGC GAC CAG TTC TGC       495
Thr Arg Glu Ile Cys Ser Leu Asp Asn Gly Gly Cys Asp Gln Phe Cys
125                 130                 135                 140

AGG GAG GAG CGC AGC GAG GTG CGG TGC TCC TGC GCG CAC GGC TAC GTG       543
Arg Glu Glu Arg Ser Glu Val Arg Cys Ser Cys Ala His Gly Tyr Val
                145                 150                 155

CTG GGC GAC GAC AGC AAG TCC TGC GTG TCC ACA GAG CGC TTC CCC TGT       591
Leu Gly Asp Asp Ser Lys Ser Cys Val Ser Thr Glu Arg Phe Pro Cys
            160                 165                 170

GGG AAG TTC ACG CAG GGA CGC AGC CGG CGG TGG GCC ATC CAC ACC AGC       639
Gly Lys Phe Thr Gln Gly Arg Ser Arg Arg Trp Ala Ile His Thr Ser
        175                 180                 185

GAG GAC GCG CTT GAC GCC AGC GAG CTG GAG CAC TAC GAC CCT GCA GAC       687
Glu Asp Ala Leu Asp Ala Ser Glu Leu Glu His Tyr Asp Pro Ala Asp
190                 195                 200

CTG AGC CCC ACA GAG AGC TCC TTG GAC CTG CTG GGC CTC AAC AGG ACC       735
Leu Ser Pro Thr Glu Ser Ser Leu Asp Leu Leu Gly Leu Asn Arg Thr
205                 210                 215                 220

GAG CCC AGC GCC GGG GAG GAC GGC AGC CAG GTG GTC CGG ATA GTG GGC       783
Glu Pro Ser Ala Gly Glu Asp Gly Ser Gln Val Val Arg Ile Val Gly
                225                 230                 235

GGC AGG GAC TGC GCG GAG GGC GAG TGC CCA TGG CAG GCT CTG CTG GTC       831
Gly Arg Asp Cys Ala Glu Gly Glu Cys Pro Trp Gln Ala Leu Leu Val
            240                 245                 250

AAC GAA GAG AAC GAG GGA TTC TGC GGG GGC ACC ATC CTG AAC GAG TTC       879
Asn Glu Glu Asn Glu Gly Phe Cys Gly Gly Thr Ile Leu Asn Glu Phe
        255                 260                 265

TAC GTC CTC ACG GCT GCC CAC TGC CTG CAC CAG GCC AAG AGG TTC ACG       927
Tyr Val Leu Thr Ala Ala His Cys Leu His Gln Ala Lys Arg Phe Thr
270                 275                 280

GTG AGG GTC GGC GAC CGG AAC ACA GAG CAG GAG GAG GGC AAC GAG ATG       975
Val Arg Val Gly Asp Arg Asn Thr Glu Gln Glu Glu Gly Asn Glu Met
285                 290                 295                 300

GCA CAC GAG GTG GAG ATG ACT GTG AAG CAC AGC CGC TTT GTC AAG GAG      1023
Ala His Glu Val Glu Met Thr Val Lys His Ser Arg Phe Val Lys Glu
                305                 310                 315

ACC TAC GAC TTC GAC ATC GCG GTG CTG AGG CTC AAG ACG CCC ATC CGG      1071
Thr Tyr Asp Phe Asp Ile Ala Val Leu Arg Leu Lys Thr Pro Ile Arg
            320                 325                 330

TTC CGC CGG AAC GTG GCG CCC GCC TGC CTG CCC GAG AAG GAC TGG GCG      1119
Phe Arg Arg Asn Val Ala Pro Ala Cys Leu Pro Glu Lys Asp Trp Ala
        335                 340                 345

GAG GCC ACG CTG ATG ACC CAG AAG ACG GGC ATC GTC AGC GGC TTC GGG      1167
Glu Ala Thr Leu Met Thr Gln Lys Thr Gly Ile Val Ser Gly Phe Gly
350                 355                 360

CGC ACG CAC GAG AAG GGC CGC CTG TCG TCC ACG CTC AAG ATG CTG GAG      1215
Arg Thr His Glu Lys Gly Arg Leu Ser Ser Thr Leu Lys Met Leu Glu
365                 370                 375                 380

GTG CCC TAC GTG GAC CGC AGC ACC TGT AAG CTG TCC AGC AGC TTC ACC      1263
Val Pro Tyr Val Asp Arg Ser Thr Cys Lys Leu Ser Ser Ser Phe Thr
                385                 390                 395

ATT ACG CCC AAC ATG TTC TGC GCC GGC TAC GAC ACC CAG CCC GAG GAC      1311
Ile Thr Pro Asn Met Phe Cys Ala Gly Tyr Asp Thr Gln Pro Glu Asp
            400                 405                 410

GCC TGC CAG GGC GAC AGT GGC GGC CCC CAC GTC ACC CGC TTC AAG GAC      1359
Ala Cys Gln Gly Asp Ser Gly Gly Pro His Val Thr Arg Phe Lys Asp
        415                 420                 425
```

```
ACC TAC TTC GTC ACA GGC ATC GTC AGC TGG GGA GAA GGG TGC GCG CGC      1407
Thr Tyr Phe Val Thr Gly Ile Val Ser Trp Gly Glu Gly Cys Ala Arg
    430                 435                 440

AAG GGC AAG TTC GGC GTC TAC ACC AAG GTC TCC AAC TTC CTC AAG TGG      1455
Lys Gly Lys Phe Gly Val Tyr Thr Lys Val Ser Asn Phe Leu Lys Trp
445                 450                 455                 460

ATC GAC AAG ATC ATG AAG GCC AGG GCA GGG GCC GCG GGC AGC CGC GGC      1503
Ile Asp Lys Ile Met Lys Ala Arg Ala Gly Ala Ala Gly Ser Arg Gly
                465                 470                 475

CAC AGT GAA GCC CCT GCC ACC TGG ACG GTC CCG CCG CCC CTC CCC CTC      1551
His Ser Glu Ala Pro Ala Thr Trp Thr Val Pro Pro Pro Leu Pro Leu
            480                 485                 490

TAA                                                                   1554
```

(2) INFORMATION FOR SEQ ID NO: 2:

(i) SEQUENCE CHARACTERISTICS:
        (A) LENGTH: 492 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 2:

```
Met Ala Gly Leu Leu His Leu Val Leu Leu Ser Thr Ala Leu Gly Gly
1               5                   10                  15

Leu Leu Arg Pro Ala Gly Ser Val Phe Leu Pro Arg Asp Gln Ala His
                20                  25                  30

Arg Val Leu Gln Arg Ala Arg Arg Ala Asn Ser Phe Leu Glu Glu Val
            35                  40                  45

Lys Gln Gly Asn Leu Glu Arg Glu Cys Leu Glu Glu Ala Cys Ser Leu
        50                  55                  60

Glu Glu Ala Arg Glu Val Phe Glu Asp Ala Glu Gln Thr Asp Glu Phe
65                  70                  75                  80

Trp Ser Lys Tyr Lys Asp Gly Asp Gln Cys Glu Gly His Pro Cys Leu
                85                  90                  95

Asn Gln Gly His Cys Lys Asp Gly Ile Gly Asp Tyr Thr Cys Thr Cys
                100                 105                 110

Ala Glu Gly Phe Glu Gly Lys Asn Cys Glu Phe Ser Thr Arg Glu Ile
            115                 120                 125

Cys Ser Leu Asp Asn Gly Gly Cys Asp Gln Phe Cys Arg Glu Glu Arg
        130                 135                 140

Ser Glu Val Arg Cys Ser Cys Ala His Gly Tyr Val Leu Gly Asp Asp
145                 150                 155                 160

Ser Lys Ser Cys Val Ser Thr Glu Arg Phe Pro Cys Gly Lys Phe Thr
                165                 170                 175

Gln Gly Arg Ser Arg Arg Trp Ala Ile His Thr Ser Glu Asp Ala Leu
                180                 185                 190

Asp Ala Ser Glu Leu Glu His Tyr Asp Pro Ala Asp Leu Ser Pro Thr
            195                 200                 205

Glu Ser Ser Leu Asp Leu Leu Gly Leu Asn Arg Thr Glu Pro Ser Ala
        210                 215                 220

Gly Glu Asp Gly Ser Gln Val Val Arg Ile Val Gly Gly Arg Asp Cys
225                 230                 235                 240

Ala Glu Gly Glu Cys Pro Trp Gln Ala Leu Leu Val Asn Glu Glu Asn
                245                 250                 255
```

-continued

```
Glu Gly Phe Cys Gly Gly Thr Ile Leu Asn Glu Phe Tyr Val Leu Thr
            260                 265                 270

Ala Ala His Cys Leu His Gln Ala Lys Arg Phe Thr Val Arg Val Gly
            275                 280                 285

Asp Arg Asn Thr Glu Gln Glu Gly Asn Glu Met Ala His Glu Val
290                 295                 300

Glu Met Thr Val Lys His Ser Arg Phe Val Lys Glu Thr Tyr Asp Phe
305                 310                 315                 320

Asp Ile Ala Val Leu Arg Leu Lys Thr Pro Ile Arg Phe Arg Arg Asn
                325                 330                 335

Val Ala Pro Ala Cys Leu Pro Glu Lys Asp Trp Ala Glu Ala Thr Leu
                340                 345                 350

Met Thr Gln Lys Thr Gly Ile Val Ser Gly Phe Gly Arg Thr His Glu
                355                 360                 365

Lys Gly Arg Leu Ser Ser Thr Leu Lys Met Leu Glu Val Pro Tyr Val
370                 375                 380

Asp Arg Ser Thr Cys Lys Leu Ser Ser Ser Phe Thr Ile Thr Pro Asn
385                 390                 395                 400

Met Phe Cys Ala Gly Tyr Asp Thr Gln Pro Glu Asp Ala Cys Gln Gly
                405                 410                 415

Asp Ser Gly Gly Pro His Val Thr Arg Phe Lys Asp Thr Tyr Phe Val
                420                 425                 430

Thr Gly Ile Val Ser Trp Gly Glu Gly Cys Ala Arg Lys Gly Lys Phe
            435                 440                 445

Gly Val Tyr Thr Lys Val Ser Asn Phe Leu Lys Trp Ile Asp Lys Ile
450                 455                 460

Met Lys Ala Arg Ala Gly Ala Ala Gly Ser Arg Gly His Ser Glu Ala
465                 470                 475                 480

Pro Ala Thr Trp Thr Val Pro Pro Leu Pro Leu
                485                 490
```

(2) INFORMATION FOR SEQ ID NO: 3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 3:

CGTCCTGGAT CCATCGAGGG TAGAATCCAG CGTACTCCAA AG                        42

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 4:

GCGAAGCTTG ATCACATGTC TCG                                             23

(2) INFORMATION FOR SEQ ID NO: 5:

(i) SEQUENCE CHARACTERISTICS:
        (A) LENGTH: 44 base pairs

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 5:

CGTCCTGGAT CCATCGAGGG TAGAATCCAG AAAACCCCTC AAAT                    44

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 6:

GCGAAGCTTA CATGTCTCGA TC                                            22

(2) INFORMATION FOR SEQ ID NO: 7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 7:

CCTGGATCCA TCGAGGGTAG GTTCCCAACC ATTCCCTTAT                         40

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 8:

CCGAAGCTTA GAAGCCACAG CTGCCC                                        26

(2) INFORMATION FOR SEQ ID NO: 9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 9:

CGTCCTGGAT CCATCGAGGG TAGGTACTCG CGGGAGAAG                          39

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)
```

(xi) SEQUENCE DESCRIPTION: SEQ ID NO: 10:

CGACCGAAGC TTCAGAGTTC GTTGTG                                              26

(2) INFORMATION FOR SEQ ID NO: 11:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 11:

CGTCCTGGAT CCATCGAGGG TAGGGCTATC GACGCCCCTA AG                             42

(2) INFORMATION FOR SEQ ID NO: 12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 12:

CGACCGAAGC TTATCGGCAG TGGGGCCCCT                                          30

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 13:

CGACCGAAGC TTAGGCCTTG CAGGAGCGG                                           29

(2) INFORMATION FOR SEQ ID NO: 14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 14:

CGACCGAAGC TTACTTCTTG CATGACTTCC CG                                       32

(2) INFORMATION FOR SEQ ID NO: 15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 15:

CGTCCTGGAT CCATCGAGGG TAGGGGCACC AACAAATGCC GG                            42

(2) INFORMATION FOR SEQ ID NO: 16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 16:

```
CGACCGAAGC TTAGTCCAGG CTGCGGCAG                              29
```

(2) INFORMATION FOR SEQ ID NO: 17:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 17:

```
CGTCCTGGAT CCATCGAGGG TAGGGTGCCT CCACCCCAGT G                41
```

(2) INFORMATION FOR SEQ ID NO: 18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 18:

```
CGACCGAAGC TTACTGGTCG CAGAGCTCG                              29
```

(2) INFORMATION FOR SEQ ID NO: 19:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 19:

```
CCTTGATCAA TCGAGGGTAG GGGTGGTCAG TGCTCTCTGA ATAACG           46
```

(2) INFORMATION FOR SEQ ID NO: 20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 20:

```
CGCAAGCTTA CTTAAACTCA TAGCAGGTG                              29
```

(2) INFORMATION FOR SEQ ID NO: 21:

(i) SEQUENCE CHARACTERISTICS:
        (A) LENGTH: 44 base pairs

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 21:

CGTCCTGGAT CCATCGAGGG TAGGGCGGTG AATTCCTCTT GCCG                    44

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 22:

CGACCGAAGC TTAGATGTGG CAGCCACGCT                                    30

(2) INFORMATION FOR SEQ ID NO: 23:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 23:

CGTCCTGGAT CCATCGAGGG TAGGGTGTCC AACTGCACGG CT                      42

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 24:

CGACCGAAGC TTAGATGCTG CAGTCCTCCT                                    30

(2) INFORMATION FOR SEQ ID NO: 25:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 25:

CGTCCTGGAT CCATCGAGGG TAGGAGTAAA TACAAAGATG GAGACCA                 47

(2) INFORMATION FOR SEQ ID NO: 26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)
```

(xi) SEQUENCE DESCRIPTION: SEQ ID NO: 26:

CGACCGAAGC TTACCAGGTG GCAGGGGCTT                                           30

(2) INFORMATION FOR SEQ ID NO: 27:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 27:

CTGCCTGGAT CCATCGAGGG TAGGAAAGTG TATCTCTCAT CAGAGTGCAA GACTGGGAAT           60

GG                                                                         62

(2) INFORMATION FOR SEQ ID NO: 28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 28:

CGACCGAAGC TTATTCACAC TCAAGAATGT CGC                                       33

(2) INFORMATION FOR SEQ ID NO: 29:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 29:

CTGCCTGGAT CCATCGAGGG TAGGGTCCAG GACTGCTACC AT                             42

(2) INFORMATION FOR SEQ ID NO: 30:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 30:

CGACCGAAGC TTACGCTTCT GTTCCTGAGC A                                         31

(2) INFORMATION FOR SEQ ID NO: 31:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 31:

```
CCTGGATCCA TCGAGGGTAG GGTCTACCTC CAGACATCCT                    40

(2) INFORMATION FOR SEQ ID NO: 32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 32:

CCGAAGCTTC AAGCATTTCC AAGATC                                   26

(2) INFORMATION FOR SEQ ID NO: 33:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 33:

CCTGGATCCA TCGAGGGTAG GGGCGAGCCA CCAACCCAG                     39

(2) INFORMATION FOR SEQ ID NO: 34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 34:

CCGAAGCTTA CACGATCCCG AACTG                                    25

(2) INFORMATION FOR SEQ ID NO: 35:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 35:

CCGAGATCTA TCGAGGGTAG GCAGGTCAAA CTGCAGCA                      38

(2) INFORMATION FOR SEQ ID NO: 36:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 36:

GCCAAGCTTA ATTCAGATCC TCTTCTGAG                                29

(2) INFORMATION FOR SEQ ID NO: 37:
```

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 37:

Gly Ser Ile Glu Gly Arg
    1               5

(2) INFORMATION FOR SEQ ID NO: 38:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 38:

Ile Glu Gly Arg
1

(2) INFORMATION FOR SEQ ID NO: 39:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 39:

Tyr Trp Thr Asp
1

(2) INFORMATION FOR SEQ ID NO: 40:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 40:

Ile Gln Gly Arg
1

(2) INFORMATION FOR SEQ ID NO: 41:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 41:

Ala Glu Gly Arg
1

(2) INFORMATION FOR SEQ ID NO: 42:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO: 42:

Ala Gln Gly Arg
1

(2) INFORMATION FOR SEQ ID NO: 43:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO: 43:

Ile Cys Gly Arg
1

(2) INFORMATION FOR SEQ ID NO: 44:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO: 44:

Ala Cys Gly Arg
1

(2) INFORMATION FOR SEQ ID NO: 45:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO: 45:

Ile Met Gly Arg
1

(2) INFORMATION FOR SEQ ID NO: 46:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO: 46:

Ala Met Gly Arg
1

(2) INFORMATION FOR SEQ ID NO: 47:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 47:

His His His His His His
1               5

(2) INFORMATION FOR SEQ ID NO: 48:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 48:

Met Gly Ser His His His His His Gly Ser Ile Glu Gly Arg
1               5                   10                  15

(2) INFORMATION FOR SEQ ID NO: 49:

(i) SEQUENCE CHARACTERISTICS:
        (A) LENGTH: 119 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 49:

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
                20                  25                  30

His Pro Ala Glu Asn Gly Lys Ser Asn Phe Leu Asn Cys Tyr Val Ser
                35                  40                  45

Gly Phe His Pro Ser Asp Ile Glu Val Asp Leu Leu Lys Asn Gly Glu
            50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
                100                 105                 110

Val Lys Trp Asp Arg Asp Met
            115

(2) INFORMATION FOR SEQ ID NO: 50:

(i) SEQUENCE CHARACTERISTICS:
        (A) LENGTH: 119 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 50:

Met Ala Arg Ser Val Thr Leu Val Phe Leu Val Leu Val Ser Leu Thr

```
              1               5                  10                  15
          Gly Leu Tyr Ala Ile Gln Lys Thr Pro Gln Ile Gln Val Tyr Ser Arg
                          20                  25                  30

His Pro Pro Glu Asn Gly Lys Pro Asn Ile Leu Asn Cys Tyr Val Thr
                          35                  40                  45

Gln Phe His Pro Pro His Ile Glu Ile Gln Met Leu Lys Asn Gly Lys
                  50                  55                  60

Lys Ile Pro Lys Val Glu Met Ser Asp Met Ser Phe Ser Lys Asp Trp
          65                      70                  75                  80

Ser Phe Tyr Ile Leu Ala His Thr Glu Phe Thr Pro Thr Glu Thr Asp
                              85                  90                  95

Thr Tyr Ala Cys Arg Val Lys His Asp Ser Met Ala Glu Pro Lys Thr
                          100                 105                 110

Val Tyr Trp Asp Arg Asp Met
                          115
```

(2) INFORMATION FOR SEQ ID NO: 51:

(i) SEQUENCE CHARACTERISTICS:
        (A) LENGTH: 217 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 51:

```
          Met Ala Thr Gly Ser Arg Thr Ser Leu Leu Leu Ala Phe Gly Leu Leu
          1               5                  10                  15

Cys Leu Pro Trp Leu Gln Glu Gly Ser Ala Phe Pro Thr Ile Pro Leu
                          20                  25                  30

Ser Arg Leu Phe Asp Asn Ala Ser Leu Arg Ala His Arg Leu His Gln
                          35                  40                  45

Leu Ala Phe Asp Thr Tyr Gln Glu Phe Glu Glu Ala Tyr Ile Pro Lys
                  50                  55                  60

Glu Gln Lys Tyr Ser Phe Leu Gln Asn Pro Gln Thr Ser Leu Cys Phe
          65                      70                  75                  80

Ser Glu Ser Ile Pro Thr Pro Ser Asn Arg Glu Glu Thr Gln Gln Lys
                              85                  90                  95

Ser Asn Leu Glu Leu Leu Arg Ile Ser Leu Leu Leu Ile Gln Ser Trp
                          100                 105                 110

Leu Glu Pro Val Gln Phe Leu Arg Ser Val Phe Ala Asn Ser Leu Val
                          115                 120                 125

Tyr Gly Ala Ser Asp Ser Asn Val Tyr Asp Leu Leu Lys Asp Leu Glu
                  130                 135                 140

Glu Gly Ile Gln Thr Leu Met Gly Arg Leu Glu Asp Gly Ser Pro Arg
          145                     150                 155                 160

Thr Gly Gln Ile Phe Lys Gln Thr Tyr Ser Lys Phe Asp Thr Asn Ser
                              165                 170                 175

His Asn Asp Asp Ala Leu Leu Lys Asn Tyr Gly Leu Leu Tyr Cys Phe
                          180                 185                 190

Arg Lys Asp Met Asp Lys Val Glu Thr Phe Leu Arg Ile Val Gln Cys
                          195                 200                 205

Arg Ser Val Glu Gly Ser Cys Gly Phe
                  210                 215
```

(2) INFORMATION FOR SEQ ID NO: 52:

(i) SEQUENCE CHARACTERISTICS:
    (A) LENGTH: 4544 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO: 52:

```
Met Leu Thr Pro Pro Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
            35                  40                  45

Gly Glu Arg Asp Cys Pro Asp Gly Ser Asp Glu Ala Pro Glu Ile Cys
    50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
            115                 120                 125

Asp Gly Pro Thr Cys Tyr Cys Asn Ser Ser Phe Gln Leu Gln Ala Asp
    130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
            195                 200                 205

Ile Leu Ala Thr Tyr Leu Ser Gly Ala Gln Val Ser Thr Ile Thr Pro
    210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
            275                 280                 285

Trp Leu Thr Gly Asn Phe Tyr Phe Val Asp Asp Ile Asp Asp Arg Ile
    290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
            355                 360                 365
```

-continued

```
Pro His Gly Ile Thr Leu Asp Leu Val Ser Arg Leu Val Tyr Trp Ala
    370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
    690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735

Tyr Glu Gly Pro Glu Leu Asn His Ala Phe Gly Leu Cys His His Gly
            740                 745                 750

Asn Tyr Leu Phe Trp Thr Glu Tyr Arg Ser Gly Ser Val Tyr Arg Leu
        755                 760                 765

Glu Arg Gly Val Gly Gly Ala Pro Pro Thr Val Thr Leu Leu Arg Ser
    770                 775                 780

Glu Arg Pro Pro Ile Phe Glu Ile Arg Met Tyr Asp Ala Gln Gln Gln
785                 790                 795                 800
```

```
Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
            820                 825                 830

Gln Val Leu Asp Ala Asp Gly Val Thr Cys Leu Ala Asn Pro Ser Tyr
            835                 840                 845

Val Pro Pro Pro Gln Cys Gln Pro Gly Glu Phe Ala Cys Ala Asn Ser
            850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
            885                 890                 895

Ser Asp Arg Phe Lys Cys Glu Asn Asn Arg Cys Ile Pro Asn Arg Trp
            900                 905                 910

Leu Cys Asp Gly Asp Asn Asp Cys Gly Asn Ser Glu Asp Glu Ser Asn
            915                 920                 925

Ala Thr Cys Ser Ala Arg Thr Cys Pro Pro Asn Gln Phe Ser Cys Ala
            930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
            965                 970                 975

Phe Pro Leu Thr Gln Phe Thr Cys Asn Asn Gly Arg Cys Ile Asn Ile
            980                 985                 990

Asn Trp Arg Cys Asp Asn Asp Asn Asp Cys Gly Asp Asn Ser Asp Glu
            995                 1000                1005

Ala Gly Cys Ser His Ser Cys Ser Ser Thr Gln Phe Lys Cys Asn Ser
            1010                1015                1020

Gly Arg Cys Ile Pro Glu His Trp Thr Cys Asp Gly Asp Asn Asp Cys
1025                1030                1035                1040

Gly Asp Tyr Ser Asp Glu Thr His Ala Asn Cys Thr Asn Gln Ala Thr
            1045                1050                1055

Arg Pro Pro Gly Gly Cys His Thr Asp Glu Phe Gln Cys Arg Leu Asp
            1060                1065                1070

Gly Leu Cys Ile Pro Leu Arg Trp Arg Cys Asp Gly Asp Thr Asp Cys
            1075                1080                1085

Met Asp Ser Ser Asp Glu Lys Ser Cys Glu Gly Val Thr His Val Cys
            1090                1095                1100

Asp Pro Ser Val Lys Phe Gly Cys Lys Asp Ser Ala Arg Cys Ile Ser
1105                1110                1115                1120

Lys Ala Trp Val Cys Asp Gly Asp Asn Asp Cys Glu Asp Asn Ser Asp
            1125                1130                1135

Glu Glu Asn Cys Glu Ser Leu Ala Cys Arg Pro Pro Ser His Pro Cys
            1140                1145                1150

Ala Asn Asn Thr Ser Val Cys Leu Pro Pro Asp Lys Leu Cys Asp Gly
            1155                1160                1165

Asn Asp Asp Cys Gly Asp Gly Ser Asp Glu Gly Glu Leu Cys Asp Gln
            1170                1175                1180

Cys Ser Leu Asn Asn Gly Gly Cys Ser His Asn Cys Ser Val Ala Pro
1185                1190                1195                1200

Gly Glu Gly Ile Val Cys Ser Cys Pro Leu Gly Met Glu Leu Gly Pro
            1205                1210                1215

Asp Asn His Thr Cys Gln Ile Gln Ser Tyr Cys Ala Lys His Leu Lys
```

-continued

```
              1220                1225                1230
Cys Ser Gln Lys Cys Asp Gln Asn Lys Phe Ser Val Lys Cys Ser Cys
                1235                1240                1245

Tyr Glu Gly Trp Val Leu Glu Pro Asp Gly Glu Ser Cys Arg Ser Leu
1250                1255                1260

Asp Pro Phe Lys Pro Phe Ile Ile Phe Ser Asn Arg His Glu Ile Arg
1265                1270                1275                1280

Arg Ile Asp Leu His Lys Gly Asp Tyr Ser Val Leu Val Pro Gly Leu
                1285                1290                1295

Arg Asn Thr Ile Ala Leu Asp Phe His Leu Ser Gln Ser Ala Leu Tyr
                1300                1305                1310

Trp Thr Asp Val Val Glu Asp Lys Ile Tyr Arg Gly Lys Leu Leu Asp
                1315                1320                1325

Asn Gly Ala Leu Thr Ser Phe Glu Val Val Ile Gln Tyr Gly Leu Ala
                1330                1335                1340

Thr Pro Glu Gly Leu Ala Val Asp Trp Ile Ala Gly Asn Ile Tyr Trp
1345                1350                1355                1360

Val Glu Ser Asn Leu Asp Gln Ile Glu Val Ala Lys Leu Asp Gly Thr
                1365                1370                1375

Leu Arg Thr Thr Leu Leu Ala Gly Asp Ile Glu His Pro Arg Ala Ile
                1380                1385                1390

Ala Leu Asp Pro Arg Asp Gly Ile Leu Phe Trp Thr Asp Trp Asp Ala
                1395                1400                1405

Ser Leu Pro Arg Ile Glu Ala Ala Ser Met Ser Gly Ala Gly Arg Arg
                1410                1415                1420

Thr Val His Arg Glu Thr Gly Ser Gly Gly Trp Pro Asn Gly Leu Thr
1425                1430                1435                1440

Val Asp Tyr Leu Glu Lys Arg Ile Leu Trp Ile Asp Ala Arg Ser Asp
                1445                1450                1455

Ala Ile Tyr Ser Ala Arg Tyr Asp Gly Ser Gly His Met Glu Val Leu
                1460                1465                1470

Arg Gly His Glu Phe Leu Ser His Pro Phe Ala Val Thr Leu Tyr Gly
                1475                1480                1485

Gly Glu Val Tyr Trp Thr Asp Trp Arg Thr Asn Thr Leu Ala Lys Ala
                1490                1495                1500

Asn Lys Trp Thr Gly His Asn Val Thr Val Val Gln Arg Thr Asn Thr
1505                1510                1515                1520

Gln Pro Phe Asp Leu Gln Val Tyr His Pro Ser Arg Gln Pro Met Ala
                1525                1530                1535

Pro Asn Pro Cys Glu Ala Asn Gly Gly Gln Gly Pro Cys Ser His Leu
                1540                1545                1550

Cys Leu Ile Asn Tyr Asn Arg Thr Val Ser Cys Ala Cys Pro His Leu
                1555                1560                1565

Met Lys Leu His Lys Asp Asn Thr Thr Cys Tyr Glu Phe Lys Lys Phe
                1570                1575                1580

Leu Leu Tyr Ala Arg Gln Met Glu Ile Arg Gly Val Asp Leu Asp Ala
1585                1590                1595                1600

Pro Tyr Tyr Asn Tyr Ile Ile Ser Phe Thr Val Pro Asp Ile Asp Asn
                1605                1610                1615

Val Thr Val Leu Asp Tyr Asp Ala Arg Glu Gln Arg Val Tyr Trp Ser
                1620                1625                1630

Asp Val Arg Thr Gln Ala Ile Lys Arg Ala Phe Ile Asn Gly Thr Gly
                1635                1640                1645
```

```
Val Glu Thr Val Val Ser Ala Asp Leu Pro Asn Ala His Gly Leu Ala
    1650                1655                1660

Val Asp Trp Val Ser Arg Asn Leu Phe Trp Thr Ser Tyr Asp Thr Asn
1665                1670                1675                1680

Lys Lys Gln Ile Asn Val Ala Arg Leu Asp Gly Ser Phe Lys Asn Ala
            1685                1690                1695

Val Val Gln Gly Leu Glu Gln Pro His Gly Leu Val Val His Pro Leu
            1700                1705                1710

Arg Gly Lys Leu Tyr Trp Thr Asp Gly Asp Asn Ile Ser Met Ala Asn
            1715                1720                1725

Met Asp Gly Ser Asn Arg Thr Leu Leu Phe Ser Gly Gln Lys Gly Pro
        1730                1735                1740

Val Gly Leu Ala Ile Asp Phe Pro Glu Ser Lys Leu Tyr Trp Ile Ser
1745                1750                1755                1760

Ser Gly Asn His Thr Ile Asn Arg Cys Asn Leu Asp Gly Ser Gly Leu
            1765                1770                1775

Glu Val Ile Asp Ala Met Arg Ser Gln Leu Gly Lys Ala Thr Ala Leu
            1780                1785                1790

Ala Ile Met Gly Asp Lys Leu Trp Trp Ala Asp Gln Val Ser Glu Lys
            1795                1800                1805

Met Gly Thr Cys Ser Lys Ala Asp Gly Ser Gly Ser Val Val Leu Arg
        1810                1815                1820

Asn Ser Thr Thr Leu Val Met His Met Lys Val Tyr Asp Glu Ser Ile
1825                1830                1835                1840

Gln Leu Asp His Lys Gly Thr Asn Pro Cys Ser Val Asn Asn Gly Asp
            1845                1850                1855

Cys Ser Gln Leu Cys Leu Pro Thr Ser Glu Thr Thr Arg Ser Cys Met
            1860                1865                1870

Cys Thr Ala Gly Tyr Ser Leu Arg Ser Gly Gln Gln Ala Cys Glu Gly
        1875                1880                1885

Val Gly Ser Phe Leu Leu Tyr Ser Val His Glu Gly Ile Arg Gly Ile
    1890                1895                1900

Pro Leu Asp Pro Asn Asp Lys Ser Asp Ala Leu Val Pro Val Ser Gly
1905                1910                1915                1920

Thr Ser Leu Ala Val Gly Ile Asp Phe His Ala Glu Asn Asp Thr Ile
            1925                1930                1935

Tyr Trp Val Asp Met Gly Leu Ser Thr Ile Ser Arg Ala Lys Arg Asp
        1940                1945                1950

Gln Thr Trp Arg Glu Asp Val Val Thr Asn Gly Ile Gly Arg Val Glu
        1955                1960                1965

Gly Ile Ala Val Asp Trp Ile Ala Gly Asn Ile Tyr Trp Thr Asp Gln
    1970                1975                1980

Gly Phe Asp Val Ile Glu Val Ala Arg Leu Asn Gly Ser Phe Arg Tyr
1985                1990                1995                2000

Val Val Ile Ser Gln Gly Leu Asp Lys Pro Arg Ala Ile Thr Val His
            2005                2010                2015

Pro Glu Lys Gly Tyr Leu Phe Trp Thr Glu Trp Gly Gln Tyr Pro Arg
        2020                2025                2030

Ile Glu Arg Ser Arg Leu Asp Gly Thr Glu Arg Val Val Leu Val Asn
        2035                2040                2045

Val Ser Ile Ser Trp Pro Asn Gly Ile Ser Val Asp Tyr Gln Asp Gly
    2050                2055                2060

Lys Leu Tyr Trp Cys Asp Ala Arg Thr Asp Lys Ile Glu Arg Ile Asp
2065                2070                2075                2080
```

-continued

```
Leu Glu Thr Gly Glu Asn Arg Glu Val Val Leu Ser Ser Asn Asn Met
            2085                2090                2095

Asp Met Phe Ser Val Ser Val Phe Glu Asp Phe Ile Tyr Trp Ser Asp
            2100                2105                2110

Arg Thr His Ala Asn Gly Ser Ile Lys Arg Gly Ser Lys Asp Asn Ala
            2115                2120                2125

Thr Asp Ser Val Pro Leu Arg Thr Gly Ile Gly Val Gln Leu Lys Asp
            2130                2135                2140

Ile Lys Val Phe Asn Arg Asp Arg Gln Lys Gly Thr Asn Val Cys Ala
2145                2150                2155                2160

Val Ala Asn Gly Gly Cys Gln Gln Leu Cys Leu Tyr Arg Gly Arg Gly
            2165                2170                2175

Gln Arg Ala Cys Ala Cys Ala His Gly Met Leu Ala Glu Asp Gly Ala
            2180                2185                2190

Ser Cys Arg Glu Tyr Ala Gly Tyr Leu Leu Tyr Ser Glu Arg Thr Ile
            2195                2200                2205

Leu Lys Ser Ile His Leu Ser Asp Glu Arg Asn Leu Asn Ala Pro Val
            2210                2215                2220

Gln Pro Phe Glu Asp Pro Glu His Met Lys Asn Val Ile Ala Leu Ala
2225                2230                2235                2240

Phe Asp Tyr Arg Ala Gly Thr Ser Pro Gly Thr Pro Asn Arg Ile Phe
            2245                2250                2255

Phe Ser Asp Ile His Phe Gly Asn Ile Gln Gln Ile Asn Asp Asp Gly
            2260                2265                2270

Ser Arg Arg Ile Thr Ile Val Glu Asn Val Gly Ser Val Glu Gly Leu
            2275                2280                2285

Ala Tyr His Arg Gly Trp Asp Thr Leu Tyr Trp Thr Ser Tyr Thr Thr
            2290                2295                2300

Ser Thr Ile Thr Arg His Thr Val Asp Gln Thr Arg Pro Gly Ala Phe
2305                2310                2315                2320

Glu Arg Glu Thr Val Ile Thr Met Ser Gly Asp Asp His Pro Arg Ala
            2325                2330                2335

Phe Val Leu Asp Glu Cys Gln Asn Leu Met Phe Trp Thr Asn Trp Asn
            2340                2345                2350

Glu Gln His Pro Ser Ile Met Arg Ala Ala Leu Ser Gly Ala Asn Val
            2355                2360                2365

Leu Thr Leu Ile Glu Lys Asp Ile Arg Thr Pro Asn Gly Leu Ala Ile
            2370                2375                2380

Asp His Arg Ala Glu Lys Leu Tyr Phe Ser Asp Ala Thr Leu Asp Lys
2385                2390                2395                2400

Ile Glu Arg Cys Glu Tyr Asp Gly Ser His Arg Tyr Val Ile Leu Lys
            2405                2410                2415

Ser Glu Pro Val His Pro Phe Gly Leu Ala Val Tyr Gly Glu His Ile
            2420                2425                2430

Phe Trp Thr Asp Trp Val Arg Arg Ala Val Gln Arg Ala Asn Lys His
            2435                2440                2445

Val Gly Ser Asn Met Lys Leu Leu Arg Val Asp Ile Pro Gln Gln Pro
            2450                2455                2460

Met Gly Ile Ile Ala Val Ala Asn Asp Thr Asn Ser Cys Glu Leu Ser
2465                2470                2475                2480

Pro Cys Arg Ile Asn Asn Gly Gly Cys Gln Asp Leu Cys Leu Leu Thr
            2485                2490                2495

His Gln Gly His Val Asn Cys Ser Cys Arg Gly Gly Arg Ile Leu Gln
```

```
                2500                2505                2510
Asp Asp Leu Thr Cys Arg Ala Val Asn Ser Ser Cys Arg Ala Gln Asp
                2515                2520                2525

Glu Phe Glu Cys Ala Asn Gly Glu Cys Ile Asn Phe Ser Leu Thr Cys
            2530                2535                2540

Asp Gly Val Pro His Cys Lys Asp Lys Ser Asp Glu Lys Pro Ser Tyr
2545                2550                2555                2560

Cys Asn Ser Arg Arg Cys Lys Lys Thr Phe Arg Gln Cys Ser Asn Gly
                2565                2570                2575

Arg Cys Val Ser Asn Met Leu Trp Cys Asn Gly Ala Asp Asp Cys Gly
                2580                2585                2590

Asp Gly Ser Asp Glu Ile Pro Cys Asn Lys Thr Ala Cys Gly Val Gly
                2595                2600                2605

Glu Phe Arg Cys Arg Asp Gly Thr Cys Ile Gly Asn Ser Ser Arg Cys
            2610                2615                2620

Asn Gln Phe Val Asp Cys Glu Asp Ala Ser Asp Glu Met Asn Cys Ser
2625                2630                2635                2640

Ala Thr Asp Cys Ser Ser Tyr Phe Arg Leu Gly Val Lys Gly Val Leu
                2645                2650                2655

Phe Gln Pro Cys Glu Arg Thr Ser Leu Cys Tyr Ala Pro Ser Trp Val
            2660                2665                2670

Cys Asp Gly Ala Asn Asp Cys Gly Asp Tyr Ser Asp Glu Arg Asp Cys
            2675                2680                2685

Pro Gly Val Lys Arg Pro Arg Cys Pro Leu Asn Tyr Phe Ala Cys Pro
            2690                2695                2700

Ser Gly Arg Cys Ile Pro Met Ser Trp Thr Cys Asp Lys Glu Asp Asp
2705                2710                2715                2720

Cys Glu His Gly Glu Asp Glu Thr His Cys Asn Lys Phe Cys Ser Glu
            2725                2730                2735

Ala Gln Phe Glu Cys Gln Asn His Arg Cys Ile Ser Lys Gln Trp Leu
            2740                2745                2750

Cys Asp Gly Ser Asp Asp Cys Gly Asp Gly Ser Asp Glu Ala Ala His
            2755                2760                2765

Cys Glu Gly Lys Thr Cys Gly Pro Ser Ser Phe Ser Cys Pro Gly Thr
            2770                2775                2780

His Val Cys Val Pro Glu Arg Trp Leu Cys Asp Gly Asp Lys Asp Cys
2785                2790                2795                2800

Ala Asp Gly Ala Asp Glu Ser Ile Ala Ala Gly Cys Leu Tyr Asn Ser
            2805                2810                2815

Thr Cys Asp Asp Arg Glu Phe Met Cys Gln Asn Arg Gln Cys Ile Pro
            2820                2825                2830

Lys His Phe Val Cys Asp His Asp Arg Asp Cys Ala Asp Gly Ser Asp
            2835                2840                2845

Glu Ser Pro Glu Cys Glu Tyr Pro Thr Cys Gly Pro Ser Glu Phe Arg
            2850                2855                2860

Cys Ala Asn Gly Arg Cys Leu Ser Ser Arg Gln Trp Glu Cys Asp Gly
2865                2870                2875                2880

Glu Asn Asp Cys His Asp Gln Ser Asp Glu Ala Pro Lys Asn Pro His
                2885                2890                2895

Cys Thr Ser Pro Glu His Lys Cys Asn Ala Ser Ser Gln Phe Leu Cys
            2900                2905                2910

Ser Ser Gly Arg Cys Val Ala Glu Ala Leu Leu Cys Asn Gly Gln Asp
            2915                2920                2925
```

-continued

```
Asp Cys Gly Asp Ser Ser Asp Glu Arg Gly Cys His Ile Asn Glu Cys
    2930                2935                2940

Leu Ser Arg Lys Leu Ser Gly Cys Ser Gln Asp Cys Glu Asp Leu Lys
2945            2950                2955                2960

Ile Gly Phe Lys Cys Arg Cys Arg Pro Gly Phe Arg Leu Lys Asp Asp
            2965                2970                2975

Gly Arg Thr Cys Ala Asp Val Asp Glu Cys Ser Thr Thr Phe Pro Cys
        2980                2985                2990

Ser Gln Arg Cys Ile Asn Thr His Gly Ser Tyr Lys Cys Leu Cys Val
            2995                3000                3005

Glu Gly Tyr Ala Pro Arg Gly Gly Asp Pro His Ser Cys Lys Ala Val
        3010                3015                3020

Thr Asp Glu Glu Pro Phe Leu Ile Phe Ala Asn Arg Tyr Tyr Leu Arg
3025                3030                3035                3040

Lys Leu Asn Leu Asp Gly Ser Asn Tyr Thr Leu Leu Lys Gln Gly Leu
                3045                3050                3055

Asn Asn Ala Val Ala Leu Asp Phe Asp Tyr Arg Glu Gln Met Ile Tyr
            3060                3065                3070

Trp Thr Asp Val Thr Thr Gln Gly Ser Met Ile Arg Arg Met His Leu
        3075                3080                3085

Asn Gly Ser Asn Val Gln Val Leu His Arg Thr Gly Leu Ser Asn Pro
    3090                3095                3100

Asp Gly Leu Ala Val Asp Trp Val Gly Gly Asn Leu Tyr Trp Cys Asp
3105                3110                3115                3120

Lys Gly Arg Asp Thr Ile Glu Val Ser Lys Leu Asn Gly Ala Tyr Arg
                3125                3130                3135

Thr Val Leu Val Ser Ser Gly Leu Arg Glu Pro Arg Ala Leu Val Val
            3140                3145                3150

Asp Val Gln Asn Gly Tyr Leu Tyr Trp Thr Asp Trp Gly Asp His Ser
        3155                3160                3165

Leu Ile Gly Arg Ile Gly Met Asp Gly Ser Ser Arg Ser Val Ile Val
    3170                3175                3180

Asp Thr Lys Ile Thr Trp Pro Asn Gly Leu Thr Leu Asp Tyr Val Thr
3185                3190                3195                3200

Glu Arg Ile Tyr Trp Ala Asp Ala Arg Glu Asp Tyr Ile Glu Phe Ala
                3205                3210                3215

Ser Leu Asp Gly Ser Asn Arg His Val Val Leu Ser Gln Asp Ile Pro
            3220                3225                3230

His Ile Phe Ala Leu Thr Leu Phe Glu Asp Tyr Val Tyr Trp Thr Asp
        3235                3240                3245

Trp Glu Thr Lys Ser Ile Asn Arg Ala His Lys Thr Thr Gly Thr Asn
    3250                3255                3260

Lys Thr Leu Leu Ile Ser Thr Leu His Arg Pro Met Asp Leu His Val
3265                3270                3275                3280

Phe His Ala Leu Arg Gln Pro Asp Val Pro Asn His Pro Cys Lys Val
                3285                3290                3295

Asn Asn Gly Gly Cys Ser Asn Leu Cys Leu Leu Ser Pro Gly Gly Gly
            3300                3305                3310

His Lys Cys Ala Cys Pro Thr Asn Phe Tyr Leu Gly Ser Asp Gly Arg
        3315                3320                3325

Thr Cys Val Ser Asn Cys Thr Ala Ser Gln Phe Val Cys Lys Asn Asp
    3330                3335                3340

Lys Cys Ile Pro Phe Trp Trp Lys Cys Asp Thr Glu Asp Asp Cys Gly
3345                3350                3355                3360
```

-continued

Asp His Ser Asp Glu Pro Pro Asp Cys Pro Glu Phe Lys Cys Arg Pro
            3365                3370                3375

Gly Gln Phe Gln Cys Ser Thr Gly Ile Cys Thr Asn Pro Ala Phe Ile
        3380                3385                3390

Cys Asp Gly Asp Asn Asp Cys Gln Asp Asn Ser Asp Glu Ala Asn Cys
    3395                3400                3405

Asp Ile His Val Cys Leu Pro Ser Gln Phe Lys Cys Thr Asn Thr Asn
    3410                3415                3420

Arg Cys Ile Pro Gly Ile Phe Arg Cys Asn Gly Gln Asp Asn Cys Gly
3425                3430                3435                3440

Asp Gly Glu Asp Glu Arg Asp Cys Pro Glu Val Thr Cys Ala Pro Asn
            3445                3450                3455

Gln Phe Gln Cys Ser Ile Thr Lys Arg Cys Ile Pro Arg Val Trp Val
            3460                3465                3470

Cys Asp Arg Asp Asn Asp Cys Val Asp Gly Ser Asp Glu Pro Ala Asn
        3475                3480                3485

Cys Thr Gln Met Thr Cys Gly Val Asp Glu Phe Arg Cys Lys Asp Ser
    3490                3495                3500

Gly Arg Cys Ile Pro Ala Arg Trp Lys Cys Asp Gly Glu Asp Asp Cys
3505                3510                3515                3520

Gly Asp Gly Ser Asp Glu Pro Lys Glu Glu Cys Asp Glu Arg Thr Cys
            3525                3530                3535

Glu Pro Tyr Gln Phe Arg Cys Lys Asn Asn Arg Cys Val Pro Gly Arg
            3540                3545                3550

Trp Gln Cys Asp Tyr Asp Asn Asp Cys Gly Asp Asn Ser Asp Glu Glu
        3555                3560                3565

Ser Cys Thr Pro Arg Pro Cys Ser Glu Ser Glu Phe Ser Cys Ala Asn
    3570                3575                3580

Gly Arg Cys Ile Ala Gly Arg Trp Lys Cys Asp Gly Asp His Asp Cys
3585                3590                3595                3600

Ala Asp Gly Ser Asp Glu Lys Asp Cys Thr Pro Arg Cys Asp Met Asp
            3605                3610                3615

Gln Phe Gln Cys Lys Ser Gly His Cys Ile Pro Leu Arg Trp Arg Cys
            3620                3625                3630

Asp Ala Asp Ala Asp Cys Met Asp Gly Ser Asp Glu Glu Ala Cys Gly
        3635                3640                3645

Thr Gly Val Arg Thr Cys Pro Leu Asp Glu Phe Gln Cys Asn Asn Thr
    3650                3655                3660

Leu Cys Lys Pro Leu Ala Trp Lys Cys Asp Gly Glu Asp Asp Cys Gly
3665                3670                3675                3680

Asp Asn Ser Asp Glu Asn Pro Glu Glu Cys Ala Arg Phe Val Cys Pro
            3685                3690                3695

Pro Asn Arg Pro Phe Arg Cys Lys Asn Asp Arg Val Cys Leu Trp Ile
            3700                3705                3710

Gly Arg Gln Cys Asp Gly Thr Asp Asn Cys Gly Asp Gly Thr Asp Glu
        3715                3720                3725

Glu Asp Cys Glu Pro Pro Thr Ala His Thr Thr His Cys Lys Asp Lys
    3730                3735                3740

Lys Glu Phe Leu Cys Arg Asn Gln Arg Cys Leu Ser Ser Ser Leu Arg
3745                3750                3755                3760

Cys Asn Met Phe Asp Asp Cys Gly Asp Gly Ser Asp Glu Glu Asp Cys
            3765                3770                3775

Ser Ile Asp Pro Lys Leu Thr Ser Cys Ala Thr Asn Ala Ser Ile Cys

-continued

```
                 3780            3785             3790
Gly Asp Glu Ala Arg Cys Val Arg Thr Glu Lys Ala Ala Tyr Cys Ala
                 3795            3800             3805

Cys Arg Ser Gly Phe His Thr Val Pro Gly Gln Pro Gly Cys Gln Asp
        3810            3815             3820

Ile Asn Glu Cys Leu Arg Phe Gly Thr Cys Ser Gln Leu Cys Asn Asn
3825            3830             3835            3840

Thr Lys Gly Gly His Leu Cys Ser Cys Ala Arg Asn Phe Met Lys Thr
                 3845            3850             3855

His Asn Thr Cys Lys Ala Glu Gly Ser Glu Tyr Gln Val Leu Tyr Ile
        3860            3865             3870

Ala Asp Asp Asn Glu Ile Arg Ser Leu Phe Pro Gly His Pro His Ser
        3875            3880             3885

Ala Tyr Glu Gln Ala Phe Gln Gly Asp Glu Ser Val Arg Ile Asp Ala
        3890            3895             3900

Met Asp Val His Val Lys Ala Gly Arg Val Tyr Trp Thr Asn Trp His
3905            3910            3915             3920

Thr Gly Thr Ile Ser Tyr Arg Ser Leu Pro Pro Ala Ala Pro Pro Thr
        3925            3930             3935

Thr Ser Asn Arg His Arg Arg Gln Ile Asp Arg Gly Val Thr His Leu
        3940            3945             3950

Asn Ile Ser Gly Leu Lys Met Pro Arg Gly Ile Ala Ile Asp Trp Val
        3955            3960             3965

Ala Gly Asn Val Tyr Trp Thr Asp Ser Gly Arg Asp Val Ile Glu Val
        3970            3975             3980

Ala Gln Met Lys Gly Glu Asn Arg Lys Thr Leu Ile Ser Gly Met Ile
3985            3990            3995             4000

Asp Glu Pro His Ala Ile Val Val Asp Pro Leu Arg Gly Thr Met Tyr
        4005            4010             4015

Trp Ser Asp Trp Gly Asn His Pro Lys Ile Glu Thr Ala Ala Met Asp
        4020            4025             4030

Gly Thr Leu Arg Glu Thr Leu Val Gln Asp Asn Ile Gln Trp Pro Thr
        4035            4040             4045

Gly Leu Ala Val Asp Tyr His Asn Glu Arg Leu Tyr Trp Ala Asp Ala
        4050            4055             4060

Lys Leu Ser Val Ile Gly Ser Ile Arg Leu Asn Gly Thr Asp Pro Ile
4065            4070             4075            4080

Val Ala Ala Asp Ser Lys Arg Gly Leu Ser His Pro Phe Ser Ile Asp
                 4085            4090             4095

Val Phe Glu Asp Tyr Ile Tyr Gly Val Thr Tyr Ile Asn Asn Arg Val
        4100            4105             4110

Phe Lys Ile His Lys Phe Gly His Ser Pro Leu Val Asn Leu Thr Gly
                 4115            4120             4125

Gly Leu Ser His Ala Ser Asp Val Val Leu Tyr His Gln His Lys Gln
        4130            4135             4140

Pro Glu Val Thr Asn Pro Cys Asp Arg Lys Lys Cys Glu Trp Leu Cys
4145            4150             4155            4160

Leu Leu Ser Pro Ser Gly Pro Val Cys Thr Cys Pro Asn Gly Lys Arg
                 4165            4170             4175

Leu Asp Asn Gly Thr Cys Val Pro Val Pro Ser Pro Thr Pro Pro Pro
                 4180            4185             4190

Asp Ala Pro Arg Pro Gly Thr Cys Asn Leu Gln Cys Phe Asn Gly Gly
                 4195            4200             4205
```

-continued

```
Ser Cys Phe Leu Asn Ala Arg Arg Gln Pro Lys Cys Arg Cys Gln Pro
    4210                4215                4220

Arg Tyr Thr Gly Asp Lys Cys Glu Leu Asp Gln Cys Trp Glu His Cys
4225            4230                4235                4240

Arg Asn Gly Gly Thr Cys Ala Ala Ser Pro Ser Gly Met Pro Thr Cys
                4245                4250                4255

Arg Cys Pro Thr Gly Phe Thr Gly Pro Lys Cys Thr Gln Gln Val Cys
            4260                4265                4270

Ala Gly Tyr Cys Ala Asn Asn Ser Thr Cys Thr Val Asn Gln Gly Asn
        4275                4280                4285

Gln Pro Gln Cys Arg Cys Leu Pro Gly Phe Leu Gly Asp Arg Cys Gln
    4290                4295                4300

Tyr Arg Gln Cys Ser Gly Tyr Cys Glu Asn Phe Gly Thr Cys Gln Met
4305            4310                4315                4320

Ala Ala Asp Gly Ser Arg Gln Cys Arg Cys Thr Ala Tyr Phe Glu Gly
                4325                4330                4335

Ser Arg Cys Glu Val Asn Lys Cys Ser Arg Cys Leu Glu Gly Ala Cys
            4340                4345                4350

Val Val Asn Lys Gln Ser Gly Asp Val Thr Cys Asn Cys Thr Asp Gly
        4355                4360                4365

Arg Val Ala Pro Ser Cys Leu Thr Cys Val Gly His Cys Ser Asn Gly
    4370                4375                4380

Gly Ser Cys Thr Met Asn Ser Lys Met Met Pro Glu Cys Gln Cys Pro
4385            4390                4395                4400

Pro His Met Thr Gly Pro Arg Cys Glu Glu His Val Phe Ser Gln Gln
                4405                4410                4415

Gln Pro Gly His Ile Ala Ser Ile Leu Ile Pro Leu Leu Leu Leu Leu
            4420                4425                4430

Leu Leu Val Leu Val Ala Gly Val Val Phe Trp Tyr Lys Arg Arg Val
        4435                4440                4445

Gln Gly Ala Lys Gly Phe Gln His Gln Arg Met Thr Asn Gly Ala Met
    4450                4455                4460

Asn Val Glu Ile Gly Asn Pro Thr Tyr Lys Met Tyr Glu Gly Gly Glu
4465            4470                4475                4480

Pro Asp Asp Val Gly Gly Leu Leu Asp Ala Asp Phe Ala Leu Asp Pro
                4485                4490                4495

Asp Lys Pro Thr Asn Phe Thr Asn Pro Val Tyr Ala Thr Leu Tyr Met
            4500                4505                4510

Gly Gly His Gly Ser Arg His Ser Leu Ala Ser Thr Asp Glu Lys Arg
        4515                4520                4525

Glu Leu Leu Gly Arg Gly Pro Glu Asp Glu Ile Gly Asp Pro Leu Ala
    4530                4535                4540
```

(2) INFORMATION FOR SEQ ID NO: 53:

(i) SEQUENCE CHARACTERISTICS:
        (A) LENGTH: 487 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 53:

```
Met Ala Gly Leu Leu His Leu Val Leu Leu Ser Thr Ala Leu Gly Gly
1               5                   10                  15

Leu Leu Arg Pro Ala Gly Ser Val Phe Leu Pro Arg Asp Gln Ala His
```

```
                    20                  25                  30
Arg Val Leu Gln Arg Ala Arg Ala Asn Ser Phe Leu Glu Glu Val
            35                  40                  45
Lys Gln Gly Asn Leu Glu Arg Glu Cys Leu Glu Glu Ala Cys Ser Leu
    50                  55                  60
Glu Glu Ala Arg Glu Val Phe Glu Asp Ala Glu Gln Thr Asp Glu Phe
65                  70                  75                  80
Trp Ser Lys Tyr Lys Asp Gly Asp Gln Cys Glu Gly His Pro Cys Leu
                85                  90                  95
Asn Gln Gly His Cys Lys Asp Gly Ile Gly Asp Tyr Thr Cys Thr Cys
            100                 105                 110
Ala Glu Gly Phe Glu Gly Lys Asn Cys Glu Phe Ser Thr Arg Glu Ile
            115                 120                 125
Cys Ser Leu Asp Asn Gly Gly Cys Asp Gln Phe Cys Arg Glu Glu Arg
    130                 135                 140
Ser Glu Val Arg Cys Ser Cys Ala His Gly Tyr Val Leu Gly Asp Asp
145                 150                 155                 160
Ser Lys Ser Cys Val Ser Thr Glu Arg Phe Pro Cys Gly Lys Phe Thr
                165                 170                 175
Gln Gly Arg Ser Arg Arg Trp Ala Ile His Thr Ser Glu Asp Ala Leu
            180                 185                 190
Asp Ala Ser Glu Leu Glu His Tyr Asp Pro Ala Asp Leu Ser Pro Thr
            195                 200                 205
Glu Ser Ser Leu Asp Leu Leu Gly Leu Asn Arg Thr Glu Pro Ser Ala
    210                 215                 220
Gly Glu Asp Gly Ser Gln Val Val Arg Ile Val Gly Gly Arg Asp Cys
225                 230                 235                 240
Ala Glu Gly Glu Cys Pro Trp Gln Ala Leu Leu Val Asn Glu Glu Asn
                245                 250                 255
Glu Gly Phe Cys Gly Gly Thr Ile Leu Asn Glu Phe Tyr Val Leu Thr
            260                 265                 270
Ala Ala His Cys Leu His Gln Ala Lys Arg Phe Thr Val Arg Val Gly
            275                 280                 285
Asp Arg Asn Thr Glu Gln Glu Glu Gly Asn Glu Met Ala His Glu Val
    290                 295                 300
Glu Met Thr Val Lys His Ser Arg Phe Val Lys Glu Thr Tyr Asp Phe
305                 310                 315                 320
Asp Ile Ala Val Leu Arg Leu Lys Thr Pro Ile Arg Phe Arg Arg Asn
                325                 330                 335
Val Ala Pro Ala Cys Leu Pro Glu Lys Asp Trp Ala Glu Ala Thr Leu
            340                 345                 350
Met Thr Gln Lys Thr Gly Ile Val Ser Gly Phe Gly Arg Thr His Glu
            355                 360                 365
Lys Gly Arg Leu Ser Ser Thr Leu Lys Met Leu Glu Val Pro Tyr Val
    370                 375                 380
Asp Arg Ser Thr Cys Lys Leu Ser Ser Phe Thr Ile Thr Pro Asn Met
385                 390                 395                 400
Met Phe Cys Ala Gly Tyr Asp Thr Gln Pro Glu Asp Ala Cys Gln Gly
                405                 410                 415
Asp Ser Gly Gly Pro His Val Thr Arg Phe Lys Asp Thr Tyr Phe Val
            420                 425                 430
Thr Gly Ile Val Ser Trp Gly Glu Gly Cys Ala Arg Lys Gly Lys Phe
            435                 440                 445
```

-continued

```
Gly Val Tyr Thr Lys Val Ser Asn Phe Leu Lys Trp Ile Asp Lys Ile
    450                 455                 460

Met Lys Ala Arg Ala Gly Ala Gly Ser Arg Gly His Ser Glu Ala
465                 470                 475                 480

Pro Ala Thr Trp Thr Val Pro
                485
```

(2) INFORMATION FOR SEQ ID NO: 54:

(i) SEQUENCE CHARACTERISTICS:
        (A) LENGTH: 790 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 54:

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
                20                  25                  30

Lys Cys Glu Glu Asp Glu Glu Phe Thr Cys Arg Ala Phe Gln Tyr His
                35                  40                  45

Ser Lys Glu Gln Gln Cys Val Ile Met Ala Glu Asn Arg Lys Ser Ser
50                  55                  60

Ile Ile Arg Met Arg Asp Val Val Leu Phe Glu Lys Lys Val Tyr Leu
65                  70                  75                  80

Ser Glu Cys Lys Thr Gly Asn Gly Lys Asn Tyr Arg Gly Thr Met Ser
                85                  90                  95

Lys Thr Lys Asn Gly Ile Thr Cys Gln Lys Trp Ser Ser Thr Ser Pro
                100                 105                 110

His Arg Pro Arg Phe Ser Pro Ala Thr His Pro Ser Glu Gly Leu Glu
                115                 120                 125

Glu Asn Tyr Cys Arg Asn Pro Asp Asn Asp Pro Gln Gly Pro Trp Cys
            130                 135                 140

Tyr Thr Thr Asp Pro Glu Lys Arg Tyr Asp Tyr Cys Asp Ile Leu Glu
145                 150                 155                 160

Cys Glu Glu Glu Cys Met His Cys Ser Gly Glu Asn Tyr Asp Gly Lys
                165                 170                 175

Ile Ser Lys Thr Met Ser Gly Leu Glu Cys Gln Ala Trp Asp Ser Gln
                180                 185                 190

Ser Pro His Ala His Gly Tyr Ile Pro Ser Lys Phe Pro Asn Lys Asn
            195                 200                 205

Leu Lys Lys Asn Tyr Cys Arg Asn Pro Asp Arg Glu Leu Arg Pro Trp
        210                 215                 220

Cys Phe Thr Thr Asp Pro Asn Lys Arg Trp Glu Leu Cys Asp Ile Pro
225                 230                 235                 240

Arg Cys Thr Thr Pro Pro Pro Ser Ser Gly Pro Thr Tyr Gln Cys Leu
                245                 250                 255

Lys Gly Thr Gly Glu Asn Tyr Arg Gly Asn Val Ala Val Thr Val Ser
                260                 265                 270

Gly His Thr Cys Gln His Trp Ser Ala Gln Thr Pro His Thr His Asn
            275                 280                 285

Arg Thr Pro Glu Asn Phe Pro Cys Lys Asn Leu Asp Glu Asn Tyr Cys
        290                 295                 300

Arg Asn Pro Asp Gly Lys Arg Ala Pro Trp Cys His Thr Thr Asn Ser
```

-continued

```
         305                 310                 315                 320
  Gln Val Arg Trp Glu Tyr Cys Lys Ile Pro Ser Cys Asp Ser Ser Pro
                  325                 330                 335

Val Ser Thr Glu Glu Leu Ala Pro Thr Ala Pro Pro Glu Leu Thr Pro
                  340                 345                 350

Val Val Gln Asp Cys Tyr His Gly Asp Gly Gln Ser Tyr Arg Gly Thr
                  355                 360                 365

Ser Ser Thr Thr Thr Thr Gly Lys Lys Cys Gln Ser Trp Ser Ser Met
  370                 375                 380

Thr Pro His Arg His Gln Lys Thr Pro Glu Asn Tyr Pro Asn Ala Gly
  385                 390                 395                 400

Leu Thr Met Asn Tyr Cys Arg Asn Pro Asp Ala Asp Lys Gly Pro Trp
                  405                 410                 415

Cys Phe Thr Thr Asp Pro Ser Val Arg Trp Glu Tyr Cys Asn Leu Lys
                  420                 425                 430

Lys Cys Ser Gly Thr Glu Ala Ser Val Val Ala Pro Pro Val Val
                  435                 440                 445

Leu Leu Pro Asn Val Glu Thr Pro Ser Glu Glu Asp Cys Met Phe Gly
  450                 455                 460

Asn Gly Lys Gly Tyr Arg Gly Lys Arg Ala Thr Thr Val Thr Gly Thr
  465                 470                 475                 480

Pro Cys Gln Asp Trp Ala Ala Gln Glu Pro His Arg His Ser Ile Phe
                  485                 490                 495

Thr Pro Glu Thr Asn Pro Arg Ala Gly Leu Glu Lys Asn Tyr Cys Arg
                  500                 505                 510

Asn Pro Asp Gly Asp Val Gly Gly Pro Trp Cys Tyr Thr Thr Asn Pro
                  515                 520                 525

Arg Lys Leu Tyr Asp Tyr Cys Asp Val Pro Gln Cys Ala Ala Pro Ser
  530                 535                 540

Phe Asp Cys Gly Lys Pro Gln Val Glu Pro Lys Lys Cys Pro Gly Arg
  545                 550                 555                 560

Val Val Gly Gly Cys Val Ala His Pro His Ser Trp Pro Trp Gln Val
                  565                 570                 575

Ser Leu Arg Thr Arg Phe Gly Met His Phe Cys Gly Gly Thr Leu Ile
                  580                 585                 590

Ser Pro Glu Trp Val Leu Thr Ala Ala His Cys Leu Glu Lys Ser Pro
                  595                 600                 605

Arg Pro Ser Ser Tyr Lys Val Ile Leu Gly Ala His Gln Glu Val Asn
                  610                 615                 620

Leu Glu Pro His Val Gln Glu Ile Glu Val Ser Arg Leu Phe Leu Glu
  625                 630                 635                 640

Pro Thr Arg Lys Asp Ile Ala Leu Leu Lys Leu Ser Ser Pro Ala Val
                  645                 650                 655

Ile Thr Asp Lys Val Ile Pro Ala Cys Leu Pro Ser Pro Asn Tyr Val
                  660                 665                 670

Val Ala Asp Arg Thr Glu Cys Phe Ile Thr Gly Trp Gly Glu Thr Gln
                  675                 680                 685

Gly Thr Phe Gly Ala Gly Leu Leu Lys Glu Ala Gln Leu Pro Val Ile
                  690                 695                 700

Glu Asn Lys Val Cys Asn Arg Tyr Glu Phe Leu Asn Gly Arg Val Gln
  705                 710                 715                 720

Ser Thr Glu Leu Cys Ala Gly His Leu Ala Gly Gly Thr Asp Ser Cys
                  725                 730                 735
```

```
Gln Gly Asp Ser Gly Gly Pro Leu Val Cys Phe Glu Lys Asp Lys Tyr
            740                 745                 750

Ile Leu Gln Gly Val Thr Ser Trp Gly Leu Gly Cys Ala Arg Pro Asn
            755                 760                 765

Lys Pro Gly Val Tyr Val Arg Val Ser Arg Phe Val Thr Trp Ile Glu
770                 775                 780

Gly Val Met Arg Asn Asn
785                 790

(2) INFORMATION FOR SEQ ID NO: 55:

(i) SEQUENCE CHARACTERISTICS:
        (A) LENGTH: 153 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 55:

Val Tyr Leu Gln Thr Ser Leu Lys Tyr Asn Ile Leu Pro Glu Lys Glu
1               5                   10                  15

Glu Phe Pro Phe Ala Leu Gly Val Gln Thr Leu Pro Gln Thr Cys Asp
                20                  25                  30

Glu Pro Lys Ala His Thr Ser Phe Gln Ile Ser Leu Ser Val Ser Tyr
            35                  40                  45

Thr Gly Ser Arg Ser Ala Ser Asn Met Ala Ile Val Asp Val Lys Met
        50                  55                  60

Val Ser Gly Phe Ile Pro Leu Lys Pro Thr Val Lys Met Leu Glu Arg
65                  70                  75                  80

Ser Asn His Val Ser Arg Thr Glu Val Ser Ser Asn His Val Leu Ile
                85                  90                  95

Tyr Leu Asp Lys Val Ser Asn Gln Thr Leu Ser Leu Phe Phe Thr Val
                100                 105                 110

Leu Gln Asp Val Pro Val Arg Asp Leu Lys Pro Ala Ile Val Lys Val
            115                 120                 125

Tyr Asp Tyr Tyr Glu Thr Asp Glu Phe Ala Ile Ala Glu Tyr Asn Ala
130                 135                 140

Pro Cys Ser Lys Asp Leu Gly Asn Ala
145                 150

(2) INFORMATION FOR SEQ ID NO: 56:

(i) SEQUENCE CHARACTERISTICS:
        (A) LENGTH: 202 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 56:

Met Glu Leu Trp Gly Ala Tyr Leu Leu Leu Cys Leu Phe Ser Leu Leu
1               5                   10                  15

Thr Gln Val Thr Thr Glu Pro Pro Thr Gln Lys Pro Lys Lys Ile Val
                20                  25                  30

Asn Ala Lys Lys Asp Val Val Asn Thr Lys Met Phe Glu Glu Leu Lys
            35                  40                  45

Ser Arg Leu Asp Thr Leu Ala Gln Glu Val Ala Leu Leu Lys Glu Gln
        50                  55                  60
```

```
Gln Ala Leu Gln Thr Val Cys Leu Lys Gly Thr Lys Val His Met Lys
 65                  70                  75                  80

Cys Phe Leu Ala Phe Thr Gln Thr Lys Thr Phe His Glu Ala Ser Glu
                 85                  90                  95

Asp Cys Ile Ser Arg Gly Gly Thr Leu Ser Thr Pro Gln Thr Gly Ser
            100                 105                 110

Glu Asn Asp Ala Leu Tyr Glu Tyr Leu Arg Gln Ser Val Gly Asn Glu
        115                 120                 125

Ala Glu Ile Trp Leu Gly Leu Asn Asp Met Ala Ala Glu Gly Thr Trp
130                 135                 140

Val Asp Met Thr Gly Ala Arg Ile Ala Tyr Lys Asn Trp Glu Thr Glu
145                 150                 155                 160

Ile Thr Ala Gln Pro Asp Gly Gly Lys Thr Glu Asn Cys Ala Val Leu
                165                 170                 175

Ser Gly Ala Ala Asn Gly Lys Trp Phe Asp Lys Arg Cys Arg Asp Gln
            180                 185                 190

Leu Pro Tyr Ile Cys Gln Phe Gly Ile Val
        195                 200

(2) INFORMATION FOR SEQ ID NO: 57:

(i) SEQUENCE CHARACTERISTICS:
        (A) LENGTH: 246 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 57:

Gln Val Lys Leu Gln Gln Ser Gly Ala Glu Leu Val Lys Pro Gly Ala
 1               5                  10                  15

Ser Val Lys Met Ser Cys Lys Ala Ser Gly Tyr Thr Phe Ala Ser Tyr
             20                  25                  30

Trp Ile Asn Trp Val Lys Gln Arg Pro Gly Gln Gly Leu Glu Trp Ile
         35                  40                  45

Gly His Ile Tyr Pro Val Arg Ser Ile Thr Lys Tyr Asn Glu Lys Phe
 50                  55                  60

Lys Ser Lys Ala Thr Leu Thr Leu Asp Thr Ser Ser Thr Ala Tyr
 65                  70                  75                  80

Met Gln Leu Ser Ser Leu Thr Ser Glu Asp Ser Ala Val Tyr Tyr Cys
             85                  90                  95

Ser Arg Gly Asp Gly Ser Asp Tyr Tyr Ala Met Asp Tyr Trp Gly Gln
            100                 105                 110

Gly Thr Thr Val Thr Val Ser Ser Gly Gly Gly Ser Asp Ile Glu
        115                 120                 125

Leu Thr Gln Ser Pro Ala Ile Leu Ser Ala Ser Pro Gly Gly Lys Val
130                 135                 140

Thr Met Thr Cys Arg Ala Ser Ser Ser Val Ser Tyr Met His Trp Tyr
145                 150                 155                 160

Gln Gln Lys Pro Gly Ser Ser Pro Lys Pro Trp Ile Tyr Ala Thr Ser
                165                 170                 175

Asn Leu Ala Ser Gly Val Pro Thr Arg Phe Ser Gly Thr Gly Ser Gly
            180                 185                 190

Thr Ser Tyr Ser Leu Thr Ile Ser Arg Val Glu Ala Glu Asp Ala Ala
        195                 200                 205

Thr Tyr Tyr Cys Gln Gln Trp Ser Arg Asn Pro Phe Thr Phe Gly Ser
```

```
             210                 215                 220
Gly Thr Lys Leu Glu Ile Lys Arg Ala Ala Ala Glu Gln Lys Leu Ile
225                 230                 235                 240

Ser Glu Glu Asp Leu Asn
                245
```

(2) INFORMATION FOR SEQ ID NO: 58:

(i) SEQUENCE CHARACTERISTICS:
        (A) LENGTH: 101 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 58:

```
Met Ser Asn Thr Gln Ala Glu Arg Ser Ile Ile Gly Met Ile Asp Met
1               5                   10                  15

Phe His Lys Tyr Thr Arg Arg Asp Asp Lys Ile Asp Lys Pro Ser Leu
                20                  25                  30

Leu Thr Met Met Lys Glu Asn Phe Pro Asn Phe Leu Ser Ala Cys Asp
            35                  40                  45

Lys Lys Gly Thr Asn Tyr Leu Ala Asp Val Phe Glu Lys Lys Asp Lys
50                      55                  60

Asn Glu Asp Lys Lys Ile Asp Phe Ser Glu Phe Leu Ser Leu Leu Gly
65                  70                  75                  80

Asp Ile Ala Thr Asp Tyr His Lys Gln Ser His Gly Ala Ala Pro Cys
                85                  90                  95

Ser Gly Gly Ser Gln
                100
```

ITERATIVE METHOD OF AT LEAST FIVE CYCLES FOR THE REFOLDING OF PROTEINS

This is a divisional of application Ser. No. 08/192,060, filed Feb. 4, 1994 (now abandoned).

FIELD OF THE INVENTION

This invention relates to recombinant DNA technology and, in particular to protein engineering technologies for the production of correctly folded proteins by expression of genes or gene fragments in a host organism, heterologous or homologous, as recombinant protein products, by describing novel general principles and methodology for efficient in vitro refolding of misfolded and/or insoluble proteins, including proteins containing disulphide bonds. This invention further relates to the refolding of unfolded or misfolded polypeptides of any other origin. The invention also relates to novel designs of encrypted recognition sites for factor $X_a$ cleavage of chimeric proteins, sites that only become recognized after in vitro derivatization. Two analogues of bovine coagulation factor $X_a$, suitable for small-, medium-, or large-scale technological applications involving specific cleavage of chimeric proteins at sites designed for cleavage by factor $X_a$ are provided, too. Finally the invention relates to designs of reversible disulphide-blocking reagents, useful as auxiliary compounds for refolding of cysteine-containing proteins, including a general array procedure by which such disulphide exchange reagents can be evaluated for suitability for this specific purpose.

GENERAL BACKGROUND OF THE INVENTION

Technologies for the production of virtually any polypeptide by introduction, by recombinant DNA methods, of a natural or synthetic DNA fragment coding for this particular polypeptide into a suitable host have been under intense development over the past fifteen years, and are at present essential tools for biochemical research and for a number of industrial processes for production of high-grade protein products for biomedical or other industrial use.

Four fundamental properties of biological systems render heterologous production of proteins possible:

(i) The functional properties of a protein are entirely specified by its three-dimensional structure, and, due to the molecular environment in the structure, manifested by chemical properties exhibited by specific parts of this structure.

(ii) The three-dimensional structure of a protein is, in turn, specified by the sequence information represented by the specific sequential arrangement of amino acid residues in the linear polypeptide chain(s). The structure information embedded in the amino acid sequence of a polypeptide is by itself sufficient, under proper conditions, to direct the folding process, of which the end product is the completely and correctly folded protein.

(iii) The linear sequence of amino acid residues in the polypeptide chain is specified by the nucleotide sequence in the coding region of the genetic material directing the assembly of the polypeptide chain by the cellular machinery. The translation table governing translation of nucleic acid sequence information into amino acid sequence is known and is almost universal among known organisms and hence allows nucleic acid segments coding for any polypeptide segment to direct assembly of polypeptide product across virtually any cross-species barrier.

(iv) Each type of organism relies on its own characteristic array of genetic elements present within its own genes to interact with the molecular machinery of the cell, which in response to specific intracellular and extracellular factors regulates the expression of a given gene in terms of transcription and translation.

In order to exploit the protein synthesis machinery of a host cell or organism to achieve substantial production of a desired recombinant protein product, it is therefore necessary to present the DNA-segment coding for the desired product to the cell fused to control sequences recognized by the genetic control system of the cell.

The immediate fate of a polypeptide expressed in a host is influenced by the nature of the polypeptide, the nature of the host, and possible host organism stress states invoked during production of a given polypeptide. A gene product expressed in a moderate level and similar or identical to a protein normally present in the host cell, will often undergo normal processing and accumulation in the appropriate cellular compartment or secretion, whichever is the natural fate of this endogenous gene product. In contrast, a recombinant gene product which is foreign to the cell or is produced at high levels often activates cellular defence mechanisms similar to those activated by heat shock or exposure to toxic amino acid analogues, pathways that have been designed by nature to help the cell to get rid of "wrong" polypeptide material by controlled intracellular proteolysis or by segregation of unwanted polypeptide material into storage particles ("inclusion bodies"). The recombinant protein in these storage particles is often deposited in a misfolded and aggregated state, in which case it becomes necessary to dissolve the product under denaturing and reducing conditions and then fold the recombinant polypeptide by in vitro methods to obtain a useful protein product.

Expression of eukaryotic genes in eukaryotic cells often allows the direct isolation of the correctly folded and processed gene product from cell culture fluids or from cellular material. This approach is often used to obtain relatively small amounts of a protein for biochemical studies and is presently also exploited industrially for production of a number of biomedical products. However, eukaryotic expression technology is expensive in terms of technological complexity, labour- and material costs. Moreover, the time scale of the development phase required to establish an expression system is at least several months, even for laboratory scale production. The nature and extent of post-translational modification of the recombinant product often differs from that of the natural product because such modifications are under indirect genetic control in the host cell. Sequence signals invoking a post-synthetic modification are often mutually recognized among eukaryotes, but availability of the appropriate suite of modification enzymes is given by the nature and state of the host cell.

A variety of strategies have been developed for expression of gene products in prokaryotic hosts, advantageous over eukaryotic hosts in terms of capital, labour and material requirements. Strains of the eubacteria *Escherichia coli* are often preferred as host cells because *E. coli* is far better characterized genetically than any other organism, also as the molecular level.

Prokaryotic host cells do not possess the enzymatic machinery required to carry out post-translational modification, and an eukaryotic gene product will therefore necessarily be produced in its unmodified form. Moreover, the product must be synthesized with an N-terminal extension, at least one additional methionine residue arising from the required translation initiation codon, more often also including an N-terminal segment corresponding to that of a highly expressed host protein. General methods to remove such N-terminal extensions by sequence specific proteolysis at linker segments inserted at the junction between the N-terminal extension and the desired polypeptide product have been described (Enterokinase-cleavable linker sequence: EP 035384, The Regents of the University of California; Factor $X_a$-cleavable linker sequence: EP 161937, Nagai & Thøgersen, Assignee: Celltech Ltd.).

Over the years a considerable effort has been directed at the development of strategies for heterologous expression in prokaryotes to generate recombinant protein products in a soluble form or fusion protein constructs that allow secretion from the cell in an active, possibly N-terminally processed form, an effort resulting in limited success only, despite recent developments in the chaperone field. Typically, much time and effort is required to develop and modify an expression system before even a small amount of soluble and correctly folded fusion protein product can be isolated. More often all of the polypeptide product is deposited within the host cell in an improperly folded state in "inclusion bodies". This is particularly true when expression eukaryotic proteins containing disulphide bridges.

Available methods for in vitro refolding of proteins all describe processes in which the protein in solution or non-specifically adsorbed to ion exchange resins etc. is exposed to solvent, the composition of which is gradually changed over time from strongly denaturing (and possibly reducing) to non-denaturing in a single pass. This is often carried out by diluting a concentrated solution of protein containing 6–8 M guanidine hydrochloride or urea into a substantial volume of non-denaturing buffer, or by dialysis of a dilute solution of the protein in the denaturing buffer against the non-denaturing buffer. Numerous variants of this basic procedure have been described, including addition of specific ligands or cofactors of the active protein and incorporation of polymer substances like poly ethylene oxide (polyethylene glycol), thought to stabilize the folded structure.

Although efficient variants of the standard in vitro refolding procedure have been found for a number of specific protein products, including proteins containing one or more disulphide bonds, refolding yields are more often poor, and scale-up is impractical and expensive due to the low solubility of most incompletely folded proteins which implies the use of excessive volumes of solvent.

The common characteristic of all traditional in vitro refolding protocols is that refolding induced by sudden or gradual reduction of denaturant is carried out as a single-pass operation, the yield of which is then regarded as the best obtainable for the protein in question.

The general field of protein folding has been summarized in a recent text book edited by Thomas W. Creighton ("Protein folding", ed. Creighton T. E., Freeman 1992) and a more specific review of practical methods for protein refolding was published in 1989 by Rainer Jaenicke & Rainer Rudolph (p. 191 223 in, "Protein Structure, a practical approach", ed. T. E. Creighton, IRL Press 1989). Among the numerous more detailed publications, state-of-the-art reviews like those by Schein (Schein C. H., 1990, Bio/Technology 8, 308–317) or Buchner and Rudolph (Buchner J. and Rudolph R., 1991 Bio/Technology 9, 157–162) may be consulted.

In conclusion, there is a definite need for generally applicable high-yield methods for the refolding of un- or misfolded proteins derived from various sources, such as prokaryotic expression systems or peptide synthesis.

SUMMARY OF THE INVENTION

It has been found by the inventors that refolding yields can be greatly increased by taking into account that the protein folding process is a kinetically controlled process and that interconversion between folded, unfolded and misfolded conformers of the protein are subject to hysteresis and lime-dependent phenomena that can be exploited to design a cyclic denaturation-renaturation process, in which refolded protein product accumulates incrementally in each cycle at the expense of unfolded and misfolded conformers, to generate a new refolding process of much greater potential than the basic traditional approach.

By the term "folded protein" is meant a polypeptide in (a) conformational state(s) corresponding to that or those occurring in the protein in its biologically active form or unique stable intermediates that in subsequent steps may be converted to generate the biologically active species. The covalent structure of the folded protein in terms of crosslinking between pairs of cysteine residues in the polypeptide is identical to that of the protein in its biologically active form.

Accordingly, the term "unfolded protein" refers to a polypeptide in conformational states less compact and well-defined than that or those corresponding to the protein in its biologically active, hence folded, form. The covalent structure of the unfolded protein in terms of crosslinking between pairs of cysteine residues in the polypeptide may or may not be identical to that of the protein in its biologically active form. Closely related to an unfolded protein is a "misfolded protein" which is a polypeptide in a conformational state which is virtually thermodynamically stable, sometimes even more so than that or those states corresponding to the protein in its folded form, but which does not exhibit the same degree, if any, of the biological activity of the folded protein. As is the case for the unfolded protein, the covalent structure in terms of crosslinking between pairs of cysteine residues in the polypeptide may or may not be the same as that of the folded protein.

By the term "refolded protein" is meant a polypeptide which has been converted from an unfolded state to attain its biologically active conformation and covalent structure in terms of crosslinking between correct pairs of cysteine residues in the polypeptide.

The new generally applicable protein refolding strategy has been designed on the basis of the following general properties of protein structure.

(a) The low solubility of unfolded proteins exposed to non-denaturing solvents reflects a major driving force inducing the polypeptide either to form the compact correctly refolded structure or to misfold and generate dead-end aggregates or precipitates, which are unable to refold and generate the correctly refolded structure under non-denaturing conditions within a reasonable amount of time.

(b) A newly formed dead-end aggregate is more easily "denatured" i.e. converted into an unfolded form than the correctly refolded protein because the structure of the dead-end aggregate is more disordered. Probably misfolding is also in general a kinetically controlled process.

(c) An unfolded protein is often not (or only very slowly) able to refold into the correctly refolded form at denaturant levels required to denature dead end aggregates within a reasonable amount of time.

(d) The body of evidence available to support (b) includes detailed studies of folding and unfolding pathways and intermediates for several model proteins. Also illustrative is the observation made for many disulphide bonded proteins that the stability of disulphide bonds against reduction at limiting concentrations of reducing and denaturing agents is often significantly different for each disulphide bridge of a given protein, and that the disulphide bridges in the folded protein are in general much less prone to reduction or disulphide exchange than "non-active" disulphide bonds in a denatured protein or protein aggregate.

The new strategy for a refolding procedure is most easily illustrated by way of the following theoretical example:

Consider a hypothetical protein—stably folded in a non-denaturing buffer "A" and stably unfolded in the strongly denaturing buffer "B" (being e.g. a buffer containing 6 M guanidine-HCl)—exposed to buffer A or to buffer B and then subjected to incubation at intermediate levels of denaturation in mixtures of buffers A and B.

Levels between e.g. 100 to 75% B lead to conversion of both folded protein and dead-end aggregated protein to the unfolded form within a short period of time.

Levels between e.g. 75–50% B lead to conversion of newly formed dead-end aggregate to the unfolded form, whereas almost all refolded protein remains in a native-like structure, stable at least within a period of time of hours, from which it may snap back into the refolded form upon removal of the denaturant.

Levels in excess of 10% B prevent rapid formation of refolded form from unfolded form.

A solvent composition step from 100% B to 0% B converts unfolded protein to dead-end aggregate (75% yield) and refolded protein (25% yield).

Let us now subject a sample of this protein, initially in its unfolded form in 100% B, to a time-series of programmed denaturation-renaturation cycles as illustrated in FIG. 1, each consisting of a renaturation phase ($F_n$) (<10% B) and a denaturation phase ($D_n$). At the end of the renaturation phase of cycle(i) the denaturant content is changed to a level, $k_i$ % less than the denaturant level of the previous cycle. Following a brief incubation the denaturant is again removed, and the next renaturation phase $F_{i+1}$ entered. Assuming the denaturation level starts out at 100% B and $k_i$ for each cycle is fixed at 4%, this recipe will generate a damped series of "denaturation steps" dying out after 25 cycles.

Through 25 cycles, as outlined above, the accumulation of refolded protein would progress as follows:

In cycles 1 to 5 all of the protein, folded as well as misfolded will become unfolded in each of the denaturation phases $D_n$.

Cycles 7 through 12: Dead-end aggregates will be converted to unfolded protein in each step whereas protein recoverable as refolded product will accumulate in the following amounts, cycle by cycle: 25%, 44%, 58%, 68%, 76% and 82%.

No further conversions take place through cycles 13 to 25.

The cyclic refolding process would therefore produce a total refolding yield of over 80%, whereas traditional one-pass renaturation at best would produce a yield of 25%.

It will be appreciated that a great number of simplifying approximations in terms of all-or-none graduation at each characteristic of the various conformational states of the hypothetical protein have been made. The basic working principle, nevertheless, remains similar if a more complicated set of presumptions are incorporated in the model.

Arranging a practical setup for establishing a cyclic denaturation/renaturation protein refolding process can be envisaged in many ways.

The protein in solution could e.g. be held in an ultrafiltration device, held in a dialysis device or be confined to one of the phases of a suitable aqueous two-phase system, all of which might allow the concentration of low-molecular weight chemical solutes in the protein solution to be controlled by suitable devices.

Alternatively, the protein could be adsorbed to a suitable surface in contact with a liquid phase, the chemical composition of which could be controlled as required. A suitable surface could e.g. be a filtration device, a hollow-fibre device or a beaded chromatographic medium. Adsorption of the protein to the surface could be mediated by non-specific interactions, e.g. as described in WO 86/05809 (Thomas Edwin Creighton), by folding-compatible covalent bonds between surface and protein or via specific designs of affinity handles in a recombinant derivative of the protein exhibiting a specific and denaturation-resistant affinity for a suitable derivatized surface.

The specific implementation of the cyclic denaturation/renaturation protein refolding process established to investigate the potential of the general method was based on a design of cleavable hybrid proteins (EP 161937, Nagai & Thøgersen, Assignee: Celltech Ltd.) containing a metal affinity handle module (EP 0282042 (Heinz Döbeli, Bernhard Eggimann, Reiner Gentz, Erich Hochuli; Hoffman-La Roehe)) inserted N-terminally to the designed factor $X_a$ cleavage site. Recombinant proteins of this general design, adsorbed on Nickel-chelating agarose beads could then be subjected to the present cyclic refolding process in a chromatographic column "refolding reactor" perfused with a mixture of suitable denaturing and non-denaturing buffers, delivered by an array of calibrated pumps, the flow rates of which was time-programmed through computer control.

A general scheme of solid-stage refolding entails cycling the immobilized protein as outlined above or by any other means and implementations between denaturing and non-denaturing conditions in a progressive manner, in which the concentration of the denaturing agent is gradually reduced from high starting values towards zero over a train of many renaturation-denaturation cycles. Using this approach it is not necessary to determine precisely which limiting denaturant concentration is required to obtain folding yield enrichment in the course of cycling of the specific protein at hand, because the progressive train of cycles will go through (up to) three phases, an early phase in which folded product present at the end of cycle (i) is completely denatured at the denaturation step of cycle (i+1), an intermediate productive phase during which refolded protein accumulates in increasing quantity, and a late phase during which the concentration of denaturant is too low to perturb the refolded protein or any remaining misfolded structures. Subjecting the protein to a progressing series of denaturation-renaturation cycles as outlined will therefore include several productive cycles.

For disulphide-containing proteins progressive denaturation-renaturation cycling may be enhanced by using equipment similar to advanced chromatography equipment with on-line facilities to monitor buffer compositions of folding reactor effluent. Information on effluent composition with regard to reductant and disulphide reshuffling reagent concentration profile would reveal productive cycling, and could therefore be used as input to an intelligent processor unit, in turn regulating the progression of denaturant concentration in a feed-back loop to ensure that most of the cycling effort is spent within the productive phase of the denaturation-renaturation cycle train. Such auto-optimization of cycling conditions would be possible because the analytical system may be used to measure extent and direction of changes in redox equilibrium in the buffer stream, measurements that directly reflect titration of thiol-groups/disulphide equivalents in the immobilized protein sample, and is therefore directly translatable into average number of disulphide bonds being disrupted or formed during the various phases of a cycle.

Other possible inputs for the intelligent processor controlling the progression of cycling include measurements of ligand-binding, substrate conversion, antibody binding ability and, indeed, any other interacting soluble agent interacting in distinct ways with misfolded and folded protein, which in the assessing stage of folding measurement might be percolated through the refolding reactor and then in-line monitored in the effluent by suitable analytical devices.

An intelligent monitoring and control system could furthermore use the available information to direct usable portions of reactor effluent to salvage/recycling subsystems thereby minimizing expenses for large scale operations.

After execution of the folding procedure the final product may be eluted from the affinity matrix in a concentrated form, processed to liberate the mature authentic protein by cleavage at the designed protease cleavage site and then subjected to final work-up using standard protein purification and handling techniques, well-known within the field of protein chemistry.

DETAILED DISCLOSURE OF THE INVENTION

Thus, the present invention relates to a method for generating a processed ensemble of polypeptide molecules, in which processed ensemble the conformational states represented contain a substantial fraction of polypeptide molecules in one particular uniform conformation, from an initial ensemble of polypeptide molecules which have the same amino acid sequence as the processed ensemble of polypeptide molecules, comprising subjecting the initial ensemble of polypeptide molecules to a series of at least two successive cycles each of which comprises a sequence of 1) at least one denaturing step involving conditions exerting a denaturing influence on the polypeptide molecules of the ensemble followed by 2) at least one renaturing step involving conditions having a renaturing influence on the polypeptide molecules having conformations resulting from the preceding step.

In the present specification and claims, the term "ensemble" is used in the meaning it has acquired in the art, that is, it designates a collection of molecules having essential common features. Initially ("an initial ensemble"), they have at least their amino acid sequence in common (and of course retain this common feature). When the ensemble of polypeptide molecules has been treated in the method of the invention (to result in "a processed ensemble"), the conformational states represented in the ensemble will contain a substantial fraction of polypeptide molecules with one particular conformation. As will be understood from the discussion which follows, the substantial fraction of polypeptide molecules with one particular conformation in the processed ensemble may vary dependent on the parameters of the treatment by the method of the invention, the size of the protein in the particular conformation, the length and identity of the amino acid sequence of the molecules, etc. In the examples reported herein, in which the process parameters have not yet been optimized, the fraction of polypeptide molecules with one particular conformation varied between 15% and 100% of the ensemble, which in all cases is above what could be obtained prior to the present invention. In example 13 it is further demonstrated that purification of the polypeptide molecules prior to their subjection to the method of the invention increases the fraction of polypeptide molecules with one particular conformation.

"Denaturing step" refers to exposure of an ensemble of polypeptide molecules during a time interval to physical and/or chemical circumstances which subject the ensemble of polypeptide molecules to conditions characterized by more severe denaturing power than those characterizing conditions immediately prior to the denaturing step.

Accordingly, the term "renaturing step" refers to exposure of an ensemble of polypeptide molecules during a time interval to physical and/or chemical circumstances which subject the ensemble of polypeptide molecules to conditions characterized by less severe denaturing power than those characterizing conditions immediately prior to the denaturing step.

It will be understood, that the "substantial fraction" mentioned above will depend in magnitude on the ensemble of polypeptide molecules which are subjected to the method of the invention. If the processed ensemble of polypeptides consists of monomeric proteins of relatively short lengths and without intramolecular disulphide bridges the method will in general result in very high yields, whereas complicated molecules (such as polymeric proteins with a complicated disulphide bridging topology) may result in lower yields, even if the conditions of the method of the invention are fully optimized.

An interesting aspect of the invention relates to a method described above wherein the processed ensemble comprises a substantial fraction of polypeptide molecules in one conformational state the substantial fraction constituting at least 1% (w/w) of the initial ensemble of polypeptide molecules. Higher yields are preferred, such as at least 5%, at least 10%, at least 20%, and at least 25% of the initial ensemble of polypeptide molecules. More preferred are yields of at least 30%, such as at least 40%, 50%, 60%, 70%, and at least 80%. Especially preferred are yields of at least 85%, such as 90%, 95%, 97%, and even at 99%. Sometimes yields close to 100% are observed.

When the polypeptide molecules of the ensemble contain cysteine, the processed ensemble will comprise a substantial fraction of polypeptide molecules in one particular uniform conformation which in addition have substantially identical disulphide bridging topology.

In most cases, the polypeptide molecules subjected to the method of the invention will be molecules which have an amino acid sequence identical to that of an authentic polypeptide, or molecules which comprise an amino acid sequence corresponding to that of an authentic polypeptide joined to one or two additional polypeptide segments.

By the term "authentic protein or polypeptide" is meant a polypeptide with primary structure, including N- and C-terminal structures, identical to that of the corresponding natural protein. The term also denotes a polypeptide which has a known primary structure which is not necessarily identical to that of a natural protein, which polypeptide is the intentional end-product of a protein synthesis.

By the term "natural protein" is meant a protein as isolated in biologically active form from an organism, in which it is present not as a consequence of genetic manipulation.

In contrast, the term "artificial protein or polypeptide" as used in the present specification and claims is intended to relate to a protein/polypeptide which is not available from any natural sources, i.e. it cannot be isolated and purified from any natural source. An artificial protein/polypeptide is thus the result of human intervention, and may for instance be a product of recombinant DNA manipulation or a form of an in vitro peptide synthesis. According to the above definitions such an artificial protein may be an authentic protein, but not a natural protein.

Thus, the invention also relates to a method wherein natural proteins as well as artificial proteins are subjected to the refolding processes described herein.

As will be explained in greater detail below, it may be advantageous for various reasons that the authentic polypeptide is joined to polypeptide segments having auxiliary functions during the cycling and other previous or subsequent processing, e.g. as "handles" for binding the polypeptide to a carrier, as solubility modifiers, as expression boosters which have exerted their beneficial function during translation of messenger RNA, etc. Such an auxiliary polypeptide segment will preferably be linked to the authentic polypeptide via a cleavable junction, and where two such auxiliary polypeptide segments are linked to the authentic polypeptide, this may be via similar cleavable junctions which will normally be cleaved simultaneously, or through dissimilar cleavable junctions which may be cleaved in any time sequence.

In accordance with what is explained above, it is believed to be a major novel characteristic feature of the present invention that the cycling (which, as explained above, comprises at least two successive cycles) will give rise to at least one event where a renaturing step is succeeded by a denaturing step where at least a substantial fraction of the refolded polypeptides will be denatured again.

In most cases, the processing will comprise at least 3 cycles, often at least 5 cycles and more often at least 8 cycles, such as at least 10 cycles and, in some cases at least 25 cycles. On the other hand, the series of cycles will normally not exceed 2000 cycles and will often comprise at most 1000 cycles and more often at most 500 cycles. The number of cycles used will depend partly on the possibilities made available by the equipment in which the cycling is performed.

Thus, if the cycling treatment is performed with the polypeptide molecules immobilized to a carrier column, such as will be explained in greater detail below, the rate with which the liquid phase in contact with the column can be exchanged will constitute one limit to what can realistically be achieved. On the other hand, high performance liquid chromatography (HPLC) equipment will permit very fast exchange of the liquid environment and thus make cycle numbers in the range of hundreds or thousands realistic.

Other consideration determining the desirable number of cycles are e.g., inherent kinetic parameters such as interconversion between cis and trans isomers at proline residues which will tend to complicate redistribution over the partially folded states and will thus normally require due consideration of timing. Another time-critical characteristic resides in the kinetics of disulphide reshuffling (cf. the discussion below of disulphide-reshuffling systems).

With due consideration of the above, the cycling series will often comprise at most 200 cycles, more often at most 100 cycles and yet more often at most 50 cycles.

In accordance with what is stated above, the duration of each denaturing step may be a duration which, under the particular conditions in question, is at least one milli-second and at most one hour, and the duration of each renaturing step may be a duration which, under the particular conditions in question, is at least 1 second and at most 12 hours.

In most embodiments of the method, the denaturing conditions of each individual denaturing step are kept substantially constant for a period of time, and the renaturing conditions of each individual renaturing step are kept substantially constant for a period of time, the period of time during which conditions are kept substantially constant being separated by transition period during which the conditions are changed. The transition period between steps for which conditions are kept substantially constant may have a duration varying over a broad range, such as between 0.1 second and 12 hours and will normally be closely adapted to the durations of the denaturing and renaturing steps proper.

Bearing this in mind, the period of time for which the denaturing conditions of a denaturing step are kept substantially constant may, e.g. have a duration of at least one millisecond and at most one hour, often at most 30 minutes, and the period of time for which the renaturing conditions of a renaturing step are kept substantially constant has a duration of at least 1 second and at most 12 hours, and often at most 2 hours.

In practice, the period of time for which the denaturing conditions of a denaturing step are kept substantially constant will often have a duration of between 1 and 10 minutes, and the period of time for which the renaturing conditions of a renaturing step are kept substantially constant will often have a duration of between 1 and 45 minutes.

It will be understood from the above, that adjustments should be made to the intervals stated above, taking into consideration the change of kinetics resulting from the change in physical conditions to which the polypeptides are subjected. For instance, the pressure may be very high (up to 5000 Bar) when using an HPLC system when performing the method of the invention, and under such circumstances very rapid steps may be accomplished and/or necessary. Further, as can be seen from the examples, the temperature parameter is of importance, as some proteins only will refold properly at temperatures far from the physiological range. Both temperature and pressure will of course have an effect on the kinetics of the refolding procedure of the invention, and therefore the above-indicated time intervals of renaturing and denaturing steps are realistic boundaries for the many possible embodiments of the invention.

For a given utilization of the method of the invention, the skilled person will be able to determine suitable conditions based, e.g., on preliminary experiments.

As indicated above, the polypeptide molecules are normally in contact with a liquid phase during the denaturing and renaturing steps, the liquid phase normally being an aqueous phase. This means that any reagents or auxiliary substances used in the method will normally be dissolved in the liquid phase, normally in an aqueous phase. However, if convenient, the liquid phase may also be constituted by one or more organic solvents.

In connection with renaturing of proteins, it is well known to use a so-called "chaperone" or "chaperone complex". Chaperones are a group of recently described proteins that show a common feature in their capability of enhancing refolding of unfolded or partly unfolded proteins. Often, the chaperones are multimolecular complexes. Many of these chaperones are heat-shock proteins, which means that in vivo, they are serving as factors doing post traumatic "repair" on proteins that have been destabilized by the trauma. To be able to fulfil this function, chaperones tend to be more stable to traumatic events than many other proteins and protein complexes. While the method of the invention does not depend on the use of a molecular chaperone or a molecular chaperone complex, it is, of course, possible to have a suitable molecular chaperone or molecular chaperone complex present during at least one renaturing step, and it may be preferred to have a molecular chaperone or a molecular chaperone complex present during substantially all cycles.

As mentioned above, the polypeptide molecules are preferably substantially confined to an environment which allows changing or exchanging the liquid phase substantially without entraining the polypeptide molecules. This can be achieved in a number of ways. For instance, the polypeptide molecules may be contained in a dialysis device, or they may be confined to one of the phases of a suitable liquid two-phase system. Such a suitable aqueous two phase system may, e.g., contain a polymer selected from the group consisting of polyethylene oxide (polyethylene glycol), polyvinyl acetate, dextran and dextran sulphate. In one interesting setup, one phase contains polyethylene oxide (polyethylene glycol) and the other phase contains dextran, whereby the polypeptide molecules will be confined to the dextran-containing phase.

Another way of avoiding entraining the polypeptide by having the polypeptide molecules bound to a solid or semi-solid carrier, such as a filter surface, a hollow fibre or a beaded chromatographic medium, e.g. an agarose or polyacrylamide gel, a fibrous cellulose matrix or an HPLC or FPLC (Fast Performance Liquid Chromatography) matrix. As another measure, the carrier may be a substance having molecules of such a size that the molecules with the polypeptide molecules bound thereto, when dissolved or dispersed in a liquid phase, can be retained by means of a filter, or the carrier may be a substance capable of forming micelles or participating in the formation of micelles allowing the liquid phase to be changed or exchanged substantially without entraining the micelles. In cases where the micelle-forming components would tend to escape from the system as monomers, e.g. where they would be able to some extent to pass an ultrafilter used in confining the system, this could be compensated for by replenishment with additional micelle-forming monomers.

The carrier may also be a water-soluble polymer having molecules of a size which will substantially not be able to pass through the pores of a filter or other means used in confining the system.

The polypeptide molecules are suitable non-covalently adsorbed to the carrier through a moiety having affinity to a component of the carrier. Such a moiety may, e.g., be a biotin group or an analogue thereof bound to an amino acid moiety of the polypeptide, the carrier having avidin, streptavidin or analogues thereof attached thereto so as to establish a system with a strong affinity between the thus modified polypeptide molecules and the thus modified carrier. It will be understood that the affinity between the modified polypeptide and the modified carrier should be sufficiently stable so that the adsorption will be substantially unaffected by the denaturing conditions; the removal of the polypeptide molecules from the carrier after the cycling should be performed using specific cleaving, such as is explained in the following.

An example of a suitable amino acid residue to which a biotinyl group may be bound is lysine.

One interesting way of introducing an amino acid carrying a moiety having affinity to the carrier is CPY synthesis. CPY (carboxy peptidase Y) is known to be capable of adding amino acid amide irrespective of the nature of the side chain of that amino acid amide.

In an interesting embodiment, the moiety having affinity to the carrier is the polypeptide segment SEQ ID NO: 47, in which case the carrier suitably comprises a Nitrilotriacetic Acid derivative (NTA) charged with $Ni^{++}$ ions, for instance an NTA-agarose matrix which has been bathed in a solution comprising $Ni^{++}$.

An important aspect of the invention relates to the presence of suitable means in the polypeptide molecule preparing the molecule for later cleavage into two or more segments, wherein one segment is an authentic polypeptide as defined above. Such combined polypeptide molecule (fusion polypeptide molecules) may for this purpose comprise a polypeptide segment which is capable of directing preferential cleavage by a cleaving agent at a specific peptide bond. The polypeptide segment in question may be one which directs the cleavage as a result of the conformation of the segment which serves as a recognition site for the cleaving agent.

The cleavage directing polypeptide segment may for instance be capable of directing preferential cleavage at a specific peptide bond by a cleaving agent selected from the group consisting of cyanogen bromide, hydroxylamine, iodosobenzoic acid and N-bromosuccinimide.

The cleavage-directing polypeptide segment may be one which is capable of directing preferential cleavage at a specific peptide bond by a cleaving agent which is an enzyme and one such possible enzyme is bovine enterokinase or an analogue and/or homologue thereof.

In an important aspect of the invention, the cleaving agent is the enzyme bovine coagulation factor $X_a$ or an analogue and/or homologue thereof (such analogues will be discussed in greater detail further below), and the polypeptide segment which directs preferential cleavage is a sequence which is substantially selectively recognized by the bovine coagulation factor $X_a$ or an analogue and/or homologue thereof. Important such segments from the group consisting of SEQ ID NO: 38, SEQ ID NO: 40, SEQ ID NO: 41 and SEQ ID NO: 42.

An interesting feature of the invention is the possibility of masking and unmasking polypeptide segments with respect to their ability to direct cleavage at a specific peptide bond, whereby it is obtained that different segments of the polypeptide can be cleaved at different stages in the cycles.

Thus, when the polypeptide molecules comprise a polypeptide segment which is in vitro-convertible into a derivatized polypeptide segment capable of directing preferential cleavage by a cleaving agent at a specific peptide bond, a masking/unmasking effect as mentioned becomes available. An especially interesting version of this strategy is where the in vitro-convertible polypeptide segment is convertible into a derivatized polypeptide segment which is substantially selectively recognized by the bovine coagulation factor $X_a$ or an analogue and/or homologue thereof.

It is contemplated that both cysteine and methionine residues can be converted into modified residues, which modified residues make the segments having amino acid sequences selected from the group consisting of SEQ ID NO: 43, SEQ ID NO: 11, SEQ ID NO: 45 and SEQ ID NO: 46 in vitro converted into segments recognized by bovine coagulation factor $X_a$ or an analogue and/or homologue thereof.

According to the invention, one possible solution involving the cysteine residue is that a polypeptide segment with the amino acid sequence SEQ ID NO: 43 or SEQ ID NO: 44, is converted into a derivatized polypeptide which is substantially selectively recognized by bovine coagulation factor $X_a$, by reacting the cysteine residue with N (2-mercaptoethyl)morpholyl-2-thiopyridyl disulphide or mercaptothioacetate-2-thiopyridyl disulphide.

A possible strategy according to the invention involving methionine is that a polypeptide segment with the amino acid sequence SEQ ID NO: 45 or SEQ ID NO: 46, is converted into a derivatized polypeptide, which is substantially selectively recognized by bovine coagulation factor $X_a$, by oxidation of the thioether moiety in the methionine side group to a sulphoxide or sulphone derivative.

Preferred embodiments of the method according to the invention are those wherein the cleavage-directing segments with the amino acid sequences SEQ ID NO: 38, SEQ ID NO: 40, SEQ ID NO: 41 or SEQ ID NO: 42, or the masked cleavage-directing segments with the amino acid sequences SEQ ID NO: 43, SEQ ID NO: 44, SEQ ID NO: 45 and SEQ ID NO: 46 are linked N-terminally to the authentic polypeptide, because then no further processing other than the selective cleaving is necessary in order to obtain the authentic polypeptide in solution. On the other hand, one possible reason for linking the cleavage directing sequences at the C-terminal end of the authentic polypeptide would be that the correct folding of the polypeptide molecules is dependent on a free N-terminal of the polypeptide molecules. In such a case, the part of the cleaving directing sequence remaining after cleaving can be removed by suitable use of carboxypeptidases A and B.

The change of conditions during the transition period between the steps may according to the invention be accomplished by changing the chemical composition of the liquid phase with which the polypeptide molecules are in contact. Thus, denaturing of the polypeptide molecules may be accomplished by contacting the polypeptide molecules with a liquid phase in which at least one denaturing compound is dissolved, and renaturing of the polypeptide molecules is accomplished by contacting the polypeptide molecules with a liquid phase which either contains at least one dissolved denaturing compound in such a concentration that the contact with the liquid phase will tend to renature rather than denature the ensemble of polypeptide molecules in their respective conformation states resulting from the preceeding step, or contains substantially no denaturing compound.

The expression "denaturing compound" refers to a compound which when present as one of the solutes in a liquid phase comprising polypeptide molecules may destabilize folded states of the polypeptide molecules leading to partial or complete unfolding of the polypeptide chains. The denaturing effect exerted by a denaturing compound increases with increasing concentration of the denaturing compound in the solution, but may furthermore be enhanced or moderated due to the presence of other solutes in the solution, or by changes in physical parameters, e.g. temperature of pressure.

As examples of suitable denaturing compounds to be used in the method according to the invention may be mentioned urea, guanidine-HCl, di-$C_{1-6}$alkylformamides such as dimethylformamide and di-$C_{1-6}$-alkylsulphones.

The liquid phase used in at least one of the denaturing steps and/or in a least one of the renaturing steps may according to the invention contain a least one disulphide-reshuffling system.

"Disulphide reshuffling systems" are redox systems which contain mixtures of reducing and oxidating agents, the presence of which facilitate the breaking and making of disulphide bonds in a polypeptide or between polypeptides. Accordingly, "disulphide reshuffling agents" or "disulphide reshuffling compounds" are such reducing and oxidating agents which facilitate the breaking and making of disulphide bonds in a polypeptide or between polypeptides. In an important aspect of the invention, the disulphide-reshuffling system contained in the aqueous phase which is in contact with the proteins comprises as a disulphide reshuffling system a mixture of a mercaptan and its corresponding disulphide compound.

As an example, all cysteine residues in the polypeptide molecules may have been converted to mixed disulphide products of either glutathione, thiocholine, mercaptoethanol or mercaptoacetic acid, during at least one of the denaturing/renaturing cycles. Such a converted polypeptide is termed a "fully disulphide-blocked polypeptide or protein" and this term thus refers to a polypeptide or a protein in which cysteine residues have been converted to a mixed-disulphide in which each cysteine residues is disulphide-linked to a mercaptan, e.g. glutathione. The conversion of the cysteine residues to mixed disulphide products may be accomplished by reacting a fully denatured and fully reduced ensemble of polypeptide molecules with an excess of a reagent which is a high-energy mixed disulphide compounds, such as aliphatic-aromatic disulphide compounds, e.g. 2 thiopyridyl glutathionyl disulphide, or by any other suitable method.

As examples of high-energy mixed disulphides, that is, mixed disulphides having a relatively unstable S—S bond) may be mentioned mixed disulphides having the general formula:

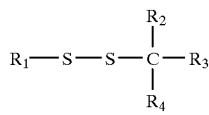

wherein $R_1$ is 2-pyridyl, and each of $R_2$, $R_3$ and $R_4$ is hydrogen or an optionally substituted lower aromatic or aliphatic hydrogen group. Examples of such mixed disulphides are glutathionyl-2-thiopyridyl disulphide, 2 thiocholyl 2-thiopyridyl disulphide, 2-mercaptoethanol-2-thiopyridyl disulphide and mercaptoacetate-2-thiopyridyl disulphide.

In interesting embodiments, the disulphide-reshuffling system contains glutathione, 2-mercaptoethanol or thiocholine, each of which is in admixture with its corresponding symmetrical disulphide.

The suitability of a given mixture of thiols for use as selective reducing and/or disulphide-reshuffling system in a cyclic refolding/reoxidation procedure for a specific protein product can be directly assayed by incubating ensembles of samples of a mixture of folded and misfolded protein with an array of thiol mixtures at several different concentrations of denaturant exerting weakly, intermediate or strongly denaturing effects on the protein. Following incubation, the disulphide topology in each sample is then locked by reaction with an excess of thiol-blocking reagents (e.g. Iodoacetamide) before subjecting each set of samples to SDS-PAGE under non-reducing conditions. Correctly disulphide-bridged material and material in undesired covalent topological states will appear in separate bands and will therefore allow quantitative assessment of folding state of the protein at the time of thiol-blocking, because only correctly unique disulphide-bonded topoisomer may correspond to correctly folded protein present at the end of incubation with thiol/disulphide and denaturant agents. This set of experiments allows identification cation of the range of denaturant levels at which a given thiol/disulphide reagent may be advantageously used as disulphide reshuffling agent, as revealed by preferential reduction and reshuffling of wrong disulphide bonds and low tendency to reduce bonds in the fully folded protein. This reagent testing procedure may be used as a general procedure for selecting advantageous reducing and/or thiol/disulphide reshuffling reagents. Example 12 demonstrates application of this analytical procedure to assess the suitability for selective reduction of misfolded forms of a model protein for 5 thiol reagents and thereby demonstrates the operability of the above procedure.

It will be understood that the above-indicated procedure for selecting suitable disulphide reshuffling systems may also be employed for selecting other compositions than mixtures of thiols. Any mixture containing suitable reducing/oxidating agents may be evaluated according to the above indicated procedure, and the composition of choice in the method of the invention will be the one which shows the highest ability to preferentially reduce incorrectly formed disulphide bridges.

Thus, a very important aspect of the invention is a method for protein refolding as described herein, wherein at least one disulphide-reshuffling system contained in liquid phase in at least one renaturing and/or denaturing step is one which is capable of reducing and/or reshuffling incorrectly formed disulphide bridges under conditions with respect to concentration of the denaturing agent at which unfolded and/or misfolded proteins are denatured and at which there is substantially no reduction and/or reshuffling of correctly formed disulphide bridges.

An interesting embodiment of the invention is a method as described above, wherein a disulphide reshuffling system is used in at least one denaturing/renaturing step and resulting in a ratio between the relative amount of reduced/reshuffled initially incorrectly formed disulphide bridges and the relative amount of reduced/reshuffled initially correctly formed disulphide bridges of at least 1.05. The ratio will preferably be higher, such as 1.1, 1.5, 2.0, 3.0, 5.0, 10, 100, 1000, but even higher ratios are realistic and are thus especially preferred according to the invention.

By the terms "initially incorrectly/correctly" with respect to the form of disulphide bridges is meant the disulphide bridging topology just before the disulphide reshuffling system exerts its effects.

It will be understood that the ratio has to be greater than 1 in order to allow the net formation of correctly formed disulphide bridges in a protein sample. Normally the ratio should be as high as possible, but even ratios which are marginally above 1 will allow the net formation of correctly formed disulphide bridges in the method of the invention, the important parameter in ensuring a high yield being the number of denaturing/renaturing cycles. Ratios just above one require that many cycles are completed before a substantive yield of correctly formed disulphide bridges is achieved, whereas high ratios only require a limited number of cycles.

In cases where only one disulphide reshuffling system is going to be employed such a disulphide-reshuffling system may according to the invention be selected by 1) incubating samples of folded and misfolded protein of the same amino acid sequence as the protein to be processed in the method of the invention with an array of disulphide-reshuffling systems at several different concentrations of a chosen denaturing agent, 2) assessing at each of the different concentrations of denaturing agent the ability of each of the disulphide reshuffling systems to reduce and/or reshuffle initially incorrectly formed disulphide bridges without substantially reducing and/or reshuffling initially correctly formed disulphide bridges as assessed by calculating the ratio between the relative amount of reduced/reshuffled initially incorrectly formed disulphide bridges and the relative amount of reduced/reshuffled initially correctly formed disulphide bridges, and 3) selecting as the disulphide reshuffling system X, the disulphide-reshuffling system which exhibit the capability of reducing initially incorrectly formed disulphide bridges without substantially reducing and/or reshuffling initially correctly formed disulphide bridges in the widest range of concentrations of the chosen denaturing agent.

Alternatively more than one disulphide-reshuffling system may be employed, for instance in different cycles in the cyclic refolding method of the invention, but also simultaneously in the same cycles. This will e.g. be the case when it is likely or has been established by e.g. the method outlined above that the overall yield of correctly folded protein with correct disulphide bridging topology will be higher if using different disulphide-reshuffling systems in the method of the invention.

In order to calculate the above-indicated the ratio between the relative amount of reduced/reshuffled initially incorrectly formed disulphide bridges and the relative amount of reduced/reshuffled initially correctly formed disulphide bridges, the following method may be employed: to the initial mixture of reactants in step 1) is added a known amount of radioactively-labelled correctly folded protein. When the amounts of correctly and incorrectly folded protein are assessed in step 2) (for instance by non-reducing SDS-PAGE) the content of radioactivity in the correctly folded protein fraction is determined as well. Thereby an assessment of the now incorrectly folded (but initially correctly folded) protein can be determined in parallel with the determination of the total distribution of correctly/incorrectly folded protein. The above-mentioned ratio can thus be calculated as $$R = \frac{C_2 - \frac{A_2}{A_1} \cdot C_1}{U_1 \cdot \frac{A_2}{A_1}}$$

wherein $C_1$ and $C_2$ are the initial and the final amounts of correctly folded proteins, respectively, $U_1$ is the amount of initially incorrectly folded protein, and $A_1$ and $A_2$ are the radioactivity in the initial correctly folded protein fraction and in the final correctly folded protein, respectively.

In addition to the denaturing means mentioned above, denaturing may also be achieved or enhanced by decreasing pH of the liquid phase, or by increasing pH of the liquid phase.

The polarity of the liquid phase used in the renaturing may according to the invention have been modified by the addition of a salt, a polymer and/or a hydrofluoro compound such as trifluoroethanol.

According to the invention, the denaturing and renaturing of the polypeptide molecules may also be accomplished by direct changes in physical parameters to which the polypeptide molecules are exposed, such as temperature or pressure, or these measures may be utilized to enhance or moderate the denaturing or renaturing resulting from the other measures mentioned above.

However, it will be understood that a most important practical embodiment of the method is performed by accomplishing chemical changes in the liquid phase by changing between a denaturing solution B and a renaturing solution A. In this case, the concentration of one or more denaturing compounds in B will often be adjusted after each cycle, and as one important example, the concentration of one or more denaturing compounds in B will be decremented after each cycle, but in another important embodiment, the concentration of one or more denaturing compounds in medium B is kept constant in each cycle.

This embodiment of the invention, wherein the concentration of denaturing compound(s) medium B is kept constant, is especially interesting when the most productive phase or the cycling process (with respect to correctly folded protein) has been identified, and large scale production of correctly folded protein is desired. As will be understood, the preferred concentration(s) of denaturing compound(s) of medium B in this embodiment is the concentration(s) which has been established to ensure maximum productivity in the cyclic process according to the invention.

The polypeptide molecules of the ensemble which is subjected to the method of the invention normally have a length of at least 25 amino acid residues, such as at least 30 amino acid residues or at least 50 amino acid residues. On the other hand, the polypeptide molecules of the ensemble normally have a length of at most 5000 amino acid residues, such as at most 2000 amino acid residues or at most 1000 or 800 amino acid residues.

As can be seen from example 10, the method of the invention has made possible the production of correctly folded diabody molecules (diabodies are described in Holliger et al., 1993).

An important aspect of the invention therefore relates to a method for producing correctly folded diabody molecules, wherein an initial ensemble of polypeptide molecules comprising unfolded and/or misfolded polypeptides having amino acid sequences identical to the amino acid sequences of monomer fragments of diabody molecules is subjected to a series of at least two successive cycles, each of which comprises a sequence of 1) at least one denaturing step involving conditions exerting a denaturing influence on the polypeptide molecules of the ensemble followed by 2) at least one renaturing step involving conditions having a renaturing influence on the polypeptide molecules having conformations resulting from the preceding step, the series of cycles being so adapted that a substantial fraction of the initial ensemble of polypeptide molecules is converted to a fraction of correctly folded diabody molecules.

Such a method for the correct folding of diabodies can be envisaged in any of the above-mentioned scenarios and aspects of the refolding method of the invention, that is, with respect to the choice of physical/chemical conditions as well as cycling schedules. However, an important aspect of the method for correct folding of diabodies is a method as the above-identified, wherein the polypeptide molecules are in contact with a liquid phase containing at least one disulphide reshuffling system in at least one denaturing or renaturing step. The preferred denaturing agent to be used in such a liquid phase is urea, and the preferred disulphide reshuffling system comprises glutathione as the main reducing agent.

A particular aspect of the invention relates to a polypeptide which is a proenzyme of a serine protease, but is different from any naturally occurring serine protease and, in particular, has an amino acid sequence different from that of bovine coagulation factor X (Protein Identification Resource (PIR), National Biomedical Research Foundation, Georgetown University, Medical Center, U.S.A., entry: P1;EXBO) and which can be proteolytically activated to generate the active serine protease by incubation of a solution of the polypeptide in a non-denaturing buffer with a substance that cleaves the polypeptide to liberate a new N-terminal residue, the substrate specificity of the serine protease being identical to or better than that of bovine blood coagulation factor $X_a$, as assessed by each of the ratios (k(I)/k(V) and k(III)/k(V)) between cleavage rate against each of the substrates I and III:

T: Benzoyl-Val-Gly-Arg-paranitroanilide,

III: Tosyl-Gly-Pro-Arg-paranitroanilide, versus that against the substrate

V: Benzoyl-Ile-Glu-Gly-Arg-paranitroanilide at 20° C., pH=8 in a buffer consisting of 50 mM Tris, 100 mM NaCl, 1 mM $CaCl_2$, being identical to or lower than the corresponding ratio determined for bovine coagulation factor $X_a$ which is substantially free from contaminating proteases.

The characterization of the above-identified new polypeptides as serine proteases is in accordance with the normal nomenclatural use of the term serine proteases. As is well known in the art, serine proteases are enzymes which are believed to have a catalytic system consisting of an active site serine which is aligned with a histidine residue, and it is believed that the activation of the enzymes from the corresponding proenzymes is based on the liberation of a new N-terminal residue, the α-amino group of which is capable of repositioning within the polypeptide structure for form a salt bridge to an aspartic acid residue preceding an active-site serine residue, thereby forming the catalytic site characteristic of serine proteases.

The "artificial" serine proteases defined above are extremely valuable polypeptide cleaving tools for use in the method of the invention and in other methods where it is decisive to have a cleaving tool which will selectively cleave proteins, even large folded proteins. Analogously to bovine coagulation factor $X_a$, the above-defined artificial serine proteases in activated form are capable of selectively recognizing the cleaving-directing polypeptide segment SEQ ID NO: 38, but in contrast to bovine coagulation factor $X_a$, they can be established with such amino acid sequences that they can be readily produced using recombinant DNA techniques. Thus, the preferred artificial serine proteases of the invention are ones which have amino acid sequences allowing their synthesis by recombinant DNA techniques, in particular in prokaryote cells such as E. coli. As will appear from the following discussion and the examples, the artificial serine proteases of the invention, when produced in a prokaryote, may be given an enzymatically active conformation, in which the catalytically active domains are suitable exposed, by cycling according to the method of the present invention.

The quantitative test for selectivity of the artificial serine proteases involves determination of the cleavage rate, k, determined as the initial slope of a curve of absorption of light at 405 nm (absorption maximum of free paranitroaniline) versus time at 20° C.

Expressed quantitatively, the selectivity of the artificial serine proteases should be characterized by the value of (k(I)/k(V) being at most 0.06, and the value k(III)/k(V) being at most 0.5. It is preferred that (k(I)/k(V) is at most 0.05 and (k(I)/k(V) is at most 0.4, and more preferred that (k(I)/k(V) is at most 0.04 and k(III)/k(V) is at most 0.15.

A more comprehensive specificity characterization involves further model substrates: thus, the substrate specificity could be assessed to be identical to or better than that of bovine blood coagulation factor $X_a$ by each of the ratios (k(I)/k(V), k(II)/k(V), k(III)/k(V) and k(IV)/k(V)) between cleavage rate against each of the substrates I–IV:

I: Benzoyl-Val-Gly-Arg-paranitroanilide,

II: Tosyl Gly Pro Lys paranitroanilide,

III: Tosyl-Gly-Pro-Arg-paranitroanilide,

IV: (d,l)Val-Leu-Arg-paranitroanilide versus that against the substrate

V: Benzoyl-Ile-Glu-Gly-Arg-paranitroanilide at 20° C. pH=8 in a buffer consisting of 50 mM Tris, 100 mM NaCl, 1 mM $CaCl_2$, being identical to or lower than the corresponding ratio determined for bovine coagulation factor $X_a$ which is substantially free from contaminating proteases.

Within this characterization, (k(I)/k(V) should be at most 0.06, k(II)/k(V) should be at most 0.03, k(III)/k(V) should be at most 0.5, and k(IV)/k(V) should be at most 0.01, and it is preferred that (k(I)/k(V) is at most 0.05, k(II)/k(V) is at most 0.025, k(III)/k(V) is at most 0.4, and k(IV)/k(V) is at most 0.008, and more preferred that (k(I)/k(V) is at most 0.04, k(II)/k(V) is at most 0.015, k(III)/k(V) is at most 0.15, and k(IV)/k(V)) is at most 0.005.

The serine protease type polypeptide as defined above will normally have a molecular weight, $M_r$, of at most 70,000 and at least 15,000.

One such novel polypeptide according to the invention has the amino acid sequence SEQ ID NO: 2 or is an analogue and/or homologue thereof. Other important embodiments of the polypeptide of the invention have an amino acid sequence which is a subsequence of SEQ ID NO: 2 or an analogue and/or homologue of such a subsequence.

By the use of the term "an analogue of a polypeptide encoded by the DNA sequence" or "an analogue of a polypeptide having the amino acid sequence" is meant any polypeptide which is capable of performing as bovine coagulation factor $X_a$ is the tests mentioned above. Thus, included are also polypeptides from different sources, such as different mammals or vertebrates, which vary e.g. to a certain extent in the amino acid composition, or the post-translational modifications e.g. glycosylation or phosphorylation, as compared to the artificial serine protease described in the examples.

The term "analogue" is thus used in the present context to indicate a protein or polypeptide of a similar amino acid composition or sequence as the characteristic amino acid sequence SEQ ID NO: 2 derived from an artificial serine protease as described in Example 5, allowing for minor variations that alter the amino acid sequence e.g. deletions, site directed mutations, insertions of extra amino acids, or combinations thereof, to generate artificial serine protease analogues.

Therefore, in the present description and claims, an analogue (of a polypeptide) designates a variation of the polypeptide in which one or several amino acids may have been deleted or exchanged, and/or amino acids may have been introduced, provided the enzymatic activity with the above-defined specificity is retained, as can be assessed as described above.

With respect to homology, an analogue of a polypeptide according to the invention may have a sequence homology at the polypeptide level of at least 60% identity compared to the sequence of a fragment of SEQ ID NO: 2, allowing for deletions and/or insertions of at most 50 amino acid residues.

Such polypeptide sequences or analogues thereof which has homology of at least 60% with the polypeptide shown in SEQ ID NO: 2 encoded for by the DNA sequence of the invention SEQ ID NO: 1 or analogues and/or homologues thereof, constitute an important embodiment of this invention.

By the term "sequence homology" is meant the identity in sequence of either the amino acids in segments of two or more amino acids in a amino acid sequence, or the nucleotides is segments of two or more nucleotides in a nucleotide sequence. With respect to polypeptides, the terms are thus intended to mean a homology between the amino acids in question between which the homology is to be established, in the match with respect to identity and position of the amino acids of the polypeptides.

The term "homologous" is thus used here to illustrate the degree of identity between the amino acid sequence of a given polypeptide and the amino acid sequence shown in SEQ ID NO: 2. The amino acid sequence to be compared with the amino acid sequence shown in SEQ ID NO: 2 may be deduced from a nucleotide sequence such as a DNA or RNA sequence, e.g. obtained by hybridization as defined in the following, or may be obtained by conventional amino acid sequencing methods.

Another embodiment relates to a polypeptide having an amino acid sequence from which a consecutive string of 20 amino acids is homologous to a degree of at least 40% with a string of amino acids of the same length selected from the amino acid sequence shown in SEQ ID NO: 2.

One serine protease polypeptide according to the invention has the amino acid sequence of SEQ ID NO: 2, residues 82–484, or is an analogue and/or homologue thereof. Another serine protease polypeptide according to the invention has the amino acid sequence of SEQ ID NO: 2, residues 166–484, or is an analogue and/or homologue thereof.

A number of modifications of the sequences shown herein are particularly interesting. The insertion of the cleaving directing sequences SEQ ID NO: 38 or 40–42 instead of residues 230–233 in SEQ ID NO: 2, combined with exchange of cysteine residue 245 by preferably Gly, Ser or Arg in SEQ ID NO: 2. Another interesting possibility is insertion of SEQ ID NO: 38 or 40–42 instead of residues 179–182 in SEQ ID NO: 2. Quite generally, in any of the artificial serine proteases defined above, replacement of the cleaving sequence corresponding to residues 230–233 in SEQ ID NO: 2 with one of the cleavage-directing sequences defined above will give rise to extremely useful cleaving enzymes for use in the method according to the invention, in that these can be selectively and very efficiently cleaved by enzymes having the specific enzymatic activity of bovine coagulation factor $X_a$, and thus by artificial serine proteases as defined above, including by molecules identical to themselves. The latter fact means that artificial serine proteases modified by such insertion of the specific cleaving-directing sequences can be extremely effectively activated, as the first molecules cleaved and activated will be able to cleave other molecules, thus starting a chain reaction.

As mentioned above, it is a most important feature that the artificial serine proteases can be produced by recombinant DNA techniques, and hence, another important embodiment of the invention relates to a nucleic acid fragment capable of encoding a polypeptide according as defined above, in particular a DNA fragment which is capable of encoding an artificial serine protease polypeptide as defined above.

In one of its aspects, the invention relates to a nucleotide sequence encoding a polypeptide of the invention as defined above. In particular, the invention relates to a nucleotide sequence having the nucleotide sequence shown in the DNA sequence SEQ ID NO: 1 or an analogue thereof which has a homology with any of the DNA sequences shown in SEQ ID NO: 1 of at least 60%, and/or encodes a polypeptide, the amino acid sequence of which is at least 60% homologous with the amino acid sequences shown in SEQ ID NO: 2.

Generally, only coding regions are used when comparing nucleotide sequences in order to determine their internal homology.

The term "analogue" with regard to the DNA fragments of the invention is intended to indicate a nucleotide sequence which encodes a polypeptide identical or substantially identical to the polypeptide encoded by a DNA fragment of the invention. It is well known that the same amino acid may be encoded by various codons, the codon usage being related, inter alia, to the preference of the organisms in question expressing the nucleotide sequence. Thus, one or more nucleotides or codons of the DNA fragment of the invention may be exchanged by others which, when expressed, result in a polypeptide identical or substantially identical to the polypeptide encoded by the DNA fragment in question.

Furthermore, the term "analogue" is intended to allow for variations in the sequence such as substitution, insertion (including introns), addition and rearrangement of one or more nucleotides, which variations do not have any substantially effect on the polypeptide encoded by the DNA fragment.

Thus, within the scope of the present invention is a modified nucleotide sequence which differs from the DNA sequence shown in SEQ ID NO: 1 in that at least one nucleotide has been substituted, added, inserted, deleted and/or rearranged.

The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence of at any suitable point within it, and "rearrangement" is intended to mean that two or more nucleotide residues have been exchanged within the DNA or polypeptide sequence, respectively. The DNA fragment may, however, also be modified by mutagenesis either before or after inserting it in the organism. The DNA or protein sequence of the invention may be modified in such a way that it does not lost any of its biophysical, biochemical or biological properties, or part of such properties (one and/or all) or all of such properties (one and/or all).

An example of a specific analogue of the DNA sequence of the invention is a DNA sequence which comprises the DNA sequence shown in SEQ ID NO: 1 and particularly adapted for expression in *E. coli*. This DNA sequence is one which, when inserted in *E. coli* together with suitable regulatory sequences, results in the expression of a polypeptide having substantially the amino acid sequence shown in SEQ ID NO: 2. Thus, this DNA sequence comprises specific codons recognized by *E. coli*.

The terms "fragment", "sequence", "homologue" and "analogue", as used in the present specification and claims with respect to fragments, sequences, homologues and analogues according to the invention should of course be understood as not comprising these phenomena in their natural environment, but rather, e.g., in isolated, purified, in vitro or recombinant form.

One embodiment of the nucleic acid fragment according to the invention is a nucleic acid fragment as defined above in which at least 60% of the coding triplets encode the same amino acids as a nucleic acid fragment of the nucleic acid which encodes bovine coagulation factor X, allowing for insertions and/or deletions of at most 150 nucleotides. An example of such a nucleic acid fragment is SEQ ID NO: 1, nucleotides 76–1527, and analogues and/or homologues there of. Another example is SEQ ID NO: 1, nucleotides 319–1527, and analogues and/or homologues thereof. Still another example is SEQ ID NO: 1, nucleotides 571–1527, and analogues and/or homologues thereof.

The DNA fragment described above and constituting an important aspect of the invention may be obtained directly from the genomic DNA or by isolating mRNA and converting it into the corresponding DNA sequence by using reverse transcriptase, thereby producing a cDNA. When obtaining the DNA fragment from genomic DNA, it is derived directly by screening for genomic sequences as is well known for the person skilled in the art. It can be accomplished by hybridization to a DNA probe designed on the basis of knowledge of the sequences of the invention, or the sequence information obtained by amino acid sequencing of a purified serine protease. When the DNA is of complementary DNA (cDNA) origin, it may be obtained by preparing a cDNA library with mRNA from cells containing an artificial serine protease. Hybridization can be accomplished by a DNA probe designed on the basis of knowledge of the cDNA sequence, or the sequence information obtained by amino acid sequencing of a purified artificial serine protease.

The DNA fragment of the invention or an analogue and/or homologue thereof of the invention can be replicated by fusing it with a vector and inserting the complex into a suitable microorganism or a mammalian cell line. Alternatively, the DNA fragment can be manufactured using chemical synthesis. Also, polymerase chain reaction (PCR) primers can be synthesized based on the nucleotide sequence shown in SEQ ID NO: 1. These primers can then be used to amplify the whole or a part of a sequence encoding an artificial serine protease polypeptide.

Suitable polypeptides of the invention can be produced using recombinant DNA technology. More specifically, the polypeptides may be produced by a method which comprises culturing or breeding an organism carrying the DNA sequence shown in SEQ ID NO: 1 or an analogue and/or homologue thereof of the invention under conditions leading to expression of said DNA fragment, and subsequently recovering the expressed polypeptide from the said organism.

The organism which is used for the production of the polypeptide may be a higher organism, e.g. an animal, or a lower organism, e.g. a microorganism. Irrespective of the type of organism used, the DNA fragment of the invention (described above) should be introduced in the organism either directly or with the help of a suitable vector. Alternatively, the polypeptides may be produced in the mammalian cell lines by introducing the DNA fragment or an analogue and/or homologue thereof of the invention either directly or with the help of an expression vector.

The DNA fragment of the invention can also be cloned in a suitable stable expression vector and then put into a suitable cell line. The cells expressing the desired polypeptides are then selected using the conditions suitable for the vector and the cell line used. The selected cells are then grown further and form a very important and continuous source of the desired polypeptides.

Thus, another aspect of the invention relates to an expression system comprising a nucleic acid fragment as defined above and encoding an artificial serine protease polypeptide as defined above, the system comprising a 5' flanking sequence capable of mediating expression of said nucleic acid fragment. The expression system may be a replicable expression vector carrying the nucleic acid fragment, which vector is capable of replicating in a host organism or a cell line; the vector may, e.g., be a plasmid, phage, cosmid, mini-chromosome or virus; the vector may be one which, when introduced in a host cell, is integrated in the host cell genome.

Another aspect of the invention relates to an organism which carries and is capable of replicating the nucleic acid fragment as defined above. The organism may be a microorganism such as a bacterium, a yeast, a protozoan, or a cell derived from a multicellular organism such as a fungus, an insect cell, a plant cell, a mammalian cell or a cell line. Particularly intersecting host organisms are microorganisms such as a bacterium of the genus Escherichia, Racillus or Salmonella.

A further aspect of the invention relates to a method of producing an artificial serine protease polypeptide as defined above, comprising the following steps of:

1. inserting a nucleic acid fragment as defined above in an expression vector,
2. transforming a host organism as defined above with the vector produced in step a,
3. culturing the host organism produced in step b to express the polypeptide,
4. harvesting the polypeptide,
5. optionally subjecting the polypeptide to post-translational modification,
6. if necessary subjecting the polypeptide to the denaturing/renaturing cycling method according to the present invention, and
7. optionally subjecting the polypeptide to further modification to obtain an authentic polypeptide as defined above.

Further modifications of the polypeptides may for instance be accomplished by subjecting the polypeptide molecules to carboxypeptidase A or B, whereby selected amino acid residues may be removed from the C-terminus of the polypeptide molecules. This is desirable under circumstances wherein the optimal folding of the authentic polypeptide molecules only is achieved when the N-terminus is free and the cleavage directing polypeptide (such as SEQ ID NO: 37) thus is placed C-terminally of the authentic polypeptide. As is known, carboxypeptidase B cleaves sequentially from the C-terminus, and only cleaves off basic amino acids, whereas carboxypeptidase A cleaves off non-basic amino acids. By carefully designing which residue is adjoined C-terminally to the authentic polypeptide it is possible to ensure that all but the authentic polypeptide is cleaved by the carboxypeptidases. If the C-terminus of the authentic polypeptide is a basic amino acid residue one should assure that the C-terminally linked residue which is to be removed is non-basic and vice versa. If one knows the sequence of the amino acid residues from the C-terminus to the C-terminus of the authentic polypeptide it is possible to alternate between treatments with the two carboxypeptidases until only the naked, authentic polypeptide is left. A practical embodiment would be to use immobilized carboxypeptidases.

The polypeptide produced may be isolated by a method comprising one or more steps like affinity chromatography using immobilized polypeptide or antibodies reactive with said polypeptide and/or other chromatographic and electrophoretic procedures.

Also, it will be understood that a polypeptide of the invention may be prepared by the well known methods of liquid or solid phase peptide synthesis utilizing the successive coupling of the individual amino acids of the polypeptide sequence. Alternatively, the polypeptides can be synthesized by the coupling of individual amino acids forming fragments of the polypeptide sequence which are later coupled so as to result in the desired polypeptide. These methods thus constitute another interesting aspect of the invention.

The invention also relates to the use of an artificial serine protease polypeptide as defined above for cleaving polypeptides at the cleavage site for bovine coagulation factor $X_a$, the cleavage site having the amino acid sequence selected from the group consisting of SEQ ID NO: 38, SEQ ID NO: 40, SEQ ID NO: 41 and SEQ ID NO: 42, and to the use of a an artificial serine protease polypeptide as defined above for cleaving polypeptides at the cleavage site for bovine coagulation factor $X_a$, the cleavage site having a modified version of the amino acid sequence selected from the group of SEQ ID NO: 43, SEQ ID NO: 44, SEQ ID NO: 45 and SEQ ID NO: 46, which has been converted to a cleavable form as described further above.

Solvent composition is expressed in terms of a binary mixture of a non-denaturing 'buffer A' and a denaturing 'buffer B' in terms of relative content of buffer B. Three consecutive cycles are represented, each consisting of a renaturation phase 'F' and a denaturation phase 'D'. Changes in level of denaturing power of the solvent mixture during denaturation phases in consecutive cycles are denoted 'k'.

Figure 1:
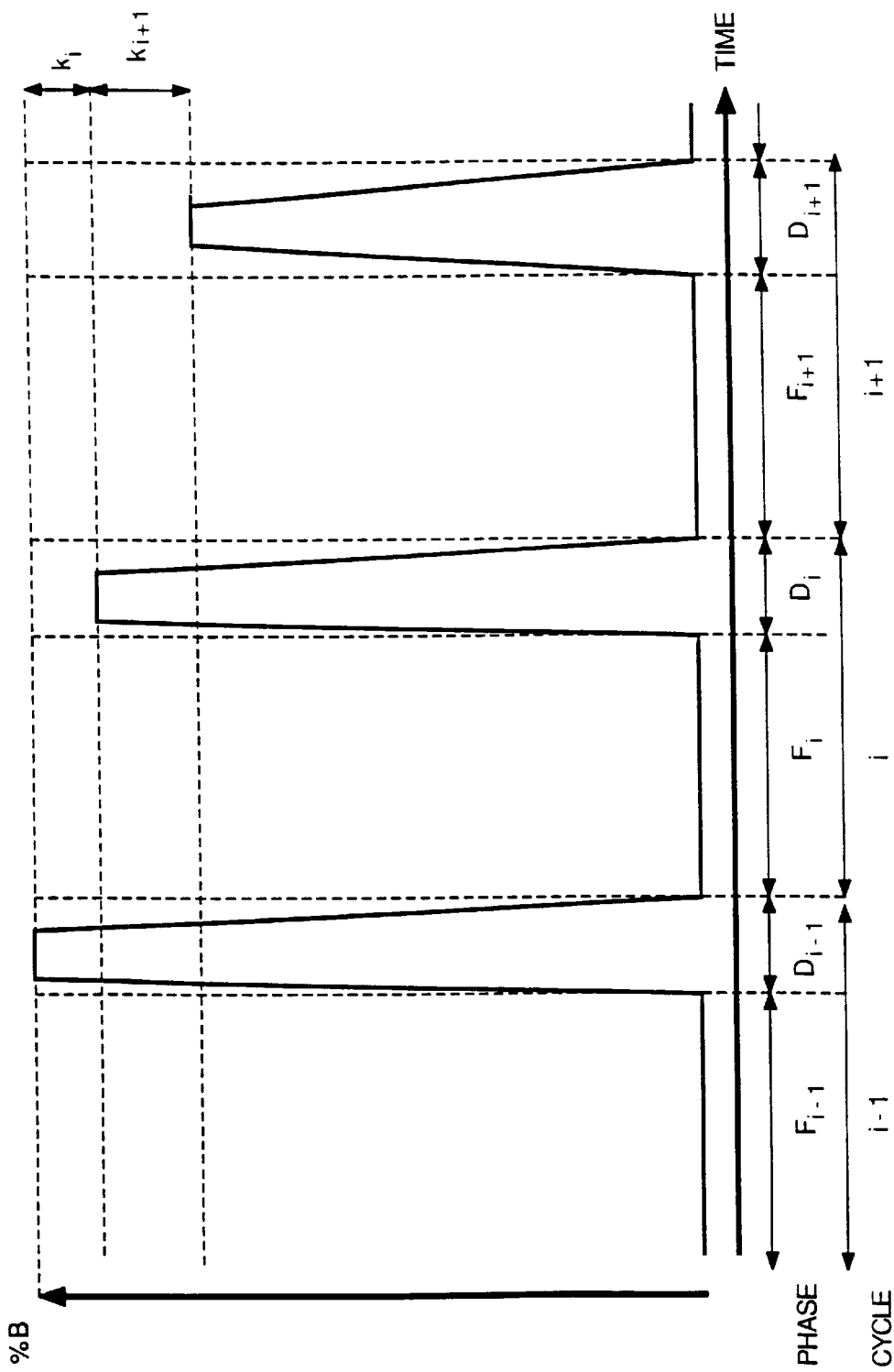
FIG. 1: Schematic representation of segment of a cyclic denaturation/renaturation time programme.
Figure 2:
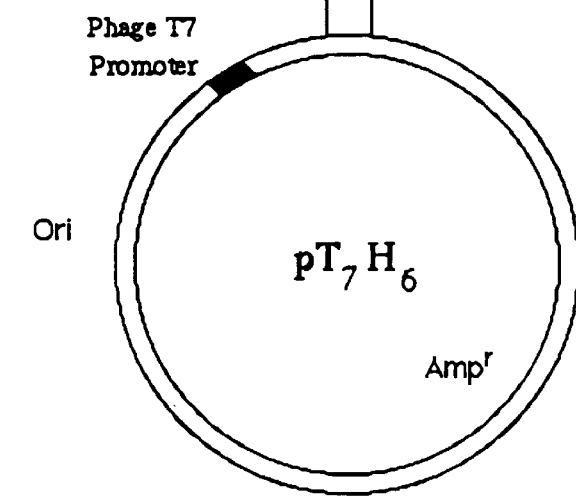

FIG. 2: Construction of the expression plasmids $pT_7H_6FX$-hβ2m and $pT_7H_6FX$-mβ2m.

The amplified DNA fragments containing the reading frames of human- and murine $β_2$-microglobulin from amino acid residues $Ile_1$ to $Met_{99}$, fused at the 5'-end to the nucleotide sequences encoding the $FX_a$ cleavage site (SEQ ID NO: 37), were cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIGS. 3a–3b: Amino acid sequences of human- and murine $β_2$-microglobulin.

A: Predicted amino acid sequence of the full length reading frame encoding human $β_2$-microglobulin (SEQ ID NO: 49). Amino acid residue one (Ile) in the processed mature protein is indicated. B: Predicted amino acid sequence of the full length reading frame encoding murine $β_2$-microglobulin (SEQ ID NO: 50). Amino acid residue one (Ile) in the processed mature protein is indicated.

Figure 4:
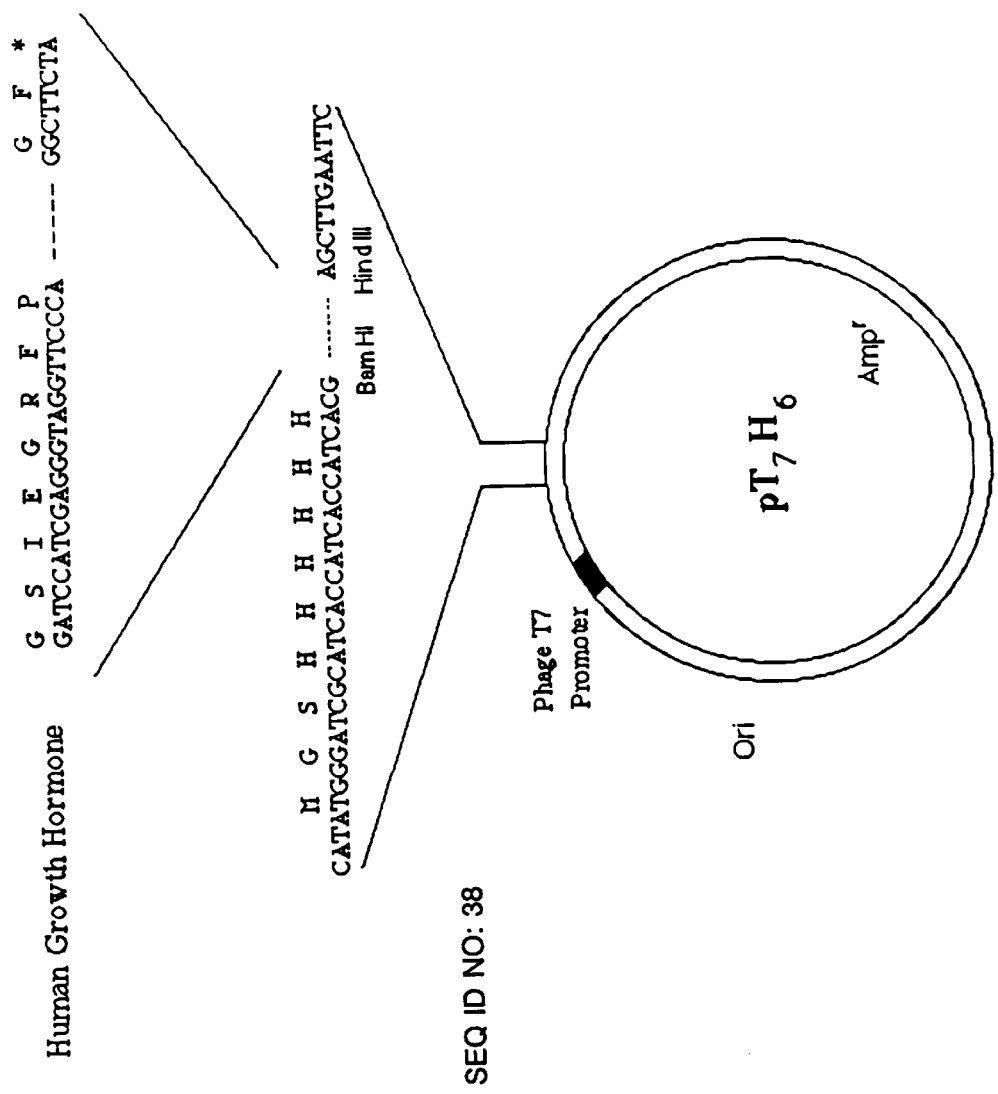

FIG. 4: Construction of the expression plasmid $pT_7H_6FX$-hGH.

The amplified DNA fragment containing the reading frame of human Growth Hormone from amino acid residues $Phe_1$ to $Phe_{191}$, fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIG. 5: Amino acid sequence of human Growth Hormone (Somatotropin).

The predicted amino acid sequence of the full length reading frame encoding human Growth Hormone (SEQ ID NO: 51). The first Amino acid residue in the processed mature protein ($Phe_1$) is indicated.

Figure 6:
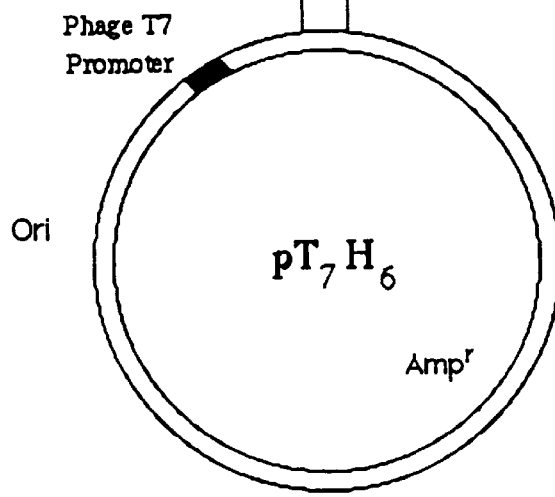

FIG. 6: Construction of the plasmids $pT_7H_6FX$-#1, #2, and #3 expressing amino acid residue no. 20 (Ala) to 109 (Arg), amino acid residue no 20 (Ala) to 190 (Ala), and amino acid residue no. 20 (Ala) to 521 (Lys) of the human $α_2$-Macroglobulin Receptor Protein ($α_2$MR) (SEQ ID NO: 52).

The amplified DNA fragments derived from the reading frame of the $α_2$MR from #1: amino acid residue no. 20

(Ala) to 109 (Arg), #2: amino acid residue no. 20 (Ala) to 190 (Ala), and #3: amino acid residue no. 20 (Ala) to 521 (Lys), fused at the 5'-end to the nucleotide sequence encoding the $FX_a$ cleavage site IEGR (SEQ ID NO: 38), were cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

Figure 7:
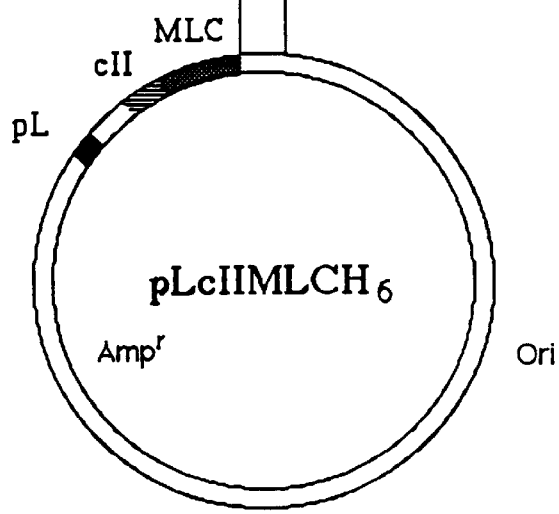

FIG. 7: Construction of the plasmids $pLcIIMLCH_6FX$-#4, #5, and #6 expressing amino acid residue no. 803 (Gly) to 1265 (Asp), amino acid residue no. 849 (Val) to 1184 (Gln), and amino acid residue no. 1184 (Gln) to 1582 (Lys) of the human $\alpha_2$-Macroglobulin Receptor Protein ($\alpha_2$MR) (SEQ ID NO: 52).

The amplified DNA fragments derived from the reading frame of the $\alpha_2$MR from #4: amino acid residue no. 803 (Gly) to 1265 (Asp), #5: amino acid residue no. 849 (Val) to 1184 (Gln), and #6: amino acid residue no. 1184 (Gln) to 1582 (Lys), fused at the 5'-end to the nucleotide sequence encoding the $FX_a$ cleavage site IEGR (SEQ ID NO: 38), were cut with the restriction endonucleases Bam HI or BcI and Hind III (purchased from Boehringer, Germany) and ligated with $T_4$ DNA ligase (purchased from Boehringer, Germany) into Bam HI and Hind III cut $pLcIIMLCH_6FX$ using standard procedures.

Figure 8:
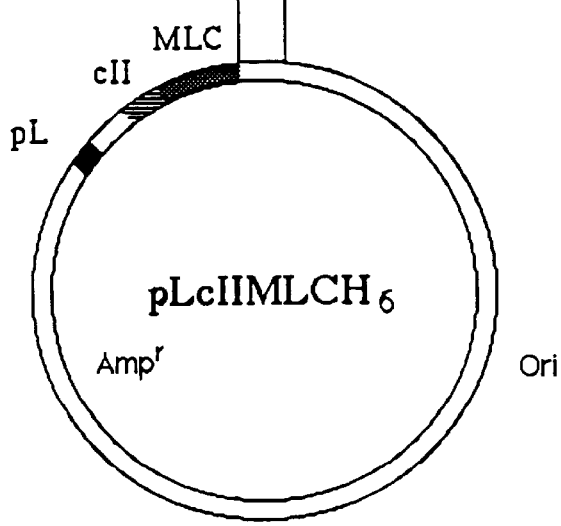

FIG. 8: Construction of the plasmids $pLcIIMLCH_6FX$-#7, #8, and #9 expressing amino acid residue no. 803 (Gly) to 1582 (Lys), amino acid residue no. 2519 (Ala) to 2941 (Ile), and amino acid residue no. 3331 (Val) to 3778 (Ile) of the human $\alpha_2$-Macroglobulin Receptor Protein ($\alpha_2$MR) (SEQ ID NO: 52).

The amplified DNA fragments derived from the reading frame of the $\alpha_2$MR from #7: amino acid residue no. 803 (Gly) to 1582 (Lys), #8: amino acid residue no. 2519 (Ala) to 2941 (Ile), and #9: amino acid residue no. 3331 (Val) to 3778 (Ile), fused at the 5'-end to the nucleotide sequence encoding the $FX_a$ cleavage site IEGR (SEQ ID NO: 38), were cut with the restriction endonucleases Bam HI and Hind III (purchased from Boehringer, Germany) and ligated with $T_{4\ D}NA$ ligase (purchased from Boehringer, Germany) into Bam HI and Hind III cut $pLcIIMLCH_6FX$ using standard procedures.

FIGS. 9a and 9b.: Amino acid sequence of human $\alpha_2$-Macroglobulin Receptor Protein ($\alpha_2$MR) (SEQ ID NO: 52).

The predicted amino acid sequence of the full length reading frame encoding the $\alpha_2$MR. Amino acid residues present in the recombinant proteins as N- or C-terminal residues are identified by their numbers above the $\alpha_2$MR sequence.

Figure 10:
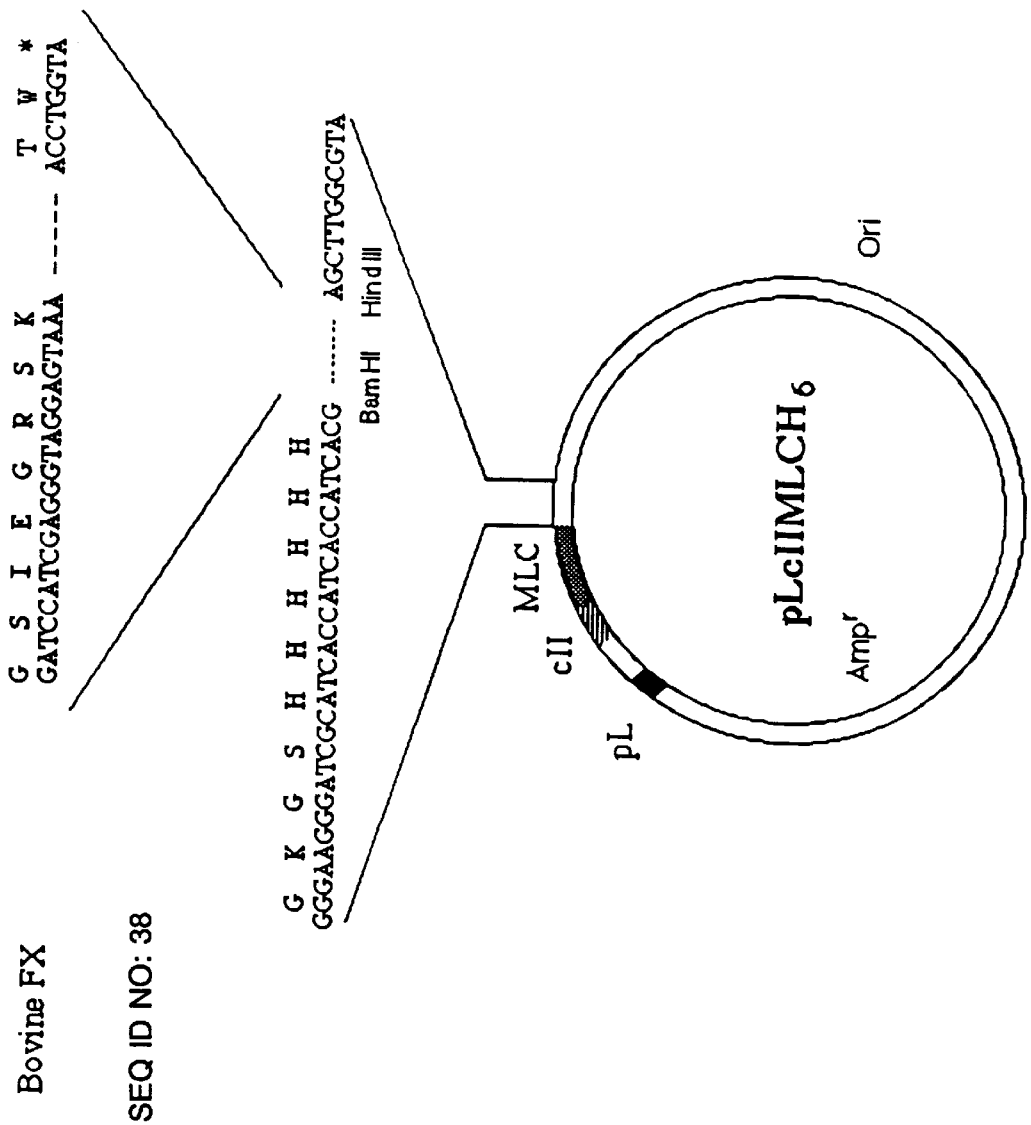

FIG. 10: Construction of the expression plasmid $pLcIIMLCH_6FX$-$FX\Delta\gamma$.

The amplified DNA fragment containing the reading frame of bovine blood coagulation Factor X from amino acid residue $Ser_{82}$ to $Trp_{484}$, ($FX\Delta\gamma$) fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pLcIIMLCH_6FX$ using standard procedures.

FIG. 11: Amino acid sequence of bovine blood coagulation Factor X (FX).

The predicted amino acid sequence of the full length reading frame encoding bovine FX (SEQ ID NO: 53). The N-terminal amino acid residue $Ser_{82}$ and the C terminal $Trp_{484}$ residue in the $FX\Delta\gamma$ construct are identified.

Figure 12:
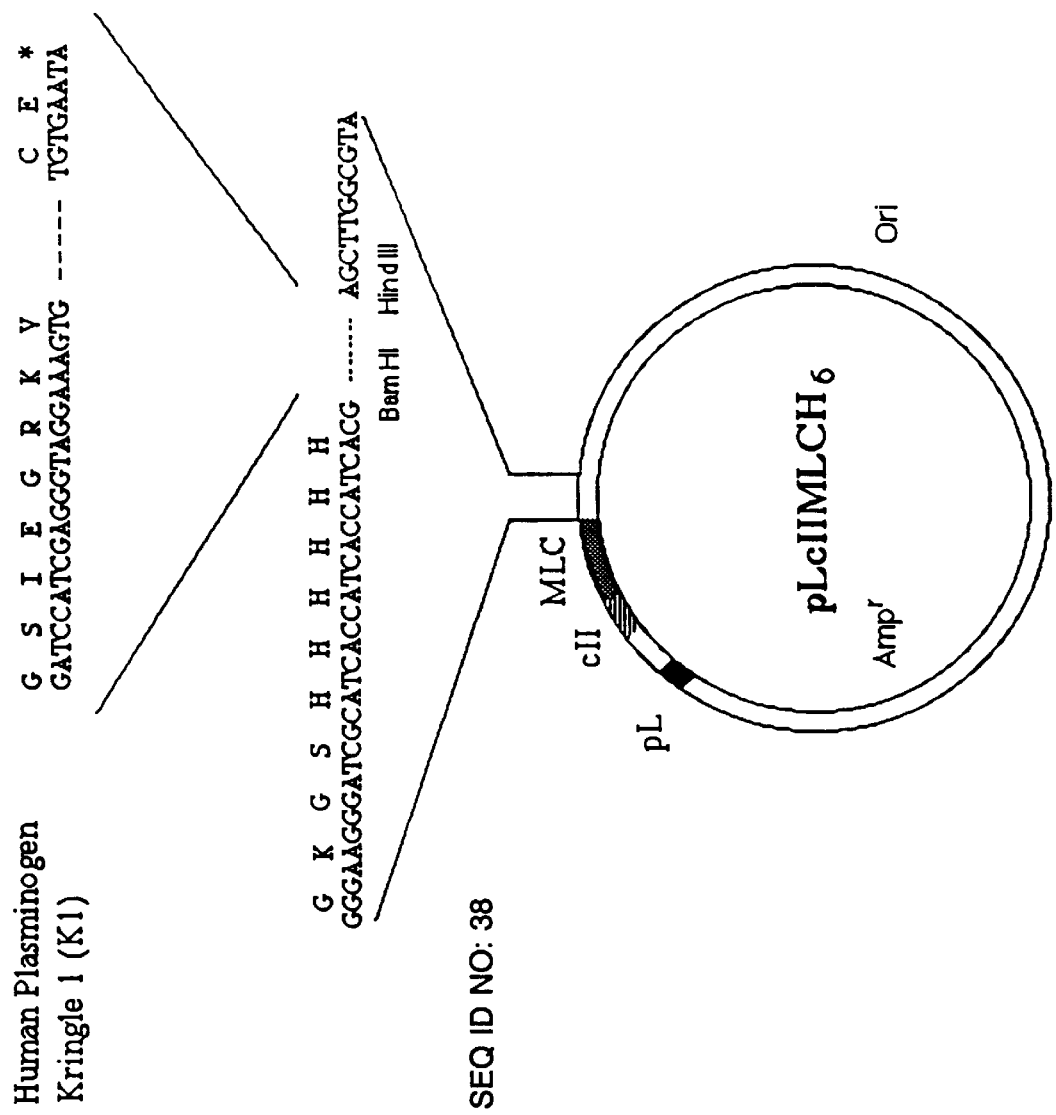

FIG. 12: Construction of the expression plasmid $pLcIIMLCH_6FX$-K1.

The amplified DNA fragment containing the reading frame of human plasminogen kringle 1 (K1) from amino acid residue $Ser_{82}$ to $Glu_{162}$ (numbering as in "Glu"-plasminogen), fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pLcIIMLCH_6FX$ using standard procedures.

Figure 13:
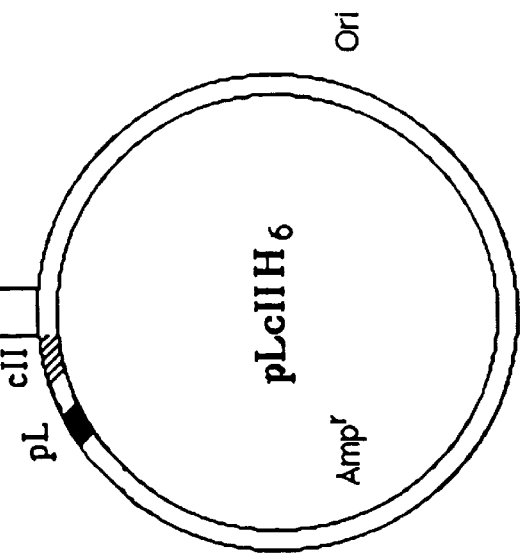

FIG. 13: Construction of the expression plasmid $pLcIIH_6FX$-K4.

The amplified DNA fragment containing the reading frame of human plasminogen kringle 4 (K4) from amino acid residue $Val_{354}$ to $Ala_{439}$ (numbering as in "Glu"-plasminogen), fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pLcIIH_6FX$ using standard procedures.

Figure 14:
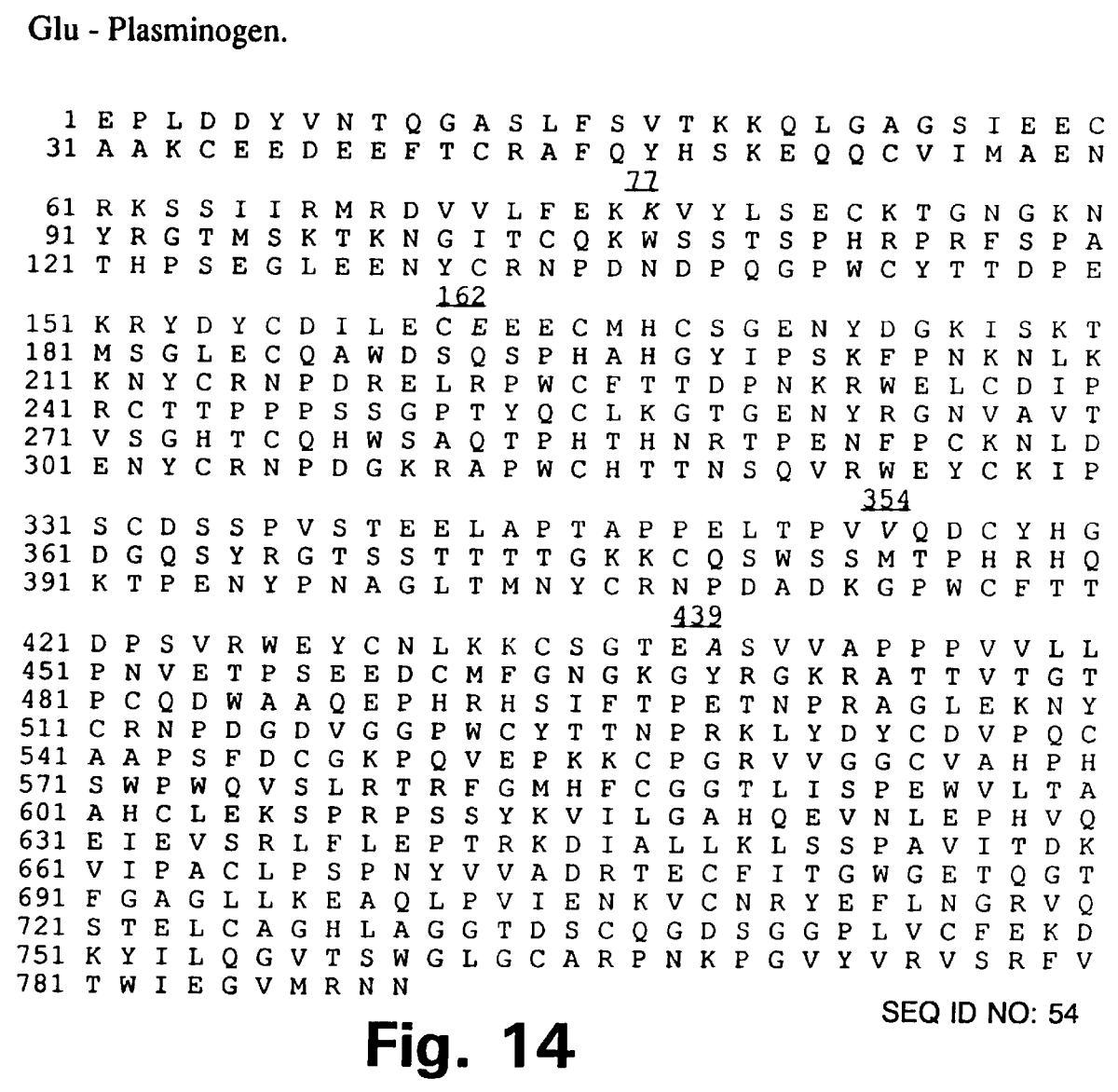

FIG. 14: Amino acid sequence of human "Glu"—Plasminogen (SEQ ID NO: 54). The N- and C-terminal amino acid residues in the K1 and K4 constructs are identified by their numbers in the sequence.

Figure 15:
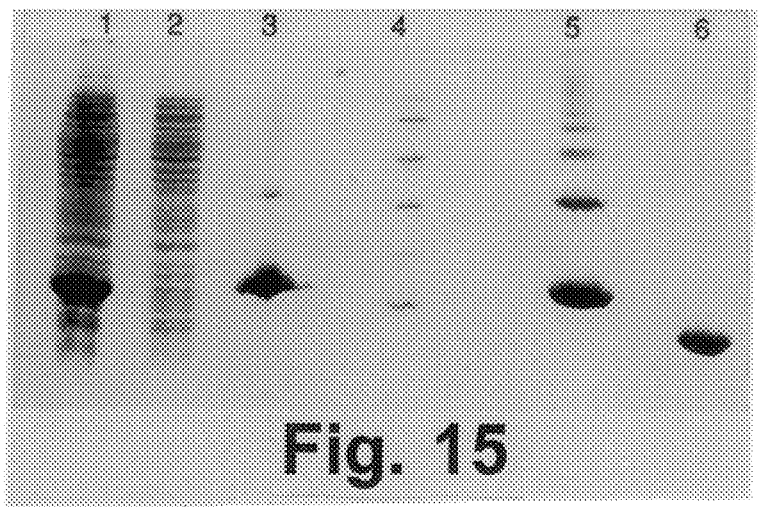

FIG. 15: SDS-PAGE analysis of production and in vitro folding of recombinant human $\beta_2$-microglobulin.

Lane 1: Crude protein extract before application to the $Ni^{2+}NTA$-agarose column (reduced sample).

Lane 2: Column flow-through during application of the crude protein extract onto the $Ni^{2+}NTA$-agarose column (reduced sample)

Lane 3: Human $\beta_2$-microglobulin eluted from the $Ni^{2+}NTA$-agarose column after the cyclic folding procedure by the non-denaturing elution buffer (reduced sample).

Lane 4: Protein markers (Pharmacia, Sweden): From top of gel; 94 kDa, 67 kDa, 43 kDa, 30 kDa, 20.1 kDa, and 14.4 kDa (reduced sample)

Lane 5: Same as lane 3 (non-reduced sample)

Lane 6: Recombinant human $\beta_2$-microglobulin after $FX_a$ cleavage and final purification (non-reduced sample).

Figure 16:
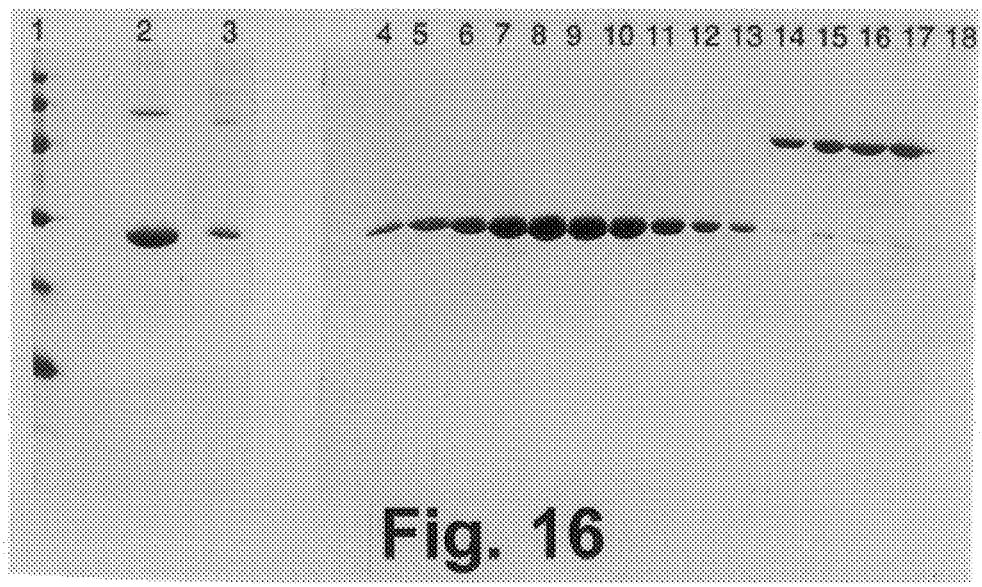

FIG. 16: SDS-PAGE analysis of in vitro folding of recombinant human Growth Hormone; hGH (Somatotropin).

Lane 1: Protein markers (Pharmacia, Sweden): From top of gel; 94 kDa, 67 kDa, 43 kDa, 30 kDa, 20.1 kDa, and 14.4 kDa (reduced sample)

Lane 2: Human hGH eluted from the $Ni^{2+}NTA$-agarose column after the cyclic folding procedure by the non-denaturing elution buffer (non-reduced sample).

Lane 3: Human hGH eluted from the $Ni^{2+}NTA$-agarose column after the cyclic folding procedure by the denaturing elution buffer B from the folding procedure (non-reduced sample).

Lane 4–18: Fractions collected during the separation of monomeric hGH-fusion protein from dimer and multimer fusion proteins after the cyclic folding procedure by ion exchange chromatography on Q-Sepharose (Pharmacia, Sweden). The monomeric protein was eluted in a peak well separated from the peak containing the dimer and multimer proteins (non-reduced samples).

Figure 17:
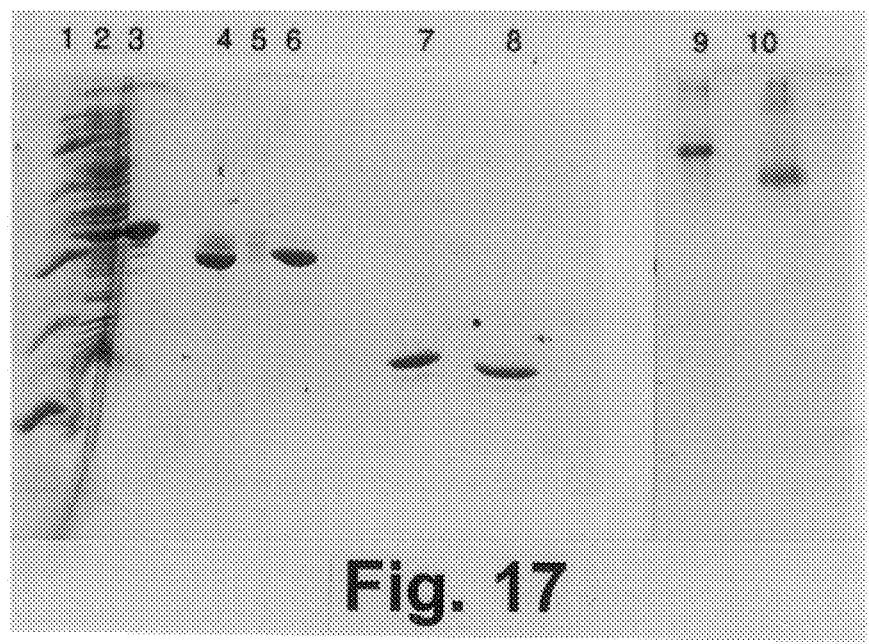

FIG. 17: SDS-PAGE analysis of in vitro folding of recombinant kringle 1 and 4 from human plasminogen and recombinant fusion protein #4 derived from human $\alpha_2$-Macroglobulin Receptor Protein ($\alpha_2$MR).

Lane 1: Protein markers (Pharmacia, Sweden): From top of gel; 94 kDa, 67 kDa, 43 kDa, 30 kDa, 20.1 kDa, and 14.4 kDa (reduced sample).
Lane 2: Crude K1-fusion protein extract before application to the $Ni^{2+}$NTA-agarose column (reduced sample).
Lane 3: K1-fusion protein eluted from the $Ni^{2+}$NTA-agarose column after the cyclic folding procedure by the non-denaturing elution buffer (reduced sample).
Lane 4: Same as lane 3 (non-reduced sample).
Lane 5: Flow-through from the lysine-agarose column during application of the K1-fusion protein (non-reduced sample).
Lane 6: K1-fusion protein eluted from the lysine-agarose column (non-reduced sample).
Lane 7: K4-fusion protein eluted from the $Ni^{2+}$NTA-agarose column after the cyclic folding procedure by the non-denaturing elution buffer (reduced sample).
Lane 8: Same as lane 7 (non-reduced sample).
Lane 9: $\alpha_2$MR#4 fusion protein eluted from the $Ni^{2+}$NTA-agarose column after the cyclic folding procedure by the non-denaturing elution buffer (reduced sample).
Lane 10: Same as lane 9 (non-reduced sample).

Figure 18:
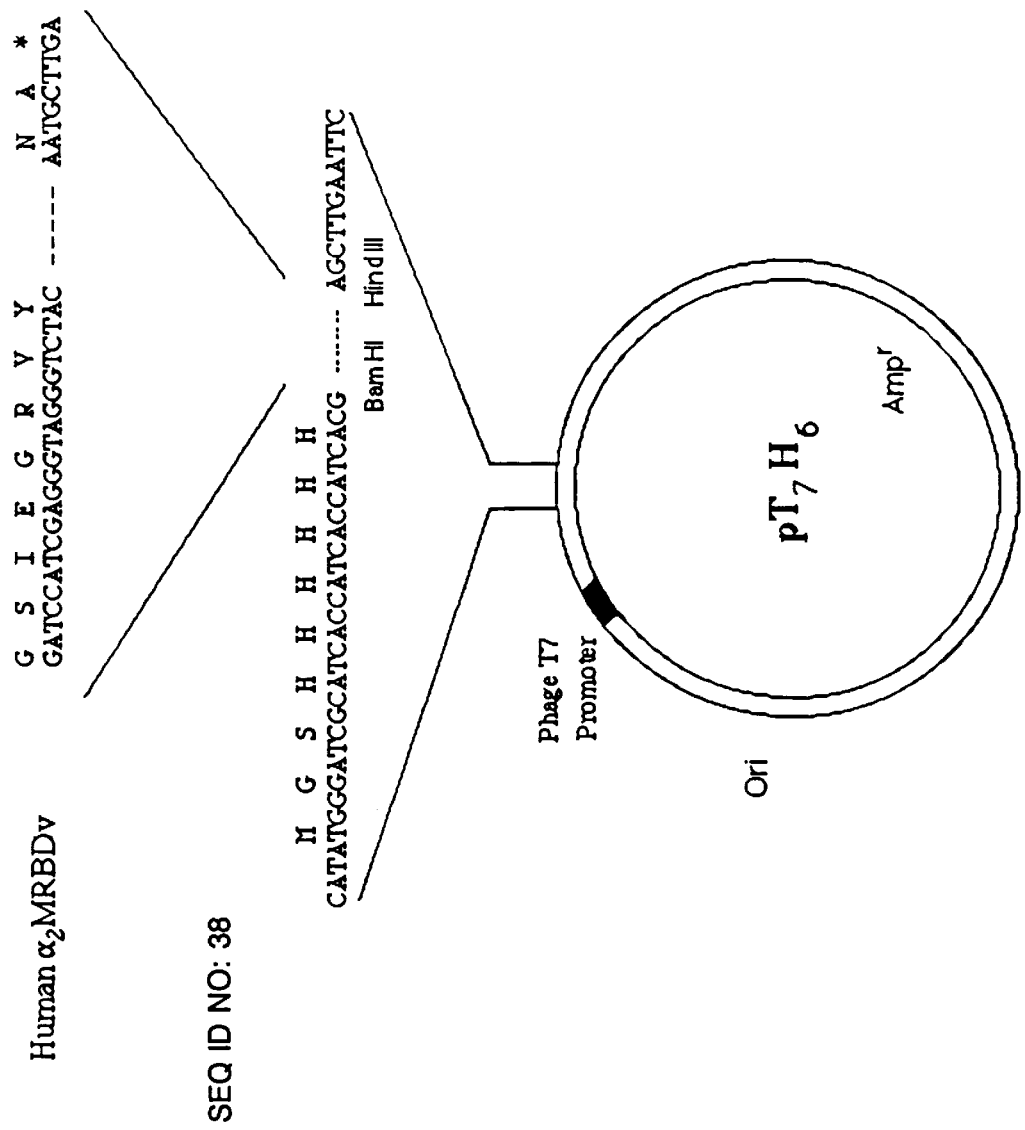

FIG. 18: Construction of the expression plasmid $pT_7H_6FX$ $\alpha_2$MRBDv.
The amplified DNA fragment containing the reading frame of human $\alpha_2$-Macroglobulin from amino acid residues $Val_{1299}$ to $Ala_{1451}$, fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIG. 19: Amino acid sequence of the receptor-binding domain of human $\alpha_2$-Macroglobulin (from residue $Val_{1299}$ to $Ala_{1451}$) (SEQ ID NO: 55).

Figure 20:
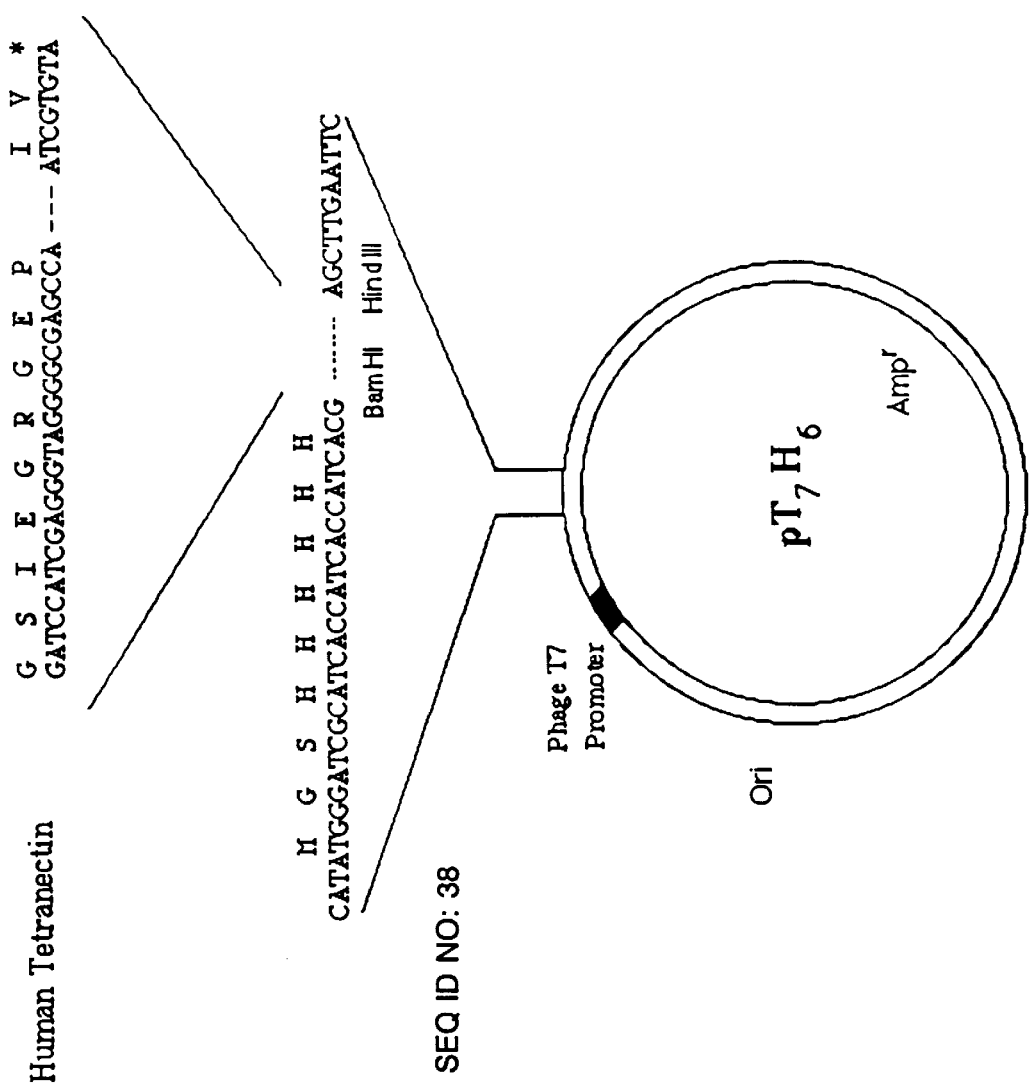

FIG. 20: Construction of the expression plasmid $pT_7H_6FX$-TETN.
The amplified DNA fragment containing the reading frame of mature monomeric human Tetranectin from amino acid residues $Glu_1$ to $Val_{181}$, fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIG. 21: Amino acid sequence of human monomeric Tetranectin.
The predicted amino acid sequence of the full length reading frame encoding human Tetranectin (SEQ ID NO: 56). The first Amino acid residue in the processed mature protein ($Glu_1$) is indicated.

Figure 22:
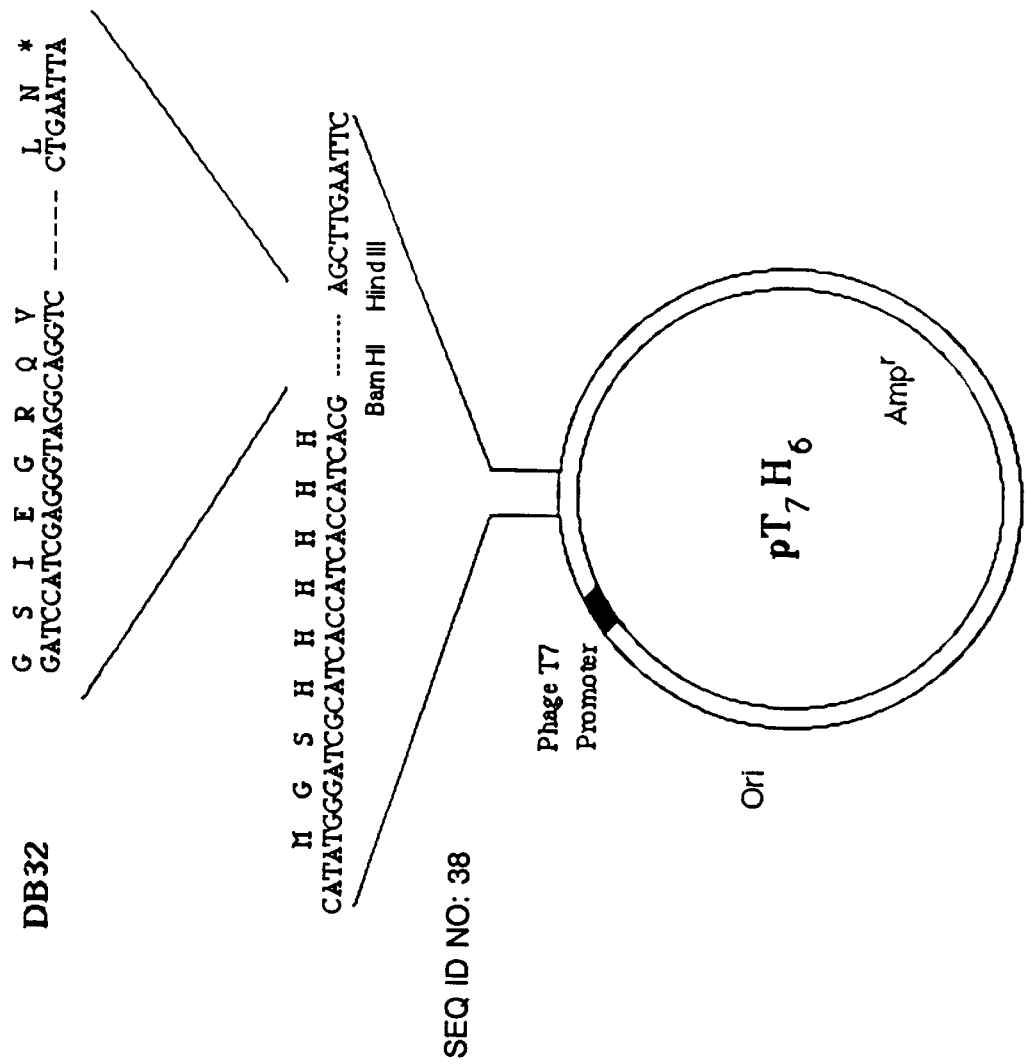

FIG. 22: Construction of the expression plasmid $pT_7H_6FX$-DB32.
The amplified DNA fragment containing the reading frame of the artificial diabody DB32 from amino acid residues $Gln_1$ to $Asn_{246}$, fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIG. 23: Amino acid sequence of the artificial diabody DB32 (SEQ ID NO: 57).

Figure 24:
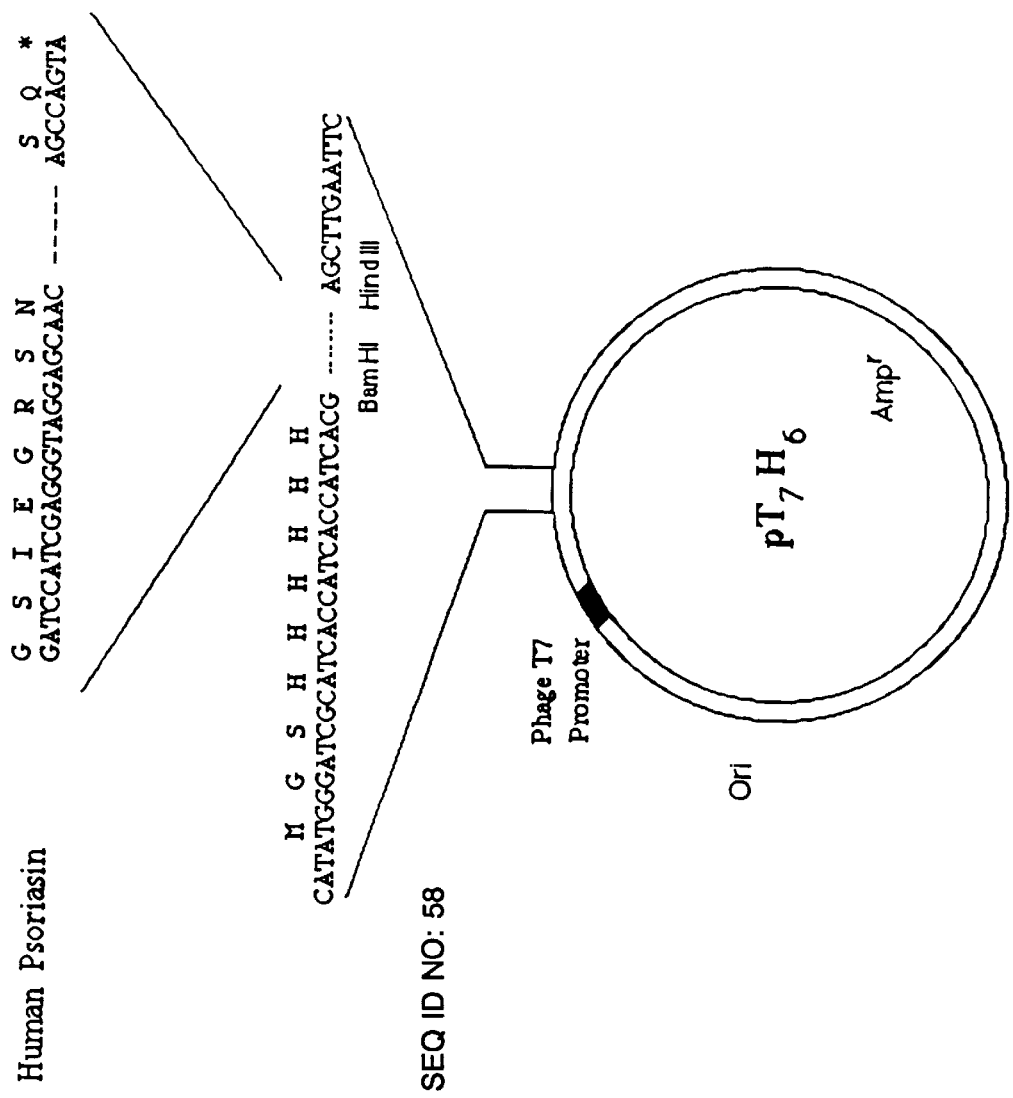

FIG. 24: The expression plasmid $pT_7H_6FX$-PS.4.

The construction of $pT_7H_6FX$-PS.4 expressing human psoriasin from amino acid residues $Ser_2$ to $Gln_{101}$ has previously been described (Hoffmann, 1994).

FIG. 25: Amino acid sequence of human psoriasin.
The predicted amino acid sequence of the full length reading frame encoding human psoriasin (SEQ ID NO: 58).

Figure 26A:
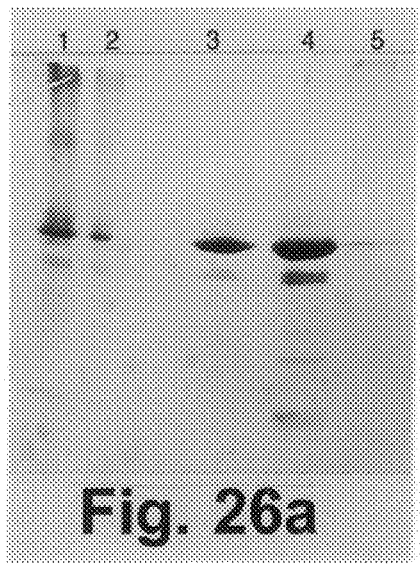
Figure 26B:
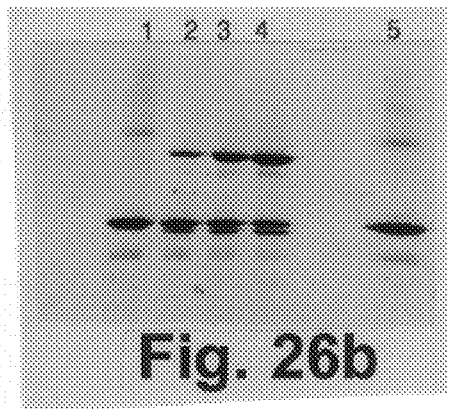

FIGS. 26a and 26b: SDS-PAGE analysis of purification and $FX_a$ cleavage of recombinant Mab 32 diabody.

FIG. 26a: Different stages of the purification
Lanes 1 and 2: Crude product from folding.
Lane 3: Final purified Mab 32 diabody fusion protein-product
Lane 4: Supernatant of crude folding product after 50-fold concentration and centrifugation.
Lane 5: Pellet from crude folding product after 50-fold concentration and centrifugation.

FIG. 26b: $FX_a$ cleavage of Mab 32 diabody fusion protein.
Lanes 1 and 5: Final purified Mab 32 diabody fusion protein
Lane 2: Molar ratio 1:5 $FX_a$:Mab 32 diabody fusion protein at 37° C. for 20 hours.
Lane 3: Molar ratio 1:2 $FX_a$:Mab 32 diabody fusion protein at 37° C. for 20 hours
Lane 4: Molar ratio 1:1 $FX_a$:Mab 32 diabody fusion protein at 37° C. for 20 hours FIG. 27: Suitability of glutathione as reducing agent in cyclic refolding of human $\beta_2$-microglobulin fusion protein.
Lane 1: Reduced sample of test no. 1.
Lane 2: Non-reduced sample of test no.1.
Lane 3: Non-reduced sample of test no.2.
Lane 4: Non-reduced sample of test no.3.
Lane 5: Non-reduced sample of test no.4.
Lane 6: Non-reduced sample of test no.5.
Lane 7: Non-reduced sample of test no.6.
Lane 8: Non-reduced sample of test no.7.
Lane 9: Non-reduced sample of test no.8.
Lane 10: Non-reduced sample of test no.9.
Lane 11: Non-reduced sample of test no.10.
Lane 12: Non-reduced sample of test no.11.

Figure 28:
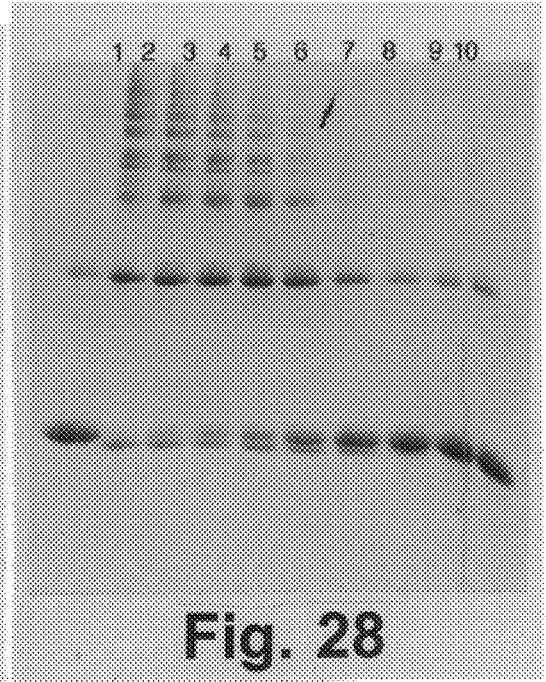

FIG. 28: Suitability of L-cysteine ethyl ester as reducing agent in cyclic refolding of human $\beta_2$-microglobulin fusion protein.
Lane 1: Reduced sample of test no. 1.
Lane 2: Non-reduced sample of test no.1.
Lane 3: Non-reduced sample of test no.2.
Lane 4: Non-reduced sample of test no.3.
Lane 5: Non-reduced sample of test no.4.
Lane 6: Non-reduced sample of test no.5.
Lane 7: Non-reduced sample of test no.6.
Lane 8: Non-reduced sample of test no.7.
Lane 9: Non-reduced sample of test no.8.
Lane 10: Non-reduced sample of test no.9.

FIG. 29: Suitability of 2-Mercaptoethanol as reducing agent in cyclic refolding of human $\beta_2$-microglobulin fusion protein.
Lane 1: Reduced sample of test no. 1.
Lane 2: Non-reduced sample of test no.1.
Lane 3: Non-reduced sample of test no.2.
Lane 4: Non-reduced sample of test no.3.
Lane 5: Non-reduced sample of test no.4.
Lane 6: Non-reduced sample of test no.5.
Lane 7: Non-reduced sample of test no.6.
Lane 8: Non-reduced sample of test no.7.
Lane 9: Non-reduced sample of test no.8.
Lane 10: Non-reduced sample of test no.9.

FIG. 30: Suitability of Mercaptosuccinic acid as reducing agent in cyclic refolding of human $\beta_2$-microglobulin fusion protein.

Lane 1: Non-reduced sample of test no.1.
Lane 2: Non-reduced sample of test no.2.
Lane 3: Non-reduced sample of test no.3.
Lane 4: Non-reduced sample of test no.4.
Lane 5: Non-reduced sample of test no.5.
Lane 6: Non-reduced sample of test no.6.
Lane 7: Non-reduced sample of test no.7.
Lane 8: Non-reduced sample of test no.8.
Lane 9: Non-reduced sample of test no.9.

Figure 31:
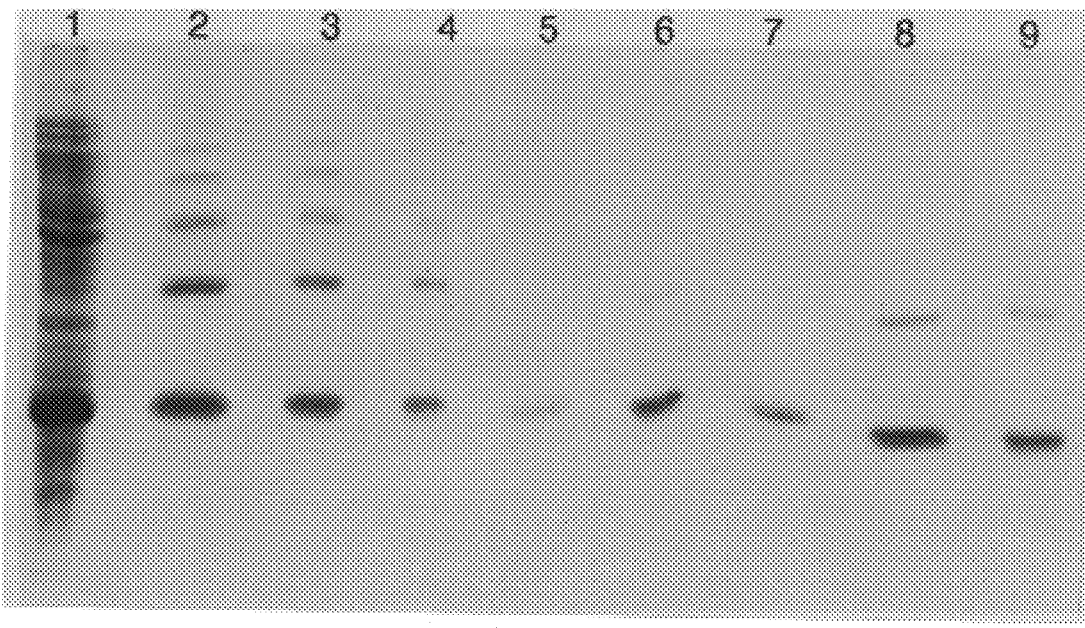

FIG. 31: SDS-PAGE analysis of cyclic refolding of human $\beta_2$-microglobulin fusion protein.
Lane 1: Crude protein extract before application to the Ni$^{2+}$NTA-agarose column (reduced sample).
Lane 2: 8 $\mu$l sample of soluble fraction of refolded h$\beta_2$m as described in EXAMPLE 1.
Lane 3: 4 $\mu$l sample of soluble fraction of refolded h$\beta_2$m as described in EXAMPLE 1.
Lane 4: 2 $\mu$l sample of soluble fraction of refolded h$\beta_2$m as described in EXAMPLE 1.
Lane 5: 8 $\mu$l sample of soluble fraction of refolded h$\beta_2$m as described in EXAMPLE 1.
Lanes 6 and 7: h$\beta_2$m final product after purification by ion exchange chromatography.
Lanes 8 and 9: Refolded h$\beta_2$m after optimized refolding protocol as described in EXAMPLE 13.

Figure 32:
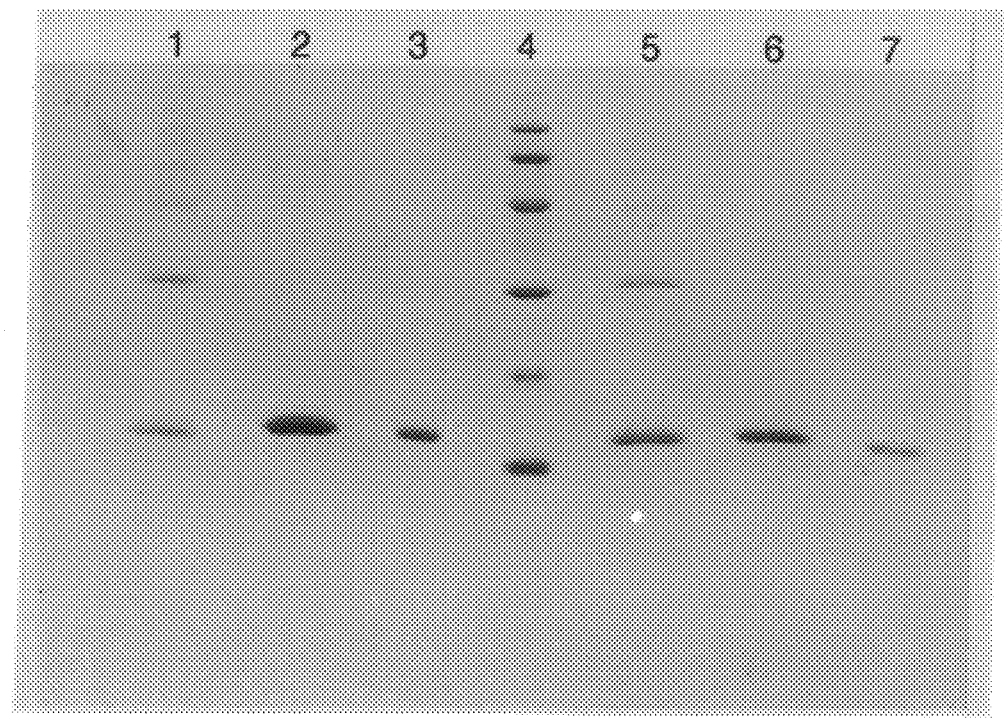

FIG. 32: SDS-PAGE analysis of refolding of human $\beta_2$-microglobulin fusion protein by buffer step and linear gradient.
Lane 1: Sample from soluble fraction of refolded h$\beta_2$m, folded by the buffer step protocol as described in EXAMPLE 13.
Lane 2 and 3: Sample of insoluble fraction of refolded h$\beta_2$m, folded by the buffer step protocol as described in EXAMPLE 13.
Lane 4: Protein molecular weight markers (Pharmacia, Sweden): From top of gel; 94 kDa, 67 kDa, 43 kDa, 30 kDa, 20.1 kDa, and 14.4 kDa (reduced sample).
Lane 5: Sample of soluble fraction of refolded h$\beta_2$m, folded by the linear gradient protocol as described in EXAMPLE 13
Lane 6 and 7: Sample of insoluble fraction of refolded h$\beta_2$m, folded by the linear gradient protocol as described in EXAMPLE 13.

Figure 33:
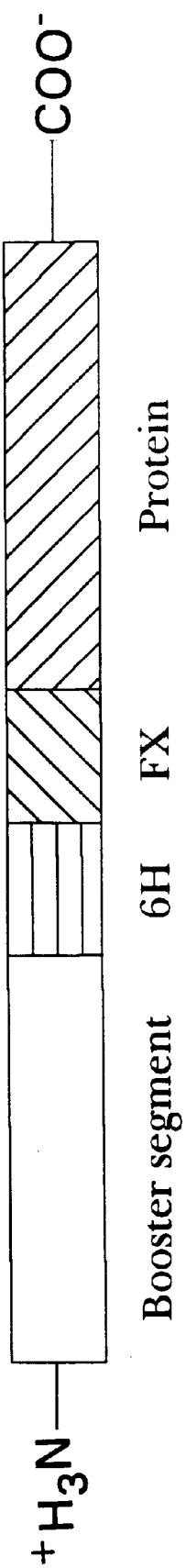

FIG. 33: The general scheme of the design of the fusion proteins described in the examples.

In the N-terminal end of the fusion protein is optionally inserted a "booster segment" enhancing the level of expression of the fusion protein in the cell expressing the DNA encoding the fusion protein. C-terminally to this, the "6H" indicates the 6 histidinyl residues which constitute an ion chelating site used as a "affinity handle" during purification and refolding of the fusion proteins. The "FX" at the C-terminal of the 6-histidinyl site is the FX$_a$ cleavage site. Finally, the part of the fusion protein denoted "protein" represents the protein which is going to be refolded according to the method of the invention.

EXAMPLES

Examples 1 to 11 given in this section, which are used to exemplify the "cyclic folding procedure", all describe the process of folding a recombinant cleavable hybrid protein (fusion protein) produced in *E. coli*, purified from a crude protein extract and subjected to folding without further purification by one general procedure.

The nucleotide sequence encoding the recombinant protein, which is to be produced, is at the 5'-end fused to a nucleotide sequence encoding an amino acid sequence specifying a FX$_a$ cleavage site (FX), in turn linked N-terminally to a segment containing six histidinyl residues (SEQ ID NO: 47). The linking of the FX$_a$ cleavage site is normally achieved during a Polymerase Chain Reaction, wherein the 5'-terminal primer comprises nucleotides encoding this sequence. The linking of the six histidinyl residues is normally obtained by employing a vector which comprises a nucleotide fragment encoding SEQ ID NO: 47. The six histidinyl residues constitute a metal ion chelating site, which is utilized as affinity handle during purification of the fusion protein and subsequently as the point of contact to the solid matrix during the cyclic folding process. Occasionally 'booster segments' (e.g. a segment derived from the N-terminus of the $\lambda$cII protein in some cases followed by a segment derived from myosin light chain) are inserted N-terminal to the affinity handle in order to improve the level of expression of the fusion protein in *E. coli*.

The fusion proteins are all designed according to the same general scheme (cf. FIG. 34). The presence of booster segments, affinity handle and FX$_a$ cleavage site might complicate refolding of the recombinant protein of interest. Furthermore, the cyclic folding process is initiated immediately after the affinity purification of the fusion protein. This means that fusion protein material, which has been partially degraded by the *E. coli* host, is retained on the affinity matrix in addition to the full length fusion protein column. This degraded fusion protein may well interfere severely with refolding of the full-length fusion protein, thereby reducing the apparent efficiency of the process. The folding efficiency results reported in Examples 1 to 11 therefore cannot directly be compared to the efficiency of the process of refolding a purified fusion protein.

Examples 1 to 11 describe the refolding procedure for 21 different proteins, protein domains or domain-clusters, ranging from a size of 82 amino acids (K1, Example 6) to 780 amino acids ($\alpha_2$MR#7, Example 4), and the number of disulphide bridges in the proteins ranges from zero ($\alpha_2$MRAP, Example 3) to 33 ($\alpha_2$MR#4, Example 4) and 36 ($\alpha_2$MR#7, Example 4).

The efficiency of the refolding of the proteins ranges from 15 to 95%, and the yield of active protein lies in the order of 10–100 mg for refolding on a 40 ml Ni+NTA-agarose column (NTA denotes a substituted nitrilotriacetic acid).

The following tables 1–5 demonstrate the gradient profiles used in the examples. "Time" is given in minutes and "flow" in ml/min.

TABLE 1

| Step | Time | Flow | % A | % B |
|---|---|---|---|---|
| 1 | 0 | 2 | 100 | 0 |
| 2 | 45 | 2 | 100 | 0 |
| 3 | 46 | 2 | 0 | 100 |
| 4 | 52 | 2 | 0 | 100 |
| 5 | 60 | 2 | 100 | 0 |
| 6 | 105 | 2 | 100 | 0 |
| 7 | 106 | 2 | 4 | 96 |
| 8 | 113 | 2 | 4 | 96 |
| 9 | 120 | 2 | 100 | 0 |
| 10 | 165 | 2 | 100 | 0 |
| 11 | 166 | 2 | 8 | 92 |
| 12 | 172 | 2 | 8 | 92 |
| 13 | 180 | 2 | 100 | 0 |
| 14 | 225 | 2 | 100 | 0 |
| 15 | 226 | 2 | 12 | 88 |
| 16 | 232 | 2 | 12 | 88 |
| 17 | 240 | 2 | 100 | 0 |
| 18 | 285 | 2 | 100 | 0 |

TABLE 1-continued

| Step | Time | Flow | % A | % B |
|---|---|---|---|---|
| 19 | 286 | 2 | 16 | 84 |
| 20 | 202 | 2 | 16 | 84 |
| 21 | 300 | 2 | 100 | 0 |
| 22 | 345 | 2 | 100 | 0 |
| 23 | 346 | 2 | 20 | 80 |
| 24 | 352 | 2 | 20 | 80 |
| 25 | 360 | 2 | 100 | 0 |
| 26 | 405 | 2 | 100 | 0 |
| 27 | 406 | 2 | 24 | 76 |
| 28 | 412 | 2 | 24 | 76 |
| 29 | 420 | 2 | 100 | 0 |
| 30 | 465 | 2 | 100 | 0 |
| 31 | 466 | 2 | 28 | 72 |
| 32 | 472 | 2 | 28 | 72 |
| 33 | 480 | 2 | 100 | 0 |
| 34 | 525 | 2 | 100 | 0 |
| 35 | 526 | 2 | 32 | 60 |
| 36 | 332 | 2 | 32 | 68 |
| 37 | 540 | 2 | 100 | 0 |
| 38 | 585 | 2 | 100 | 0 |
| 39 | 586 | 2 | 36 | 64 |
| 40 | 592 | 2 | 36 | 64 |
| 41 | 600 | 2 | 100 | 0 |
| 42 | 645 | 2 | 100 | 0 |
| 43 | 646 | 2 | 40 | 60 |
| 44 | 652 | 2 | 40 | 60 |
| 45 | 660 | 2 | 100 | 0 |
| 46 | 705 | 2 | 100 | 0 |
| 47 | 706 | 2 | 44 | 56 |
| 48 | 713 | 2 | 44 | 56 |
| 49 | 720 | 2 | 100 | 0 |
| 50 | 765 | 2 | 100 | 0 |
| 51 | 766 | 2 | 48 | 52 |
| 52 | 772 | 2 | 48 | 52 |
| 53 | 780 | 2 | 100 | 0 |
| 54 | 825 | 2 | 100 | 0 |
| 55 | 826 | 2 | 52 | 48 |
| 56 | 832 | 2 | 52 | 48 |
| 57 | 840 | 2 | 100 | 0 |
| 58 | 005 | 2 | 100 | 0 |
| 59 | 886 | 2 | 56 | 44 |
| 60 | 892 | 2 | 56 | 44 |
| 61 | 900 | 2 | 100 | 0 |
| 62 | 945 | 2 | 100 | 0 |
| 63 | 948 | 2 | 60 | 40 |
| 64 | 952 | 2 | 60 | 40 |
| 65 | 960 | 2 | 100 | 0 |
| 66 | 1005 | 2 | 100 | 0 |
| 67 | 1006 | 2 | 62 | 38 |
| 68 | 1012 | 2 | 62 | 38 |
| 69 | 1020 | 2 | 100 | 0 |
| 70 | 1065 | 2 | 100 | 0 |
| 71 | 1066 | 2 | 64 | 36 |
| 72 | 1072 | 2 | 64 | 36 |
| 73 | 1080 | 2 | 100 | 0 |
| 74 | 1125 | 2 | 100 | 0 |
| 75 | 1126 | 2 | 66 | 34 |
| 76 | 1132 | 2 | 66 | 34 |
| 77 | 1140 | 2 | 100 | 0 |
| 78 | 1185 | 2 | 100 | 0 |
| 79 | 1188 | 2 | 68 | 32 |
| 80 | 1192 | 2 | 68 | 32 |
| 81 | 1200 | 2 | 100 | 0 |
| 82 | 1245 | 2 | 100 | 0 |
| 83 | 1246 | 2 | 70 | 30 |
| 84 | 1252 | 2 | 70 | 30 |
| 85 | 1260 | 2 | 100 | 0 |
| 86 | 1305 | 2 | 100 | 0 |
| 87 | 1306 | 2 | 72 | 28 |
| 88 | 1312 | 2 | 72 | 28 |
| 89 | 1319 | 2 | 100 | 0 |
| 90 | 1364 | 2 | 100 | 0 |
| 91 | 1365 | 2 | 74 | 26 |
| 92 | 1371 | 2 | 74 | 26 |
| 93 | 1378 | 2 | 100 | 0 |
| 94 | 1423 | 2 | 100 | 0 |
| 95 | 1424 | 2 | 76 | 24 |
| 96 | 1430 | 2 | 76 | 24 |
| 97 | 1437 | 2 | 100 | 0 |
| 98 | 1482 | 2 | 100 | 0 |
| 99 | 1483 | 2 | 78 | 22 |
| 100 | 1489 | 2 | 78 | 22 |
| 101 | 1456 | 2 | 100 | 0 |
| 102 | 1541 | 2 | 100 | 0 |
| 103 | 1542 | 2 | 80 | 20 |
| 104 | 1540 | 2 | 80 | 20 |
| 105 | 1555 | 2 | 100 | 0 |
| 106 | 1556 | 2 | 82 | 18 |
| 107 | 1562 | 2 | 82 | 18 |
| 108 | 1569 | 2 | 100 | 0 |
| 109 | 1614 | 2 | 100 | 0 |
| 110 | 1615 | 2 | 84 | 16 |
| 111 | 1621 | 2 | 84 | 16 |
| 112 | 1628 | 2 | 100 | 0 |
| 113 | 1673 | 2 | 100 | 0 |
| 114 | 1674 | 2 | 88 | 12 |
| 115 | 1732 | 2 | 88 | 12 |
| 116 | 1733 | 2 | 100 | 0 |
| 117 | 1778 | 2 | 100 | 0 |

TABLE 2

| Step | Time | Flow | % A | % B |
|---|---|---|---|---|
| 1 | 0 | 2 | 100 | 0 |
| 2 | 45 | 2 | 100 | 0 |
| 3 | 46 | 2 | 0 | 100 |
| 4 | 52 | 2 | 0 | 100 |
| 5 | 60 | 2 | 100 | 0 |
| 6 | 105 | 2 | 100 | 0 |
| 7 | 106 | 2 | 8 | 92 |
| 8 | 113 | 2 | 8 | 92 |
| 9 | 120 | 2 | 100 | 0 |
| 10 | 165 | 2 | 100 | 0 |
| 11 | 166 | 2 | 20 | 80 |
| 12 | 172 | 2 | 20 | 80 |
| 13 | 180 | 2 | 100 | 0 |
| 14 | 225 | 2 | 100 | 0 |
| 15 | 228 | 2 | 28 | 72 |
| 16 | 232 | 2 | 28 | 72 |
| 17 | 240 | 2 | 100 | 0 |
| 18 | 285 | 2 | 100 | 0 |
| 19 | 286 | 2 | 34 | 66 |
| 20 | 292 | 2 | 34 | 66 |
| 21 | 300 | 2 | 100 | 0 |
| 22 | 345 | 2 | 100 | 0 |
| 23 | 346 | 2 | 42 | 58 |
| 24 | 252 | 2 | 42 | 58 |
| 25 | 360 | 2 | 100 | 0 |
| 26 | 405 | 2 | 100 | 0 |
| 27 | 406 | 2 | 50 | 50 |
| 28 | 412 | 2 | 50 | 50 |
| 29 | 420 | 2 | 100 | 0 |
| 30 | 465 | 2 | 100 | 0 |
| 31 | 466 | 2 | 54 | 46 |
| 32 | 472 | 2 | 54 | 46 |
| 33 | 480 | 2 | 100 | 0 |
| 34 | 525 | 2 | 100 | 0 |
| 35 | 526 | 2 | 58 | 42 |
| 36 | 532 | 2 | 58 | 42 |
| 37 | 540 | 2 | 100 | 0 |
| 38 | 585 | 2 | 100 | 0 |
| 39 | 586 | 2 | 62 | 38 |
| 40 | 502 | 2 | 62 | 38 |
| 41 | 600 | 2 | 100 | 0 |
| 42 | 645 | 2 | 100 | 0 |
| 43 | 646 | 2 | 66 | 34 |
| 44 | 632 | 2 | 66 | 34 |
| 45 | 660 | 2 | 100 | 0 |
| 46 | 705 | 2 | 100 | 0 |
| 47 | 706 | 2 | 70 | 30 |

TABLE 2-continued

| Step | Time | Flow | % A | % B |
|---|---|---|---|---|
| 48 | 713 | 2 | 70 | 30 |
| 49 | 720 | 2 | 100 | 0 |
| 50 | 765 | 2 | 100 | 0 |
| 51 | 766 | 2 | 74 | 26 |
| 52 | 772 | 2 | 74 | 26 |
| 53 | 780 | 2 | 100 | 0 |
| 54 | 825 | 2 | 100 | 0 |
| 55 | 826 | 2 | 76 | 24 |
| 56 | 832 | 2 | 76 | 24 |
| 57 | 840 | 2 | 100 | 0 |
| 58 | 885 | 2 | 100 | 0 |
| 59 | 886 | 2 | 78 | 22 |
| 60 | 892 | 2 | 78 | 22 |
| 61 | 900 | 2 | 100 | 0 |
| 62 | 945 | 2 | 100 | 0 |
| 63 | 946 | 2 | 80 | 20 |
| 64 | 952 | 2 | 80 | 20 |
| 65 | 960 | 2 | 100 | 0 |
| 66 | 1005 | 2 | 100 | 0 |
| 67 | 1006 | 2 | 82 | 18 |
| 68 | 1012 | 2 | 82 | 18 |
| 69 | 1020 | 2 | 100 | 0 |
| 70 | 1065 | 2 | 100 | 0 |
| 71 | 1066 | 2 | 84 | 16 |
| 72 | 1072 | 2 | 84 | 16 |
| 73 | 1080 | 2 | 100 | 0 |
| 74 | 1125 | 2 | 100 | 0 |
| 75 | 1126 | 2 | 86 | 14 |
| 76 | 1132 | 2 | 86 | 14 |
| 77 | 1140 | 2 | 100 | 0 |
| 78 | 1185 | 2 | 100 | 0 |
| 79 | 1186 | 2 | 88 | 12 |
| 80 | 1192 | 2 | 88 | 12 |
| 81 | 1200 | 2 | 100 | 0 |
| 82 | 1245 | 2 | 100 | 0 |
| 83 | 1246 | 2 | 90 | 10 |
| 84 | 1252 | 2 | 90 | 10 |
| 85 | 1260 | 2 | 100 | 0 |
| 86 | 1305 | 2 | 100 | 0 |
| 87 | 1306 | 2 | 95 | 5 |
| 88 | 1312 | 2 | 95 | 5 |
| 89 | 1319 | 2 | 100 | 0 |
| 90 | 1364 | 2 | 100 | 0 |

TABLE 3

| Step | Time | Flow | % A | % B |
|---|---|---|---|---|
| 1 | 0.0 | 1.0 | 0.0 | 100.0 |
| 2 | 10.0 | 1.0 | 0.0 | 100.0 |
| 3 | 40.0 | 1.0 | 100.0 | 0.0 |
| 4 | 70.0 | 1.0 | 100.0 | 0.0 |
| 5 | 70.5 | 1.0 | 10.0 | 90.0 |
| 6 | 80.0 | 1.0 | 10.0 | 90.0 |
| 7 | 110.0 | 1.0 | 100.0 | 0.0 |
| 8 | 140.0 | 1.0 | 100.0 | 0.0 |
| 9 | 140.5 | 1.0 | 20.0 | 80.0 |
| 10 | 150.0 | 1.0 | 20.0 | 80.0 |
| 11 | 100.0 | 1.0 | 100.0 | 0.0 |
| 12 | 210.0 | 1.0 | 100.0 | 0.0 |
| 13 | 210.5 | 1.0 | 30.0 | 70.0 |
| 14 | 220.0 | 1.0 | 90.0 | 70.0 |
| 15 | 250.0 | 1.0 | 100.0 | 0.0 |
| 16 | 280.0 | 1.0 | 100.0 | 0.0 |
| 17 | 280.5 | 1.0 | 40.0 | 60.0 |
| 18 | 290.0 | 1.0 | 40.0 | 60.0 |
| 19 | 320.0 | 1.0 | 100.0 | 0.0 |
| 20 | 350.0 | 1.0 | 100.0 | 0.0 |
| 21 | 350.5 | 1.0 | 50.0 | 50.0 |
| 22 | 360.0 | 1.0 | 50.0 | 50.0 |
| 23 | 390.0 | 1.0 | 100.0 | 0.0 |
| 24 | 420.0 | 1.0 | 100.0 | 0.0 |
| 25.0 | 420.5 | 1.0 | 60.0 | 40.0 |
| 26.0 | 430.0 | 1.0 | 60.0 | 40.0 |
| 27.0 | 460.0 | 1.0 | 100.0 | 0.0 |
| 28.0 | 400.0 | 1.0 | 100.0 | 0.0 |
| 29.0 | 490.5 | 1.0 | 70.0 | 30.0 |
| 30.0 | 500.0 | 1.0 | 70.0 | 30.0 |
| 31.0 | 530.0 | 1.0 | 100.0 | 0.0 |
| 32.0 | 560.0 | 1.0 | 100.0 | 0.0 |
| 33.0 | 560.5 | 1.0 | 80.0 | 20.0 |
| 34.0 | 570.0 | 1.0 | 80.0 | 20.0 |
| 35.0 | 600.0 | 1.0 | 100.0 | 0.0 |
| 36.0 | 630.0 | 1.0 | 100.0 | 0.0 |
| 37.0 | 630.5 | 1.0 | 85.0 | 15.0 |
| 38.0 | 640.0 | 1.0 | 85.0 | 15.0 |
| 39.0 | 670.0 | 1.0 | 100.0 | 0.0 |
| 40.0 | 700.0 | 1.0 | 100.0 | 0.0 |
| 41.0 | 700.5 | 1.0 | 88.0 | 12.0 |
| 42.0 | 710.0 | 1.0 | 88.0 | 12.0 |
| 43.0 | 740.0 | 1.0 | 100.0 | 0.0 |
| 44.0 | 770.0 | 1.0 | 100.0 | 0.0 |
| 45.0 | 770.5 | 1.0 | 90.0 | 10.0 |
| 46.0 | 780.0 | 1.0 | 90.0 | 10.0 |
| 47.0 | 810.0 | 1.0 | 100.0 | 0.0 |
| 48.0 | 850.0 | 1.0 | 100.0 | 0.0 |

TABLE 4

| Step | Time | Flow | % A | % B |
|---|---|---|---|---|
| 1 | 0 | 2 | 100 | 0 |
| 2 | 45 | 2 | 100 | 0 |
| 3 | 46 | 2 | 0 | 100 |
| 4 | 52 | 2 | 0 | 100 |
| 5 | 60 | 2 | 100 | 0 |
| 6 | 105 | 2 | 100 | 0 |
| 7 | 106 | 2 | 4 | 96 |
| 8 | 113 | 2 | 4 | 96 |
| 9 | 120 | 2 | 100 | 0 |
| 10 | 165 | 2 | 100 | 0 |
| 11 | 166 | 2 | 8 | 92 |
| 12 | 172 | 2 | 8 | 92 |
| 13 | 180 | 2 | 100 | 0 |
| 14 | 225 | 2 | 100 | 0 |
| 15 | 226 | 2 | 12 | 88 |
| 16 | 232 | 2 | 12 | 88 |
| 17 | 240 | 2 | 100 | 0 |
| 18 | 285 | 2 | 100 | 0 |
| 19 | 288 | 2 | 16 | 84 |
| 20 | 292 | 2 | 16 | 84 |
| 21 | 300 | 2 | 100 | 0 |
| 22 | 343 | 2 | 100 | 0 |
| 23 | 346 | 2 | 20 | 80 |
| 24 | 352 | 2 | 20 | 80 |
| 25 | 360 | 2 | 100 | 0 |
| 26 | 405 | 2 | 100 | 0 |
| 27 | 406 | 2 | 24 | 76 |
| 28 | 412 | 2 | 24 | 76 |
| 29 | 420 | 2 | 100 | 0 |
| 30 | 465 | 2 | 100 | 0 |
| 31 | 466 | 2 | 28 | 72 |
| 32 | 472 | 2 | 28 | 72 |
| 33 | 480 | 2 | 100 | 0 |
| 34 | 525 | 2 | 100 | 0 |
| 35 | 526 | 2 | 32 | 68 |
| 36 | 532 | 2 | 32 | 68 |
| 37 | 540 | 2 | 100 | 0 |
| 38 | 585 | 2 | 100 | 0 |
| 39 | 586 | 2 | 36 | 64 |
| 40 | 592 | 2 | 36 | 64 |
| 41 | 600 | 2 | 100 | 0 |
| 42 | 645 | 2 | 100 | 0 |
| 43 | 646 | 2 | 40 | 60 |
| 44 | 652 | 2 | 40 | 60 |
| 45 | 660 | 2 | 100 | 0 |
| 46 | 705 | 2 | 100 | 0 |
| 47 | 705 | 2 | 44 | 56 |

TABLE 4-continued

| Step | Time | Flow | % A | % B |
|---|---|---|---|---|
| 48 | 719 | 2 | 44 | 56 |
| 49 | 720 | 2 | 100 | 0 |
| 50 | 765 | 2 | 100 | 0 |
| 51 | 766 | 2 | 48 | 52 |
| 52 | 772 | 2 | 48 | 52 |
| 53 | 780 | 2 | 100 | 0 |
| 54 | 825 | 2 | 100 | 0 |
| 55 | 826 | 2 | 52 | 48 |
| 56 | 832 | 2 | 52 | 48 |
| 57 | 840 | 2 | 100 | 0 |
| 58 | 885 | 2 | 100 | 0 |
| 59 | 886 | 2 | 56 | 44 |
| 60 | 892 | 2 | 56 | 44 |
| 61 | 900 | 2 | 100 | 0 |
| 62 | 945 | 2 | 100 | 0 |
| 63 | 946 | 2 | 60 | 40 |
| 64 | 952 | 2 | 60 | 40 |
| 65 | 960 | 2 | 100 | 0 |
| 66 | 1005 | 2 | 100 | 0 |
| 67 | 1006 | 2 | 64 | 36 |
| 68 | 1012 | 2 | 64 | 36 |
| 69 | 1020 | 2 | 100 | 0 |
| 70 | 1065 | 2 | 100 | 0 |
| 71 | 1066 | 2 | 68 | 32 |
| 72 | 1072 | 2 | 68 | 32 |
| 73 | 1080 | 2 | 100 | 0 |
| 74 | 1125 | 2 | 100 | 0 |
| 75 | 1126 | 2 | 70 | 30 |
| 76 | 1132 | 2 | 70 | 30 |
| 77 | 1140 | 2 | 100 | 0 |
| 78 | 1185 | 2 | 100 | 0 |
| 79 | 1186 | 2 | 72 | 28 |
| 80 | 1192 | 2 | 72 | 28 |
| 81 | 1200 | 2 | 100 | 0 |
| 82 | 1245 | 2 | 100 | 0 |
| 83 | 1246 | 2 | 75 | 25 |
| 84 | 1252 | 2 | 75 | 25 |
| 85 | 1260 | 2 | 100 | 0 |
| 86 | 1305 | 2 | 100 | 0 |
| 87 | 1306 | 2 | 80 | 20 |
| 88 | 1312 | 2 | 80 | 20 |
| 89 | 1319 | 2 | 100 | 0 |
| 90 | 1364 | 2 | 100 | 0 |
| 91 | 1365 | 2 | 85 | 15 |
| 92 | 1371 | 2 | 85 | 15 |
| 93 | 1378 | 2 | 100 | 0 |
| 94 | 1423 | 2 | 100 | 0 |

TABLE 5

| Step | Time | Flow | % A | % B |
|---|---|---|---|---|
| 1 | 0 | 2 | 100 | 0 |
| 2 | 45 | 2 | 100 | 0 |
| 3 | 46 | 2 | 0 | 100 |
| 4 | 52 | 2 | 0 | 100 |
| 5 | 60 | 2 | 100 | 0 |
| 6 | 105 | 2 | 100 | 0 |
| 7 | 106 | 2 | 13 | 87 |
| 8 | 113 | 2 | 13 | 87 |
| 9 | 120 | 2 | 100 | 0 |
| 10 | 165 | 2 | 100 | 0 |
| 11 | 166 | 2 | 25 | 75 |
| 12 | 172 | 2 | 25 | 75 |
| 13 | 180 | 2 | 100 | 0 |
| 14 | 225 | 2 | 100 | 0 |
| 15 | 226 | 2 | 29 | 71 |
| 16 | 232 | 2 | 29 | 71 |
| 17 | 240 | 2 | 100 | 0 |
| 18 | 285 | 2 | 100 | 0 |
| 19 | 286 | 2 | 34 | 66 |
| 20 | 292 | 2 | 34 | 66 |
| 21 | 300 | 2 | 100 | 0 |
| 22 | 345 | 2 | 100 | 0 |

TABLE 5-continued

| Step | Time | Flow | % A | % B |
|---|---|---|---|---|
| 23 | 346 | 2 | 38 | 62 |
| 24 | 352 | 2 | 38 | 62 |
| 25 | 360 | 2 | 100 | 0 |
| 26 | 405 | 2 | 100 | 0 |
| 27 | 406 | 2 | 40 | 60 |
| 28 | 412 | 2 | 40 | 60 |
| 29 | 420 | 2 | 100 | 0 |
| 30 | 465 | 2 | 100 | 0 |
| 31 | 466 | 2 | 42 | 58 |
| 32 | 472 | 2 | 42 | 58 |
| 33 | 480 | 2 | 100 | 0 |
| 34 | 525 | 2 | 100 | 0 |
| 35 | 526 | 2 | 44 | 56 |
| 36 | 532 | 2 | 44 | 56 |
| 37 | 540 | 2 | 100 | 0 |
| 38 | 585 | 2 | 100 | 0 |
| 39 | 586 | 2 | 46 | 54 |
| 40 | 592 | 2 | 48 | 54 |
| 41 | 600 | 2 | 100 | 0 |
| 42 | 645 | 2 | 100 | 0 |
| 43 | 646 | 2 | 48 | 52 |
| 44 | 652 | 2 | 48 | 52 |
| 45 | 660 | 2 | 100 | 0 |
| 46 | 705 | 2 | 100 | 0 |
| 47 | 706 | 2 | 50 | 50 |
| 48 | 713 | 2 | 50 | 50 |
| 49 | 720 | 2 | 100 | 0 |
| 50 | 765 | 2 | 100 | 0 |
| 51 | 766 | 2 | 52 | 48 |
| 52 | 772 | 2 | 52 | 48 |
| 53 | 780 | 2 | 100 | 0 |
| 54 | 825 | 2 | 100 | 0 |
| 55 | 826 | 2 | 54 | 46 |
| 56 | 832 | 2 | 54 | 46 |
| 57 | 840 | 2 | 100 | 0 |
| 58 | 885 | 2 | 100 | 0 |
| 59 | 886 | 2 | 56 | 44 |
| 60 | 892 | 2 | 56 | 44 |
| 61 | 900 | 2 | 100 | 0 |
| 62 | 945 | 2 | 100 | 0 |
| 63 | 946 | 2 | 58 | 42 |
| 64 | 952 | 2 | 58 | 42 |
| 65 | 960 | 2 | 100 | 0 |
| 66 | 1005 | 2 | 100 | 0 |
| 67 | 1006 | 2 | 60 | 40 |
| 68 | 1012 | 2 | 60 | 40 |
| 69 | 1020 | 2 | 100 | 0 |
| 70 | 1065 | 2 | 100 | 0 |
| 71 | 1066 | 2 | 62 | 38 |
| 72 | 1072 | 2 | 62 | 38 |
| 73 | 1080 | 2 | 100 | 0 |
| 74 | 1125 | 2 | 100 | 0 |
| 75 | 1126 | 2 | 66 | 34 |
| 76 | 1132 | 2 | 66 | 34 |
| 77 | 1140 | 2 | 100 | 0 |
| 78 | 1185 | 2 | 100 | 0 |
| 79 | 1186 | 2 | 70 | 30 |
| 80 | 1102 | 2 | 70 | 30 |
| 81 | 1200 | 2 | 100 | 0 |
| 82 | 1245 | 2 | 100 | 0 |
| 83 | 1246 | 2 | 74 | 26 |
| 84 | 1232 | 2 | 74 | 26 |
| 85 | 1260 | 2 | 100 | 0 |
| 86 | 1305 | 2 | 100 | 0 |
| 87 | 1306 | 2 | 78 | 22 |
| 88 | 1312 | 2 | 78 | 22 |
| 89 | 1319 | 2 | 100 | 0 |
| 90 | 1364 | 2 | 100 | 0 |
| 91 | 1365 | 2 | 82 | 18 |
| 92 | 1371 | 2 | 82 | 18 |
| 93 | 1378 | 2 | 100 | 0 |
| 94 | 1423 | 2 | 100 | 0 |

Example 1

Production and Folding of Human and Murine $\beta_2$-microglobulin

This example describes the production in *E. coli* of both human $\beta_2$-microglobulin and murine $\beta_2$-microglobulin as $FX_a$ cleavable fusion proteins, and the purification of the recombinant human and murine $\beta_2$-microglobulin after $FX_a$ cleavage.

Plasmid clones containing the full length cDNAs encoding the human and the murine $\beta_2$-microglobulin proteins (generously provided by Dr. David N. Garboczi to Dr. Søren Buus) were used as templates in a Polymerase Chain Reaction (PCR) (Saiki et al., 1988) designed to produce cDNA fragments corresponding to the mature human (corresponding to amino acid residue $Ile_1$ to $Met_{99}$) and the mature murine (corresponding to amino acid residue $Ile_1$ to $Met_{99}$) $\beta_2$-microglobulin proteins, by use of the primers SEQ ID NO: 3 and SEQ ID NO: 4 (for the human $\beta_2$-microglobulin) and SEQ ID NO: 5 and SEQ ID NO: 6 (for the murine $\beta_2$-microglobulin). The amplified coding reading frames were at their 5'-ends, via the PCR-reaction, linked to nucleotide sequences, included in SEQ ID NO: 3 and 5, encoding the amino acid sequence SEQ ID NO: 37, which constitute a cleavage site for the bovine restriction protease $FX_a$ (Nagai and Thøgersen, 1987). The amplified DNA fragments were subcloned into the *E. coli* expression vector $pT_7H_6$ (Christensen et al., 1991). The construction of the resulting plasmids $pT_7H_6FX$-h$\beta_2$m (expressing human $\beta_2$-microglobulin) and $pT_7H_6FX$-m$\beta_2$m (expressing murine $\beta_2$-microglobulin) is outlined in FIG. 2 and in FIG. 3 is shown the amino acid sequences of the expressed proteins (SEQ ID NO: 49 (human) and SEQ ID NO: 50 (murine)).

Human and murine $\beta_2$ microglobulin were produced by growing and expressing the plasmids $pT_7H_6FX$-h$\beta_2$m and -m$\beta_2$m in *E. coli* BL21 cells in a medium scale (2×1 liter) as described by Studier and Moffat, J. Mol. Biol., 189: 113–130, 1986. Exponentially growing cultures at 37° C. were at $OD_{600}$ 0.8 infected with bacteriophage λCE6 at a multiplicity of approximately 5. Cultures were grown at 37° C. for another three hours before cells were harvested by centrifugation. Cells were lysed by osmotic shock and sonication and total cellular protein extracted into phenol (adjusted to pH 8 with Trisma base). Protein was precipitated from the phenol phase by addition of 2.5 volumes of ethanol and centrifugation. The protein pellet was dissolved in a buffer containing 6 M guanidinium chloride, 50 mM Tris-HCl pH 8 and 0.1 M dithioerythriol. Following gel filtration on Sephadex G-25 (Pharmacia, LKB, Sweden) into 8 M Urea, 1 M NaCl, 50 mM Tris-HCl pH 8, 10 mM 2-mercaptoethanol and 3 mM methionine the crude protein preparation was applied to $Ni^{2+}$ activated NTA-agarose columns for purification (Hochuli et al., 1988.) of the fusion proteins, MGSHHHHHHGSIEGR-human and murine $\beta_2$-microglobulin (wherein MGSHHHHHHGSIEGR is SEQ ID NO: 48) respectively and subsequently to undergo the cyclic folding procedure.

All buffers prepared for liquid chromatography were degassed under vacuum prior to addition of reductant and/or use.

$Ni^{2+}$ activated NTA-agarose matrix ($Ni^{2+}$NTA-agarose) is commercially available from Diagen GmbH, Germany. During the course of this work it was found, however, that this commercial product did not perform as well as expected. Our observations were, that the commercial $Ni^{2+}$NTA-agarose matrix was easily blocked when applying the denatured and reduced total protein extract, that the capacity for fusion protein was lower than expected, and that the matrix could only be regenerated successfully a few times over.

In order to improve the performance of the $Ni^{2+}$NTA-agarose it was decided to perform a carbodiimide coupling of the N-(5-amino-1-carboxypentyl)iminodiacetic acid metal ligand (synthesis route as described by Dōbeli & Hochuli (EPO 0253 303)) to a more rigid agarose matrix (i.e. Sepharose CL-6B, Pharmacia, Sweden):

8 g. of N-(5-amino-1-carboxypentyl)iminodiacetic acid from the synthesis procedure in 50 ml was adjusted to pH 10 by addition of 29 g. of $Na_2CO_3(10\ H_2O)$ and added to a stirred suspension of activated Sepharose CL-6B in 1 M $Na_2CO_3$. Reaction was allowed overnight.

The Sepharose CL-6B (initially 100 ml. suspension) was activated after removal of water by acetone with 7 g. of 1,1'-carbonyldiimidazol under stirring for 15 to 30 min. Upon activation the Sepharose CL-6B was washed with acetone followed by water and 1 M $Na_2CO_3$. The NTA-agarose matrix was loaded into a column and "charged" with $Ni^{2+}$ by slowly passing through 5 column volumes of a 10% $NiSO_4$ solution. The amount of $Ni^{2+}$ on the NTA-agarose matrix, prepared by this procedure, has been determined to 14 μmoles per ml matrix. The $Ni^{2+}$NTA-agarose matrix was packed in a standard class column for liquid chromatography (internal diameter: 2.6·cm) to a volume of 40 ml. After charging the $Ni^{2+}$NTA-agarose column was washed with two column volumes of water, one column volume of 1 M Tris-HCl pH 8 and two column volumes of loading buffer before application of the crude protein extract.

Upon application of the crude protein extracts on the $Ni^{2+}$NTA-agarose column, the fusion proteins, MGSHHHHHHGSIEGR-h$\beta_2$m and MGSHHHHHHGSIEGR-m$\beta_2$m (wherein MGSHHHHH-HGSIEGR is SEQ ID NO: 48) respectively, were purified from the majority of coli and λ phage proteins by washing with one column volume of the loading buffer followed by 6 M guanidinium chloride, 50 mM Tris-HCl, 10 mM 2-mercaptoethanol, and 3 mM methionine until the optical density (OD) at 280 nm of the column eluates were stable.

The fusion proteins were refolded on the $Ni^{2+}$NTA-agarose column using a gradient manager profile as described in table 1 and 0.5 M NaCl, 50 mM Tris-HCl pH 8, and 1.2 mM/0.4 mM reduced/oxidized glutathione as buffer A and 8 M urea, 0.5 M NaCl, 50 mM Tris-HCl pH 8, 3 mM methionine, and 6 mM reduced glutathione as buffer B. The reduced/oxidized glutathione solution was freshly prepared as a 200 times stock solution by addition of 9.9 M $H_2O_2$ to a stirred solution of 0.2 M reduced glutathione before addition to buffer A.

After completion of the cyclic folding procedure the h$\beta_2$m and m$\beta_2$m fusion proteins were eluted from the $Ni^{2+}$NTA-agarose columns with a buffer containing 0.5 M NaCl, 50 mM Tris-HCl, 20 mM EDTA pH 8.

Fusion protein that were aggregated and precipitated on the $Ni^{2+}$NTA-agarose columns were eluted in buffer B. Approximately 75% of the fusion protein material was eluted by non-denaturing elution buffer (see FIG. 16, lanes 2 and 3).

As judged by non-reducing SDS-PAGE analysis approximately 70% of the soluble h$\beta_2$m fusion protein material (corresponding to 40 mg of h$\beta_2$m fusion protein) appeared monomeric (see FIG. 15, lanes 5 and 3) whereas 25% of the m$\beta_2$m fusion protein appeared monomeric (corresponding to 20 mg of m$\beta_2$m fusion protein). The overall efficiency of the folding procedure are therefore approximately 50% for the h$\beta_2$m fusion protein and less than 20% for the m$\beta_2$m fusion protein.

Monomeric hβ$_2$m and mβ$_2$m fusion proteins were purified from dimer and higher order multimers by ion exchange chromatography on S-Sepharose (Pharmacia, Sweden): The fusion proteins eluted by the non denaturing elution buffer (approximately 70% of the fusion protein material) was gelfiltrated into a buffer containing 5 mM NaCl and 5 mM Tris-HCl pH 8 on Sephadex G-25 and diluted 1:1 with water before applied onto the S-Sepharose ion exchange columns. Fusion proteins were eluted over 5 column volumes with a liner gradient from 2.5 mM NaCl, 2.5 mM Tris-Hcl pH 8 to 100 mM NaCl, 25 mM Tris-Hcl pH 8. The monomeric hβ$_2$m as well as mβ$_2$m fusion proteins eluted in the very beginning of the gradient, whereas dimers and higher order multimers eluted later. Fractions containing the monomeric fusion proteins were diluted with water and reloaded onto the S-Sepharose columns and one-step eluted in 1 M NaCl, 50 mM Tris-HCl pH 8.

The monomeric fusion proteins were cleaved with the restriction protease FX$_a$ overnight at room temperature in a weight to weight ratio of approximately 200 to one.

After cleavage the recombinant hβ$_2$m and mβ$_2$m proteins were purified from the N terminal fusion tail, liberated from the cleaved fusion protein and FX$_a$ by ion exchange chromatography on Q-Sepharose columns (Pharmacia, Sweden): Upon gelfiltration on Sephadex G-25 into 5 mM NaCl, 5 mM Tris-HCl pH 8 and 1:1 dilution with water, recombinant hβ$_2$m and mβ$_2$m were eluted in a linear gradient (over 5 column volumes) from 2.5 mM NaCl, 2.5 mM Tris-HCl pH 8 to 100 mM NaCl, 25 mM Tris-HCl pH 8. Fractions containing the cleaved recombinant proteins were diluted with water and reloaded to the Q-Sepharose columns and one-step eluted in 1 M NaCl, 50 mM Tris-HCl pH 8. Recombinant hβ$_2$m and mβ$_2$m proteins were gelfiltrated into freshly prepared 20 mM NH$_4$HCO$_3$ and lyophilized twice.

SDS-PAGE analysis of the production of recombinant human β$_2$-microglobulin is presented in FIG. 15.

The yield of fully processed recombinant human β$_2$-microglobulin produced by this procedure was 30 mg.

The yield of fully processed recombinant murine β$_2$-microglobulin produced by this procedure was 10 mg.

Comparison of recombinant human with purified natural human β$_2$-microglobulin β$_2$-microglobulin was kindly carried out by Dr. Søren Buus in two different assays:

1. It was found that Recombinant human β$_2$-microglobulin and natural human β$_2$-microglobulin reacted with both a monoclonal- and a monospecific antibody with identical affinity.

2. Recombinant human β$_2$-microglobulin and natural human β$_2$-microglobulin were in an binding inhibition experiment using radiolabelled ligands found to bind natural affinity purified heavy chain class I K$^d$ molecules with an identical affinity.

Recombinant murine β$_2$-microglobulin was found to bind natural class I heavy chain molecules with an affinity 5 times lower than the human β$_2$-microglobulin. This result is in good agreement with previous results from the literature using natural material.

Example 3

Production and folding of Human Growth Hormone (Somatotropin)

This example describes the production in E. coli of human growth hormone (hGH) as a FX$_a$ cleavable fusion protein, and the purification of the recombinant hGH after FX$_a$ cleavage.

A plasmid clone containing the cDNA encoding the hGH (generously provided by Dr. Henrik Dalbøge (Dalbøge et al., 1987) were used as template in a Polymerase Chain Reaction (PCR) (Saiki et al., 1988), using the primers SEQ ID NO: 7 and SEQ ID NO: 8, designed to produce a cDNA fragment corresponding to the mature hGH (corresponding to amino acid residue Phe$_1$ to Phe$_{191}$) protein. The amplified coding reading frame was at the 5'-end, via the PCR-reaction, linked to a nucleotide sequence, included in SEQ ID NO: 7, encoding the amino acid sequence SEQ ID NO: 37 which constitute a cleavage site for the bovine restriction protease FX$_a$ (Nagai and Thøgersen, 1987). The amplified DNA fragment was subcloned into the E. coli expression vector pT$_7$H$_6$ (Christensen et al., 1991). The construction of the resulting plasmid pT$_7$H$_6$FX-hGH (expressing human Growth Hormone) is outlined in FIG. 4 and in FIG. 5 is shown the amino acid sequence of the expressed protein (SEQ ID NO: 51).

Recombinant human Growth Hormone was produced by growing and expressing the plasmid pT$_7$H$_6$FX-hGH in E. coli BL21 cells in a medium scale (2×1 liter) as described by Studier and Moffat, J. Mol. Biol., 189: 113–130, 1986. Exponentially growing cultures at 37° C. were at OD$_{600}$ 0.8 infected with bacteriophage λCE6 at a multiplicity of approximately 5. Cultures were grown at 37° C. for another three hours before cells were harvested by centrifugation. Cells were lysed by osmotic shock and sonification and total cellular protein extracted into phenol (adjusted to pH 8 with Trisma base). Protein was precipitated from the phenol phase by addition of 2.5 volumes of ethanol and centrifugation. The protein pellet was dissolved in a buffer containing 6 M guanidinium chloride, 50 mM Tris-HCl pH 8 and 50 mM dithioerythriol. Following gel filtration on Sephadex G-25 (Pharmacia, LKB, Sweden) into 8 M Urea, 1 M NaCl, 50 mM Tris HCl pH 8, 5 mM 2-mercaptoethanol and 1 mM methionine the crude protein preparation was applied to a Ni$^{2+}$ activated NTA-agarose column (Ni$^{2+}$NTA-agarose) for purification (Hochuli et al., 1988) of the fusion protein, MGSHHHHHHGSIEGR-hGH (wherein MGSHHHHHHG-SIEGR is SEQ ID NO: 48) and subsequently to undergo the cyclic folding procedure.

Preparation and "charging" of the Ni$^{2+}$NTA-agarose column is described under Example 1.

All buffers prepared for liquid chromatography were degassed under vacuum prior to addition of reductant and/or use.

Upon application of the crude protein extract on the Ni$^{2+}$NTA-agarose column, the fusion protein, MGSHHHHHHGSIEGR-hGH (wherein MGSHHHHHHG-SIEGR is SEQ ID NO: 48) was purified from the majority of E. coli and λ phage proteins by washing with one column volume of the loading buffer followed by 6 M guanidinium chloride, 50 mM Tris-HCl, 5 mM 2 mercaptoethanol, and 1 mM methionine until the optical density (OD) at 280 nm of the eluate was stable.

The fusion protein was refolded on the Ni$^{2+}$NTA-agarose column using a gradient manager profile as described in table 2 and 0.5 M NaCl, 50 mM Tris-HCl pH 8, and 1.0 mM/0.1 mM reduced/oxidized glutathione as buffer A and 8 M urea, 0.5 M NaCl, 50 mM Tris-HCl pH 8, 1 mM methionine, and 5 mM reduced glutathione as buffer B. The reduced/oxidized glutathione solution was freshly prepared as a 200 times stock solution by addition of 9.9 M H$_2$O$_2$ to a stirred solution of 0.2 M reduced glutathione before addition to buffer A.

After completion of the cyclic folding procedure the hGH fusion protein was eluted from the Ni$^{2+}$NTA-agarose column with a buffer containing 0.5 M NaCl, 50 mM Tris-HCl, 20 mM EDTA pH 8. Fusion protein that was aggregated and precipitated on the $Ni^{2+}$NTA-agarose column was eluted in buffer B.

Approximately 80% of the fusion protein material was eluted by the non-denaturing elution buffer (see FIG. 16, lanes 2 and 3). As judged by non-reducing SDS PAGE analysis 90% of the soluble fusion protein material (corresponding to approximately 70 mg of fusion protein) appeared monomeric (see FIG. 16, lane 2) yielding an overall efficiency of the folding procedure of approximately 70%.

Monomeric hGH fusion protein was purified from dimer and higher order multimers by ion exchange chromatography on Q-Sepharose (Pharmacia, Sweden): After gelfiltration into a buffer containing 25 mM NaCl and 25 mM Tris-HCl pH 8 on Sephadex G-25 the fusion protein material, eluted by the non-denaturing buffer, was applied onto a Q-Sepharose ion exchange column. Fusion protein was eluted over 5 column volumes with a linear gradient from 25 mM NaCl, 25 mM Tris-HCl pH 8 to 200 mM NaCl, 50 mM Tris-HCl pH 8. The monomeric hGH fusion protein eluted in the beginning of the gradient, whereas dimers and higher order multimers eluted latex. Fractions containing the pure monomeric fusion protein was added $NiSO_4$ and iminodiacetic acid (IDA, adjusted pH 8 with NaOH) to 1 mM and cleaved with the restriction protease $FX_a$ for 5 hours at 37° C. in a weight to weight ratio of approximately 100 to one. $FX_a$ was inhibited after cleavage by addition of Benzamidine hydrochloride to 1 mM.

After cleavage the recombinant hGH protein was isolated from uncleaved fusion protein and the liberated fusion tail, upon gelfiltration on Sephadex G-25 into 8 M Urea, 50 mM Tris-HCl pH 8, to remove $Ni^{2+}$IDA and Benzamidine, by passage through a small $Ni^{2+}$NTA-agarose column followed inline by a small $Nd^{3+}$NTA agarose column and subsequently a non $Ni^{2+}$activated NTA-agarose column to ensure complete removal of $FX_a$ and of $Ni^{2+}$ and $Nd^{3+}$, respectively. Recombinant hGH was purified from a minor fraction of recombinant breakdown product by ion exchange chromatography on Q-Sepharose: hGH was eluted in a linear gradient (over 5 column volumes) from 8 M Urea, 50 mM Tris HCl pH 8 to 8 M Urea, 250 mM NaCl, 25 mM Tris-HCl pH 8. Fractions containing the cleaved purified recombinant protein was gelfiltrated into freshly prepared 20 mM $NH_4HCO_3$ and lyophilized twice.

SDS-PAGE analysis of the production and folding of recombinant human growth hormone is presented in FIG. 16.

The yield of fully processed recombinant human growth hormone produced by this procedure was 10 mg.

The recombinant human growth hormone produced by this procedure co-migrated both in reducing and non-reducing SDS-PAGE and in non-denaturing PAGE analysis with biologically active recombinant human growth hormone generously provided by Novo-Nordisk A/S.

Example 3

Production and folding of human $\alpha_2$MRAP

The plasmid used for expression in *E. coli* BL21 cells of the human $\alpha_2$-Macroglobulin Receptor Associated Protein ($\alpha_2$MRAP), pT7H6FX-$\alpha_2$MRAP and the conditions used for production of the fusion protein has previously been described by us in Nykjar et al., J. Biol. Chem. 267: 14543–14546, 1992. The primers SEQ ID NO: 9 and SEQ ID NO: 10 were used in the PCR employed for multiplying the $\alpha_2$MRAP encoding DNA.

Crude protein extract precipitated from the phenol phase of the protein extraction of cells from 2 liters of culture of MGSHHHHHHCSIEGR-$\alpha_2$MRAP (wherein MGSHHHH-HHGSIEGR is SEQ ID NO: 48) expressing *E. coli* BL21 cells was dissolved in a buffer containing 6 M guanidinium chloride, 50 mM Tris-HCl pH 8 and 50 mM dithioerythriol. Following gel filtration on Sephadex G-25 (Pharmacia, Sweden) into 8 M Urea, 0.5 M NaCl, 50 mM Tris-HCl pH 8, and 1 mM methionine the crude protein preparation was applied to a $Ni^{2+}$activated NTA-agarose matrix ($Ni^{2+}$NTA-agarose) for purification (Hochuli et al., 1988) of the fusion protein, MGSHHHHHHGSIEGR-$\alpha_2$MRAP (wherein MGSHHHHHHGSIEGR is SEQ ID NO: 48) and subsequently to undergo the cyclic folding process.

All buffers prepared for liquid chromatography were degassed under vacuum prior to addition of reductant and/or use.

Preparation and "charging" of the $Ni^{2+}$NTA-agarose column is described under Example 1.

Upon application of the crude protein extract on the $Ni^{2+}$NTA-agarose column, the fusion protein, MGSHHHH-HHGSIEGR $\alpha_2$MRAP (wherein MGSHHHHHHGSIEGR is SEQ ID NO: 48) was purified from the majority of *E. coli* and λ phage proteins by washing with one column volume of the loading buffer followed by 6 M guanidinium chloride, 50 mM Tris-HCl, and 1 mM methionine until the optical density (OD) at 280 nm of the eluate was stable.

The fusion protein was refolded on the $Ni^{2+}$NTA-agarose column using a gradient manager profile as described in table 3 and 0.5 M NaCl, 50 mM Tris-HCl pH 8, 2 mM $CaCl_2$ and 1 mM 2-mercaptoethanol as buffer A and 6 M guanidinium chloride, 50 mM Tris-HCl pH 8, 2 mM $CaCl_2$ and 1 mM 2-mercaptoethanol as buffer B.

After completion of the cyclic folding procedure the $\alpha_2$MRAP fusion protein was eluted from the $Ni^{2+}$NTA agarose column with a buffer containing 0.5 M NaCl, 50 mM Tris-HCl, 20 mM EDTA pH 8.

Virtually no fusion protein was found to be aggregated or precipitated on the $Ni^{2+}$NTA-agarose column. The estimated yield of $\alpha_2$MRAP fusion protein was 60 mg and the efficiency of the folding procedure was close to 95%.

The fusion protein MGSHHHHHHGSIEGR-$\alpha_2$MRAP (wherein MGSHHHHHHGSIEGR is SEQ ID NO: 48) was cleaved with the bovine restriction protease $FX_a$ overnight at room temperature in a weight to weight ratio of 200:1 in the elution buffer. Upon gelfiltration on Sephadex G-25 into 100 mM NaCl, 25 mM Tris-HCl pH 8, the protein solution was passed through a $Ni^{2+}$NTA agarose column thereby removing uncleaved fusion protein and the liberated fusion N-terminal tail originating from cleaved fusion proteins. Finally the protein solution was diluted 1:4 with water and the $\alpha_2$MRAP protein purified from $FX_a$ by ion exchange chromatography on Q Sepharose (Pharmacia, Sweden). The Q-Sepharose column was eluted with a linear gradient over 6 column volumes from 25 mM NaCl, 25 mM Tris-HCl pH 8 to 250 mM NaCl, 25 mM Tris-HCl pH 8. The $\alpha_2$MRAP protein eluted in the very beginning of the linear gradient whereas $FX_a$ eluted later.

The yield of $\alpha_2$MRAP protein produced and refolded by this procedure was 40 mg.

The ligand binding characteristics (i.e. binding to the $\alpha_2$-Macroglobulin Receptor and interference with the binding of human Urokinase Plasminogen Activator—Plasminogen Activator inhibitor type-I complex to the $\alpha_a$-M Receptor) has, according to Dr. Nykjar, been found identical to the ligand binding characteristics of the purified natural protein.

Example 4

Production and folding of domains and domain-clusters from the $\alpha_2$-M Receptor The human $\alpha_2$-Macroglobulin Receptor/Low Density Lipoprotein Receptor-Related Protein ($\alpha_2$MR) is a 600 kDa endocytotic membrane receptor. $\alpha_2$-MR is synthesized as a 4524 amino acid single chain precursor protein. The precursor is processed into a 85 kDa transmembrane 62-chain and a 500 kDa $\alpha$-chain, non-covalently bound to the extracellular domain of the $\beta$-chain. The $\alpha_2$-MR is known to bind $Ca^{2+}$ in a structure dependent manner (i.e. the reduced protein does not bind $Ca^{2+}$) and is believed to the multifunctional in the sense that $\alpha_2$-MR binds ligands of different classes.

The entire amino acid sequence of the $\alpha$-chain can be represented by clusters of three types of repeats also found in other membrane bound receptors and in various plasma proteins:

- A: This type of repeat spans approximately 40 amino acid residues and is characterized by the sequential appearance of the six cysteinyl residues contained in the repeat. Some authors have named this repeat complement-type domain.
- B: This type of repeat also spans approximately 40 amino acid residues and is characterized by the sequential appearance of the six cysteinyl residues contained in the repeat. In the literature this repeat has been named EGF-type domains.
- C: This type of repeat spans approximately 55 amino acid residues and is characterised by the presence of the consensus sequence SEQ ID NO: 39.

This example describes the production in E. coli of a number of domains and domain-clusters derived from the $\alpha_2$-MR protein as $FX_a$ cleavable fusion proteins and the purification, in vitro folding, and the $FX_a$ cleavage and processing of these recombinant proteins.

A plasmid clone containing the full length cDNA encoding the human $\alpha_2$-MR protein (generously provided by Dr. Joachim Herz; Herz et al., EMBO J., 7: 4119–4127, 1988) was used as template in a series of Polymerase Chain Reactions (PCR) designed to produce cDNA fragments corresponding to a number of polypeptides representing domains and domain-clusters derived from the $\alpha_2$-MR protein:

- #1: Contains two domains of the A-type, corresponding to amino acid residues 20 to 109 in the $\alpha_2$-MR protein. The primers SEQ ID NO: 11 and SEQ ID NO: 12 were used in the PCR.
- #2: Contains two domains of the A-type followed by two type-B domains, corresponding to amino acid residues 20 to 190 in the $\alpha_2$-MR protein. The primers SEQ ID NO: 11 and SEQ ID NO: 13 were used in the PCR.
- #3: Identical to #2 followed by a region containing YWTD repeats, corresponding to amino acid residues 20 to 521. The primers SEQ ID NO: 11 and SEQ ID NO: 14 were used in the PCR.
- #4: Contains one type B domain, followed by 8 type-A domains and finally two type-B domains, corresponding to amino acid residues 803 to 1265 in the $\alpha_2$ MR protein. The primers SEQ ID NO: 15 and SEQ ID NO: 16 were used in the PCR.
- #5: Contains only the 8 type-A domains also present in #4, corresponding to amino acid residues 849 to 1184 in the $\alpha_2$-MR protein. The primers SEQ ID NO: 17 and SEQ ID NO: 18 were used in the PCR.
- #6: Contains the two C terminal type-B domains from #4, followed by 8 YWTD repeats and one type-B domain, corresponding to amino acid residues 1184 to 1502 in the $\alpha_2$-MR protein. The primers SEQ ID NO: 19 and SEQ ID NO: 20 were used in the PCR.
- #7: Contains the whole region included in constructs #4 to #6, corresponding to amino acid residues 803 to 1582 in the $\alpha_2$-MR protein. The primers SEQ ID NO: 15 and SEQ ID NO: 20 were used in the PCR.
- #8: Contains 10 type-A domains, corresponding to amino acid residues 2520 to 2941 in the $\alpha_2$-MR protein. The primers SEQ ID NO: 21 and SEQ ID NO: 22 were used in the PCR.
- #9: Contains 11 type-A domains, corresponding to amino acid residues 3331 to 3778 in the $\alpha_2$-MR protein. The primers SEQ ID NO: 23 and SEQ ID NO: 24 were used in the PCR.

The amplified nucleotide sequences encoding the domains and domain-clusters were at their 5'-end, via the PCR-reaction, linked to nucleotide sequences (included in SEQ ID NO: 11, 15, 17, 19, 21 and 23) encoding the amino acid sequence SEQ ID NO: 37 which constitutes a cleavage site for the bovine restriction protease $FX_a$ (Nagai and Thøgersen, Methods in Enzymology, 152: 461–481, 1987). The amplified DNA fragments were either subcloned into the E. coli expression vector $pT_7H_6$ (Christensen et al., FEBS Letters. 295: 181–184, 1991) or the expression plasmid pLcIIMLCH$_6$, which is modified from pLcIIMLC (Nagai et al., Nature, 332: 284–286, 1988) by the insertion of an oligonucleotide encoding six histidinyl residues C-terminal of the myocin light chain fragment. The construction of the resulting plasmids $pT_7H_6FX$-#1 to #3 and pLcIIMLCH$_6$FX-#4 to #9 is outlined in FIGS. 6–8 and in FIG. 9 is shown the amino acid sequence of the expressed protein (SEQ ID NO: 52).

The domains and domain-clusters subcloned in the $pT_7H_6FX$ series were grown and expressed in E. coli BL21 cells in a medium scale (2 liter) as described by Studier, and Moffat, J. Mol. Biol., 189: 113–130, 1986. Exponentially growing cultures at 37° C. were at $OD_{600}$ 0.8 infected with bacteriophage λCE6 at a multiplicity of approximately 5. Cultures were grown at 37° C. for another three hours before cells were harvested by centrifugation. Cells were lysed by osmotic shock and sonification and total cellular protein extracted into phenol (adjusted to pH 8 with Trisma base).

The domain clusters subcloned in the pLcIIMLCH$_6$ series were grown and expressed in E. coli QY13 cells as described in Nagai and Thøgensen. Methods in Enzymology, 152: 461–481, 1987. Exponentially growing cultures (4 liter) at 30° C. were at $OD_{600}$ 1.0 transferred to 42° C. for 15 min. This heal shock induces synthesis of the fusion proteins. The cultures were further incubated at 37° C. for three to four hours before cells were harvested by centrifugation. Cells were lysed by osmotic shock and sonification and total cellular protein extracted into phenol (adjusted to pH 8 with Trisma base).

Crude protein was precipitated from the phenol phase by addition of 3.5 volumes of ethanol and centrifugation. The protein pellet was dissolved in a buffer containing 6 M guanidinium chloride, 50 mM Tris-HCl pH 8 and 0.1 M dithioerythriol. Following gel filtration on Sephadex G-25 (Pharmacia, Sweden) into 8 M Urea, 1 M NaCl, 50 mM Tris-HCl pH 8, 10 mM 2-mercaptoethanol and 2 mM methionine the crude protein preparations were applied to a $Ni^{2+}$ activated NTA-agarose columns for purification (Hochuli et al., 1988) of the fusion proteins and subsequently to undergo the cyclic folding procedure.

All buffers prepared for liquid chromatography were degassed under vacuum prior to addition of reductant, and/or use.

Preparation and "charging" of the $Ni^{2+}$NTA-agarose column is described under Example 1.

Upon application of the crude protein extracts on the $Ni^{2+}$NTA-agarose column, the fusion proteins were purified from the majority of *E. coli* and λ phage proteins by washing with one column volume of the loading buffer followed by 6 M guanidinium chloride, 50 mM Tris-HCl, 10 mM 2 mercaptoethanol, and 2 mM methionine until the optical density (OD) at 280 nm of the eluate was stable.

Each of the fusion proteins were refolded on the $Ni^{2+}$NTA-agarose column using a gradient manager profile as described in table 4 and 0.5 M NaCl, 50 mM Tris-HCl pH 8, 2 mM $CaCl_2$, 0.33 mM methionine, and 2.0 mM/0.2 mM reduced/oxidized glutathione as buffer A and 4 M urea, 0.5 M NaCl, 50 mM Tris-HCl pH 8, 2 mM $CaCl_2$, 2 mM methionine, and 3 mM reduced glutathione as buffer B. The reduced/oxidized glutathione solution was freshly prepared as a 100 times stock solution by addition of 9.9 M $H_2O_2$ to a stirred solution of 0.2 M reduced glutathione before addition to buffer A.

After completion of the cyclic folding procedure the fusion proteins representing domains and domain-clusters derived from the $\alpha_2$-MR protein were eluted from the $Ni^{2+}$NTA-agarose column with a buffer containing 0.5 M NaCl, 50 mM Tris-HCl, 5 mM EDTA pH 8. Fusion proteins that were aggregated and precipitated on the $Ni^{2+}$NTA-agarose column were eluted in buffer B.

Approximately 75% of the fusion protein material expressed from the plasmids $pT_7H_6FX$-#1 and #2, representing the N-terminal two and four cysteine-rich domains of the $\alpha_2$-MR protein were eluted from the $Ni^{2+}$NTA-agarose column by the non-denaturing buffer. The majority of this fusion protein material appeared as monomers as judged by non-reducing SDS-PAGE analysis. The yields of monomeric fusion protein #1 and #2 were estimated to be approximately 50 mg.

Approximately 50% of the fusion protein material expressed from all other expression plasmids representing domain-clusters derived from the $\alpha_2$-MR protein was eluted from the $Ni^{2+}$NTA-agarose column by the non denaturing buffer. Between 30% (fusion proteins #5 and #7) and 65% (fusion protein #4) of these fusion proteins appeared as monomers as judged by non-reducing SDS-PAGE analysis (see FIG. 17, lanes 9 and 10).

Each fusion protein eluted by the non-denaturing elution buffer was cleaved with the restriction protease $FX_a$ overnight at room temperature in an estimated weight to weight ratio of 100 to one.

Upon gelfiltration on Sephadex G-25 into 100 mM NaCl, 25 mM Tris-HCl pH 8, the protein solution was passed through a $Ni^{2+}$NTA-agarose column thereby removing uncleaved fusion protein and the liberated N-terminal fusion tail originating from the cleaved fusion proteins. $FX_a$ was removed from the solution by passing the recombinant protein solutions through a small column of SBTI-agarose (Soy Bean Trypsin Inhibitor immobilized on Sepharose CL-6B (Pharmacia, Sweden)).

SDS-PAGE analysis of the refolded, soluble fusion protein product #4 is presented in FIG. 17, lanes 9 and 10, showing reduced and unreduced samples, respectively. The mobility increase observed for the unreduced sample reflects the compactness of the polypeptide due to the presence of 33 disulphide bridges.

Each of the recombinant proteins was found to bind $Ca^{2+}$ in a structure dependent manner.

It was found by Dr. Søron Moestrup that a monoclonal antibody, A2MRα-5 derived from the natural human $\alpha_2$-MR, bound the recombinant proteins expressed by the constructs #4, #6, and #7 whereas a monospecific antibody, A2MRα-3 derived also from natural $\alpha_2$-MR, was found to bind the recombinant protein expressed by construct #8. The binding specificity of both antibodies is structure dependent (i.e. the antibodies neither react with reduced $\alpha_2$-MR nor with reduced recombinant protein)

Example 5

Production and folding of bovine coagulation Factor $X_a$ ($FX_a$)

This example describes the production in *E. coli* of one fragment derived from bovine $FX_a$ as a $FX_a$ cleavable fusion protein and the purification, in vitro folding, and the processing of the recombinant protein.

The cDNA encoding bovine FX was cloned by specific amplification in a Polymerase Chain Reaction (PCR) of the nucleotide sequences encoding bovine FX from amino acid residues $Ser_{82}$ to $Trp_{404}$ (SEQ ID NO: 2, residues 82–484) (FXΔγ, amino acid numbering relates to the full coding reading frame) using 1st strand oligo-dT primed cDNA synthesized from total bovine liver RNA as template. Primers used in the PCR were SEQ ID NO: 25 and SEQ ID NO: 26. RNA extraction and cDNA synthesis were performed using standard procedures.

The amplified reading frame encoding FXΔγ was at the 5'-end, via the PCR-reaction, linked to nucleotide sequences encoding the amino acid sequence SEQ ID NO: 37 which constitute a cleavage site for the bovine restriction protease $FX_a$ (Nagai, and Thøgersen. Methods in Enzymology, 152: 461–481, 1987). The amplified DNA fragments was cloned into the *E. coli* expression vector $pLcIIMLCH_6$, which is modified from pLcIIMLC (Nagai et al., Nature, 332: 284–286, 1988) by the insertion of an oligonucleotide encoding six histidinyl residues C-terminal of the myosin light chain fragment. The construction of the resulting plasmid $pLcIIMLCH_6FX$-FXΔγ is outlined in FIG. 10 and in FIG. 11 is shown the amino acid sequence of the expressed protein (SEQ ID NO: 53).

The $pLcIIMLCH_6$-FXΔγ plasmid was grown and expressed in *E. coli* QY13 cells as described in Nagai and Thøgersen (Methods in Enzymology, 152: 461–481, 1987). Exponentially growing cultures at 30° C. were at $OD_{600}$ 1.0 incubated at 42° C. for 15 min. This heat shock induces synthesis of the fusion proteins. The cultures are further incubated at 37° C. for three to four hours before cells are harvested by centrifugation. Cells were lysed by osmotic shock and sonification and total cellular protein extracted into phenol (adjusted to pH 8 with Trisma base).

Crude protein was precipitated from the phenol phase by addition of 2.5 volumes of ethanol and centrifugation. The protein pellet was dissolved in a buffer containing 6 M guanidinium chloride, 50 mM Tris-HCl pH 8 and 0.1 M dithioerythriol. Following gel filtration on Sephadex G-25 (Pharmacia, LKB, Sweden) into 8 Urea, 1 M NaCl, 50 mM Tris-HCl pH 8, 10 mM 2-mercaptoethanol the crude protein preparation was applied to a $Ni^{2+}$ activated NTA-agarose matrix for purification (Hochuli et al., 1988.) of the FXΔγ fusion protein and subsequently to undergo the cyclic folding procedure.

All buffers prepared for liquid chromatography were degassed under vacuum prior to addition of reductant and/or use.

Preparation and "charging" of the $Ni^{2+}$NTA-agarose column is described under Example 1.

Upon application of the crude protein extracts on the Ni$^{2+}$NTA-agarose column, the fusion proteins were purified from the majority of E. coli and λ phage proteins by washing with one column volume of the loading buffer followed by 6 M guanidinium chloride, 50 mM Tris-HCl, and 10 mM 2-mercaptoethanol until the optical density (OD) at 280 nm of the eluate was stable.

The fusion protein was refolded on the Ni$^{2+}$NTA-agarose column using a gradient manager profile as described in table 5 and 0.5 M NaCl, 50 mM Tris HCl pH 8, 2 mM CaCl$_2$, and 2.0 mM/0.2 mM reduced/oxidized glutathione as buffer A and 8 M urea, 0.5 M NaCl, 50 mM Tris-HCl pH 8, 2 mM CaCl$_2$, and 3 mM reduced glutathione as buffer B. The reduced/oxidized glutathione solution was freshly prepared as a 100 times stock solution by addition of 9.9 M H$_2$O$_2$ to a stirred solution of 0.2 M reduced glutathione before addition to buffer A.

After completion of the cyclic folding procedure the FXΔγ fusion protein was eluted from the Ni$^{2+}$NTA-agarose column with a buffer containing 0.5 M NaCl, 50 mM Tris-HCl, 5 mM EDTA pH 8. Fusion protein that was aggregated and precipitated on the Ni$^{2+}$NTA-agarose column was eluted in buffer B.

Approximately 33% of the FXΔγ fusion protein material was eluted from the Ni$^{2+}$NTA-agarose column by the non-denaturing buffer. The amount of FXΔγ fusion protein was estimated to 15 mg. Only about one third of this fusion protein material appeared as monomers as judged by non-reducing SDS-PAGE analysis corresponding to an overall efficiency of the folding procedure of approximately 10%.

FXΔγ fusion protein in non-denaturing buffer was activated by passing the recombinant protein solution through a small column of trypsin-agarose (trypsin immobilized on Sepharose CL-6B (Pharmacia, Sweden)).

The activated recombinant FXΔγ fusion protein was assayed for protcolytic activity and substrate specificity profile using standard procedures with chromogenic substrates. The activity and substrate specificity profile was indistinguishable from that obtained for natural bovine FX$_a$ Example 6

Production and folding of kringle domains 1 and 4 from human plasminogen

This example describes the production in E. coli of the lysine binding kringle domains 1 and 4 from human plasminogen (K1 and K4, respectively) as FX$_a$ cleavable fusion proteins and the purification and in vitro folding of the K1- and K4-fusion proteins.

A plasmid clone containing the full length cDNA encoding human plasminogen cloned into the general cloning vector pUC18 (generously provided by Dr. Earl Davis, Seattle, USA) was used as template in a Polymerase Chain Reaction (PCR) designed to produce cDNA fragments corresponding to K1 (corresponding to amino acid residues Ser$_{81}$ to Glu$_{162}$ in so-called Glu-plasminogen) and K4 (corresponding to amino acid residues Val$_{354}$ to Ala$_{439}$ in so-called Glu-plasminogen). The primers SEQ ID NO: 27 and SEQ ID NO: 28 were used in the PCR producing K1 and the primers SEQ ID NO: 29 and SEQ ID NO: 30 were used in the PCR producing K4. The amplified reading frames encoding K1 and K4 were at their 5'-ends, via the PCR-reaction, linked to nucleotide sequences, included in SEQ ID NO: 27 and SEQ ID NO: 29, encoding the amino acid sequence SEQ ID NO: 37 which constitutes a cleavage site for the bovine restriction protease FX$_a$ (Nagai and Thøgersen. Methods in Enzymology, 152: 461–481, 1987).

The amplified K1 DNA fragment was cloned into the E. coli expression vector pLcIIMLCH$_6$, which is modified from pLcIIMLC (Nagai et al., Nature, 332: 284–286, 1988) by the insertion of an oligonucleotide encoding six histidinyl residues C-terminal of the myosin light chain fragment. The construction of the resulting plasmid pLcIIMLCH$_6$FX-K1 is outlined in FIG. 12. The amplified K4 DNA fragment was cloned into the E. coli expression vector pLcIIH$_6$, which is modified from pLcII (Nagai and Thøgersen. Methods in Enzymology, 152: 461–481, 1987) by the insertion of an oligonucleotide encoding six histidinyl residues C-terminal of the cII fragment. The construction of the resulting plasmid pLcIIH$_6$FX-K4 is outlined in FIG. 13 and in FIG. 14 is shown the amino acid sequence of human "Glu" plasminogen (SEQ ID NO: 54).

Both the pLcIIMLCH$_6$-K1 plasmid and the pLcIIH$_6$FX-K4 plasmid were grown and expressed in E. coli QY13 cells as described in Nagai and Thøgersen. Methods in Enzymology, 152: 461–481, 1987. Exponentially growing cultures at 30° C. were at OD$_{600}$ 1.0 transferred to 42° C. for 15 min. This heat shock induced synthesis of the fusion proteins. The cultures were further incubated at 37° C. for three to four hours before cells were harvested by centrifugation. Cells were lysed by osmotic shock and sonification and total cellular protein extracted into phenol (adjusted to pH 8 with Trisma base).

Crude protein was precipitated from the phenol phase by addition of 2.5 volumes of ethanol and centrifugation. The protein pellet was dissolved in a buffer containing 6 M guanidinium chloride, 50 mM Tris-HCl pH 8 and 0.1 M dithioerythriol. Following gel filtration on Sephadex G-25 (Pharmacia, Sweden) into 8 M Urea, 1 M NaCl, 50 mM Tris-HCl pH 8, 10 mM 2-mercaptoethanol, and 2 mM methionine the crude protein preparation was applied to a Ni$^{2+}$ activated NTA—agarose matrix for purification (Hochuli et al., 1988.) of the K1- and K4-fusion proteins and subsequently to undergo the cyclic folding procedure.

All buffers prepared for liquid chromatography were degassed under vacuum prior to addition of reductant and/or use.

Preparation and "charging" of the Ni$^{2+}$NTA-agarose column is described under Example 1.

Upon application of the crude protein extracts on the Ni$^{2+}$NTA-agarose column, the fusion proteins were purified from the majority of E. coli and λ phage proteins by washing with one column volume of the loading buffer followed by 6 M guanidinium chloride, 50 mM Tris-HCl, 10 mM 2-mercaptoethanol, and 2 mM methionine until the optical density (OD) at 280 nm of the column eluate was stable.

The fusion protein was refolded on the Ni$^{2+}$NTA-agarose column using a gradient manager profile as described in table 4 with 0.5 M NaCl, 50 mM Trio-HCl pH 8, 10 mM 6 aminohexanoic acid (ε-aminocapronic acid, ε-ACA), 0.33 mM methionine, and 2.0 mM/0.2 mM reduced/oxidized glutathione as buffer A and 4 M Urea, 0.5 M NaCl, 50 mM Tris-HCl pH 8, 10 mM ε-ACA, 2 mM methionine, and 3 mM reduced glutathione as buffer B. The reduced/oxidized glutathione solution was freshly prepared as a 100 times stock solution by addition of 9.9 M H$_2$O$_2$ to a stirred solution of 0.2 M reduced glutathione before addition to buffer A.

After completion of the cyclic folding procedure each of the K1 and K4 fusion proteins were eluted from the Ni$^{2+}$ NTA-agarose column with a buffer containing 0.5 M NaCl, 50 mM Tris-HCl, 5 mM EDTA pH 8. Fusion proteins that were aggregated and precipitated on the Ni$^{2+}$NTA-agarose column were eluted in buffer B.

Virtually all of the K1- and K4-fusion protein material was eluted from the Ni$^{2+}$-agarose columns by the non-denaturing buffer. The estimated yields of K1-fusion protein and K4-fusion protein were approximately 60 mg. Virtually all of the K1-fusion protein as well as the K4-fusion protein appeared as monomers as judged by non-reducing SDS-PAGE analysis corresponding to an efficiency of the folding procedure above 90%.

SDS-PAGE analysis of the production of recombinant plasmin ogen kringles 1 and 4 is presented in FIG. 17.

The K1-fusion protein and the K4-fusion protein were further purified by affinity chromatography on lysine-Sepharose CL-6B (Pharmacia, Sweden). The fusion proteins were eluted from the affinity columns by a buffer containing 0.5 M NaCl, 50 mM Tris-HCl pH 8, 10 mM ε-ACA.

Binding to lysine-Sepharose is normally accepted as an indication of correct folding of lysine binding kringle domains.

The three dimensional structures of recombinant K1 and K4 protein domains, produced by this cyclic folding procedure and which have been fully processed by liberation from the N-terminal fusion tail and subsequently purified by ion exchange chromatography, have been confirmed by X-ray diffraction (performed by Dr. Robert Huber) and two dimensional NMR analysis (performed by stud. scient. Peter Reinholdt and Dr. Flemming Poulsen). The general yield of fully processed recombinant K1 and K4 protein domains by this procedure is 5 mg/liter culture.

Example 7

Production in *E. coli* and refolding of recombinant fragments derived from human α$_2$-Macroglubolin and chicken Ovostatin This example describes the production in *E. coli* of the receptor-binding domain of human α$_2$-Macroglobulin (α$_2$-MRBDv) as a FX$_a$ cleavable fusion protein, and the purification of the recombinant α$_2$-MRBDv after FX$_a$ cleavage.

The 462 bp DNA fragment encoding the α$_2$-Macroglobulin reading frame from amino acid residues Val$_{1299}$ to Ala$_{1451}$ (α$_2$-MRDv) was amplified in a Polymerase Chain Reaction (PCR), essentially following the protocol of Saiki et al., (1988). pA2M (generously provided by Dr. T. Kristensen) containing the full length cDNA of human α$_2$-Macroglobulin was used as template, and the oligonucleotides SEQ ID NO: 31 and SEQ ID NO: 32 as primers. The amplified coding reading frame was at the 5'-end, via the PCR-reaction, linked to a nucleotide sequence, included in SEQ ID NO: 7, encoding the amino acid sequence SEQ ID NO: 37 which constitute a cleavage site for the bovine restriction protease FX$_a$ (Nagai and Thøgersen, 1987). The amplified DNA fragment was subcloned into the *E. coli* expression vector pT$_7$H$_6$ (Christensen et al., 1991). The construction of the resulting plasmid pT$_7$H$_6$FX-α$_2$MRDv (expressing human α$_2$-MRDv) is outlined in FIG. 18 and the amino acid sequence of the expressed protein is shown in FIG. 19 (SEQ ID NO: 55).

Recombinant human α$_2$MRDv was produced by growing and expressing the plasmid pT$_7$H$_6$FX-α$_2$MRDv in *E. coli* BL21 cells in a medium scale (2×1 liter) as described by Studier and Moffat, J. Mol. Biol., 189: 113–130, 1986. Exponentially growing cultures at 37° C. were at OD$_{600}$ 0.8 infected with bacteriophage λCE6 at a multiplicity of approximately 5. Cultures were grown at 37° C. for another three hours before cells were harvested by centrifugation. Cells were lysed by osmotic shock and sonification and total cellular protein extracted into phenol (adjusted to pH 8 with Trisma base). Protein was precipitated from the phenol phase by addition of 2.5 volumes of ethanol and centrifugation. The protein pellet was dissolved in a buffer containing 6 M guanidinium chloride, 50 mM Tris-HCl pH 8 and 50 mM dithioerythriol. Following gel filtration on Sephadex G-25 (Pharmacia, LKB, Sweden) into 8 M Urea, 1 M NaCl, 50 mM Tris-HCl pH8, and 10 mM 2-mercaptoethanol the crude protein preparation was applied to a Ni$^{2+}$ activated NTA-agarose column (Ni$^{2+}$NTA-agarose) for purification (Hochuli et al., 1988) of the fusion protein, MGSHHHHHHGSIEGR-α$_2$MRDv (wherein MGSHHHH-HHGSIEGR is SEQ ID NO: 48) and subsequently to undergo the cyclic folding procedure.

Preparation and "charging" of the Ni$^{2+}$NTA-agarose column is described under Example 1.

All buffers prepared for liquid chromatography were degassed under vacuum prior to addition of reductant and/or use.

Upon application of the crude protein extract on the Ni$^{2+}$NTA-agarose column, the fusion protein, MGSHHHHHHGSIEGR-α$_2$MRDv (wherein MGSHHHH-HHGSIEGR is SEQ ID NO: 48) was purified from the majority of *E. coli* and λ phage proteins by washing with one column volume of the loading buffer followed by 6 M guanidinium chloride, 50 mM Tris-HCl, and 10 mM 2-mercaptoethanol, until the optical density (OD) at 280 nm of the eluate was stable.

The fusion protein was refolded on the Ni$^{2+}$NTA-agarose column using a gradient manager profile as described in table 4 and 0.5 M NaCl, 50 mM Tris-HCl pH 8, and 2.0 mM/0.2 mM reduced/oxidized glutathione as buffer A and 8 M urea 0.5 M NaCl, 50 mM Tris-HCl pH 8, and 5 mM reduced glutathione as buffer B. The reduced/oxidized glutathione solution was freshly prepared as a 200 times stock solution by addition of 9.9 M H$_2$O$_2$ to a stirred solution of 0.2 M reduced glutathione before addition to buffer A.

After completion of the cyclic folding procedure the α$_2$MRDv fusion protein was eluted from the Ni$^{2+}$NTA-agarose column with a buffer containing 0.5 M NaCl, 50 mM Tris-HCl, 20 mM EDTA pH 8. Fusion protein that was aggregated and precipitated on the Ni$^{2+}$NTA-agarose column was eluted in buffer B.

Approximately 50% of the fusion protein material was eluted in the aqueous elution buffer. Half of this fusion protein material appeared monomeric and folded as judged by non-reducing SDS-PAGE analysis.

Recombinant α$_2$MRDv protein was liberated from the N-terminal fusion tail by cleavage with the restriction protease FX$_a$ at room temperature in a weight to weight ratio of approximately 50 to one for four hours. After cleavage the α$_2$MRDv protein was isolated from uncleaved fusion protein, the liberated fusion tail, and FX$_a$, by gelfiltration on Sephadex G-25 into 10 mM NaCl, 50 mM Tris-HCl pH 8, followed by ion exchange chromatography on Q-Sepharose: α$_2$MRDv was eluted in a linear gradient (over 10 column volumes) from 10 mM NaCl, 10 mM Tris-HCl pH 8 to 500 mM NaCl, 10 mM Tris-HCl pH 8. The α$_2$MRDv protein eluted at 150 mM NaCl.

The recombinant α$_2$MRDv domain binds to the α$_2$M receptor with a similar affinity for the receptor as exhibited by the complete α$_2$-Macroglobulin molecule (referring to the estimated K$_D$ in one ligand-one receptor binding (Moestrup and Gliemann 1991)). Binding analysis was performed by Dr. Søren K. Moestrup and stud. scient. Kåre Lehmann).

Example 8

Production in *E. coli* and refolding of recombinant fragments derived from the trout virus VHS envelope glycoprotein G Expression and in vitro refolding of recombinant fragments derived from the envelope glycoprotein G from the trout virus VHS in *E. coli* as $FX_a$ cleavable fusion proteins was performed using general strategies and methods analogous to those outlined in the general description of the "cyclic refolding procedure" and given in Examples 1 and 6.

Example 9

Production in *E. coli* and refolding of recombinant human Tetranectin and recombinant fragments derived from human Tetranectin Tetranectin is a tetrameric protein consisting of four identical and non-covalently linked single chain subunits of 181 amino acid residues (17 kDa). Each subunit contains three disulphide bridges and binds $Ca^{2+}$. Tetranectin is found in plasma and associated with extracellular matrix. Tetranectin binds specifically to plasminogen kringle 4. This binding can specifically be titrated by lysine or ω-amino acids.

The cDNA encoding the reading frame corresponding to the mature tetranectin single chain subunit was cloned by specific amplification in a Polymerase Chain Reaction (PCR) (Saiki et al., 1988) of the nucleotide sequences from amino acid residue $Glu_1$ to $Val_{181}$ using $1s^t$ strand oligo-dT primed cDNA synthesized from total human placental RNA as template. Primers used in the PCR were SEQ ID NO: 33 and SEQ ID NO: 34. RNA extraction and cDNA synthesis were performed using standard procedures.

The amplified reading frame encoding the monomer subunit of tetranectin was at the 5'-end, via the PCR-reaction, linked to nucleotide sequences encoding the amino acid sequence SEQ ID NO: 37 which constitute a cleavage site for the bovine restriction protease $FX_a$ (Nagai, and Thøgersen, 1987). A glycine residue was, due to the specific design of the 5'-PCR primer (SEQ. ID NO. 33), inserted between the C-terminal arginine residue of the $FX_a$ cleavage site (SEQ ID NO. 37) and the tetranectin $Glu_1$-residue. The amplified DNA fragment was subcloned into the *E. coli* expression vector $pT_7H_6$ (Christensen et al., 1991). The construction of the resulting plasmid $pT_7H_6$FX-TETN (expressing the tetranectin monomer) is outlined in FIG. 20 and the amino acid sequence of the expressed protein is shown in FIG. 21 (SEQ ID NO: 56).

To prepare the tetranectin monomer, the plasmid $pT_7H_6$FX-TETN was grown in medium scale (4×1 liter; 2XTY medium, 5 mM $MgSO_4$ and 100 μg ampicillin) in *E. coli* BL21 cells, as described by Studier and Moffat, J. Mol. Biol., 189: 113–130, 1986. Exponentially growing cultures at 37° C. were at $OD_{600}$ 0.8 infected with bacteriophage λCE6 at a multiplicity of approximately 5. Cultures were grown at 37° C. for another three hours and the cells harvested by centrifugation. Cells were resuspended in 150 ml of 0.5 M NaCl, 10 mM Tris HCl pH 8, and 1 mM EDTA pH 8. Phenol (100 ml adjusted to pH 8) was added and the mixture sonicated to extract the total protein. Protein was precipitated from the phenol phase by 2.5 volumes of ethanol and centrifugation.

The protein pellet was dissolved in a buffer containing 6 M guanidinium chloride, 50 mM Tris-HCl pH 8 and 0.1 M dithioerythriol. Following gel filtration on Sephadex G-25 (Pharmacia, LKB, Sweden) into 8 M Urea, 1 M NaCl, 50 mM Tris-HCl pH 8 and 10 mM 2-mercaptoethanol, the crude protein preparation was applied to a $Ni^{2+}$ activated NTA-agarose column ($Ni^{2+}$NTA-agarose, 75 ml pre-washed with 8 M urea, 1 M NaCl, 50 mM Tris-HCl pH 8, and 10 mM 2-mercaptoethanol) for purification (Hochuli et al., 1988) of the fusion protein, MGSHHHHHHGSIEGR-TETN (wherein MGSHHHHHHGSIEGR is SEQ ID NO: 48).

Preparation and "charging" of the $Ni^{2+}$NTA-agarose column is described under example 1.

All buffers prepared for liquid chromatography were degassed under vacuum prior to addition of reductant and/or use.

The column was washed with 200 ml of 8 M urea, 1 M NaCl, 50 mM Tris-HCl pH 8, and 10 mM 2-mercaptoethanol (Buffer I) and 100 ml of 6 M guanidinium chloride, 50 mM Tris-HCl pH 8 and 10 mM 2-mercaptoethanol (Buffer II). The MGSHHHHHHGSIEGR-TETN fusion protein was eluted with Buffer II containing 10 mM EDTA pH 8 and the elute was gel filtered on Sephadex G25 using Buffer I as eluant.

The eluted protein was then refolded. The fusion protein MGSHHHHHHGSIEGR-TETN (wherein MGSHHHHHHGSIEGR is SEQ ID NO: 48) was mixed with 100 ml $Ni^{2+}$NTA-agarose. The resin containing bound protein was packed into a 5 cm diameter column and washed with Buffer I supplemented with $CaCl_2$ to 2 mM. The fusion protein was refolded on the $Ni^{2+}$NTA-agarose column at 11–12° C. using a gradient manager profile as described in table 4 and 0.5 M NaCl, 50 mM Tris-HCl pH8, 2 mM $CaCl_2$ and 2.0 mM/0.2 mM reduced/oxidized glutathione as buffer A and 8 M urea, 1 M NaCl, 50 mM Tris-HCl pH 8, 2 mM $CaCl_2$ and 3 mM reduced glutathione as buffer B. The reduced/oxidized glutathione solution was freshly prepared as a 200 times stock solution by addition of 9.9 M $H_2O_2$ to a stirred solution of 0.2 M reduced glutathione before addition to buffer A.

After completion of the cyclic folding procedure the tetranectin fusion protein was eluted from the $Ni^{2+}$NTA-agarose column with a buffer containing 0.5 M NaCl, 50 mM Tris-HCl, 25 mM EDTA pH 8. The tetranectin fusion protein was cleaved with $FX_2$ at 4° C. overnight in a molar ratio of 1:300. After $FX_a$ cleavage the protein sample was concentrated 10 fold by ultrafiltration on a YM10 membrane (Amicon). Recombinant tetranectin was, after ten times dilution of the protein sample with 2 mM $CaCl_2$, isolated by ion-exchange chromatography on Q-Sepharose (Pharmacia, Sweden) in a linear gradient over 10 column volumes from 10 mM Tris-HCl pH 8, 2 mM $CaCl_2$ to 10 mM Tris-HCl pH 8, 2 mM $CaCl_2$, and 0.5 M NaCl.

Recombinant tetranectin produced by this procedure was analyzed by Dr. Inge Clemmensen Rigshospitalet, Copenhagen. Dr. Clemmensen found that the recombinant tetranectin with respect to binding to plasminogen kringle 4 and expression of antigenic sites behaved identically to naturally isolated human tetranectin.

Preliminary experiments comparing the efficiency of refolding, using the "cyclic refolding procedure", of recombinant Tetranectin fusion protein bound to the $Ni^{2+}$NTA-agarose column versus recombinant Tetranectin contained in a dialysis bag indicate a significantly improved yield of soluble monomer from the solution refolding strategy. However, if either product of the cycling procedures is subjected to disulphide re-shuffling in solution in the presence of 5 mM $CaCl_2$ virtually all of the polypeptide material is converted to the correctly folded Tetranectin tetramer.

Denatured and reduced recombinant authentic Tetranectin contained in a dialysis bag, was refolded over 15 cyclic exposures to buffer B (6 M Urea, 100 mM Nacl, 50 mM Tris-HCl pH=8, 2 mM/0.2 mM reduced/oxidized glutathione, 2 mM $CaCl_2$ and 0.5 mM methionine) and buffer A (100 mM NaCl, 50 mM Tris-HCl pH 8, 2 mM/0.2 mM reduced/oxidized glutathione, 2 mM $CaCl_2$, and 0.5 mM methionine).

Example 10

Production and folding of a diabody expressed intracellularly in *E. coli*: Mab 32 diabody directed against tumour necrosis factor.

Diabodies (described in Holliger et al., 1993) are artificial bivalent and bispecific antibody fragments.

This example describes the production in E. coli of a diabody directed against tumour necrosis factor alpha (TNE-α), derived from the mouse monoclonal antibody Mab 32 (Rathjen et al., 1991, 1992; Australian Patent Appl. 7,576; EP-A-486,526).

A phagemid clone, pCANTAB5-myc-Mab32-5, containing Mab32 encoded in the diabody format (PCT/GB93/02492) was generously provided by Dr. G. Winter, Cambridge Antibody Technology (CAT) Ltd., Cambridge, UK. pCANTAB5-myc-Mab32-5 DNA was used as template in a Polymerase Chain Reaction (PCR) (Saiki et al., 1988), using the primers SEQ ID NO: 35 and SEQ ID NO: 36, designed to produce a cDNA fragment corresponding to the complete artificial diabody. The amplified coding reading frame was at the 5'-end, via the PCT-reaction, linked to a nucleotide sequence, included in SEQ ID NO: 35, encoding the amino acid sequence SEQ ID NO: 37 which constitutes a cleavage site for the bovine restriction protease $FX_a$ (Nagai and Thøgersen, 1987). The amplified DNA fragment was subcloned into the E. coli expression vector $pT_7H6$ (Christensen et al., 1991). The construction of the resulting plasmid $pT_7H_6FX$-DB32 (expressing the Mab32 diabody) is outlined in FIG. 22 and the amino acid sequence of the expressed protein is shown in FIG. 23 (SEQ ID NO: 57).

To prepare the diabody fragment, the plasmid $pT_7H_6FX$-DB32 was grown in medium scale (4×1 liter; 2×TY medium, 5 mM $MgSO_4$ and 100 μg ampicillin) in E. coli BL21 cells, as described by Studier and Moffat, J. Mol. Biol., 189: 113 130, 1986. Exponentially growing cultures at 37° C. were at $OD_{600}$ 0.8 infected with bacteriophage λCE6 at a multiplicity of approximately 5. Forty minutes after infection, rifampicin was added (0.2 g in 2 ml methanol per liter media). Cultures were grown at 37° C. for another three hours and the cells harvested by centrifugation. Cells were resuspended in 150 ml of 0.5 M NaCl, 10 mM Tris-HCl pH 8, and 1 mM EDTA pH 8. Phenol (100 ml adjusted to pH 8) was added and the mixture sonicated to extract the total protein. Protein was precipitated from the phenol phase by 2.5 volumes of ethanol and centrifugation.

The protein pellet was dissolved in a buffer containing 6 M guanidinium chloride, 50 mM Tris-HCl pH 8 and 0.1 M dithioerythriol. Following gel filtration on Sephadex G-25 (Pharmacia, LKB, Sweden) into 8 M Urea, 1 M NaCl, 50 mM Tris-HCl pH 8 and 10 mM 2-mercaptoethanol, the crude protein preparation was applied to a $Ni^{2+}$ activated NTA-agarose column ($Ni^{2+}$NTA-agarose, 75 ml pre-washed with 8 M urea, 1 M NaCl, 50 mM Tris-HCl pH 8, and 10 mM 2-mercaptoethanol) for purification (Hochuli et al., 1988) of the fusion protein, MGSHHHHHHGSIEGR-DB32 (wherein MGSHHHHHHGSIEGR is SEQ ID NO: 48).

Preparation and "charging" of the $Ni^{2+}$NTA-agarose column is described under example 1.

All buffers prepared for liquid chromatography were degassed under vacuum prior to addition of reductant and/or use.

The column was washed with 200 ml of 8 M urea, 1 M NaCl, 50 mM Tris-HCl pH 8, and 10 mM 2-mercaptoethanol (Buffer I) and 100 ml 6 M guanidinium chloride, 50 mM Tris HCl pH 8 and 10 mM 2-mercaptoethanol (Buffer II). The MGSHHHHHHGSIEGR-DB32 fusion protein was eluted with Buffer II containing 10 mM EDTA pH 8 and the elute was gel filtered on Sephadex G25 using Buffer I as eluant.

The protein eluted was then refolded. The fusion protein MGSHHHHHHGSIEGR-DB32 (wherein MGSHHHHH-HGSIEGR is SEQ ID NO: 48) was mixed with 100 ml $Ni^{2+}$NTA-agarose. The resin containing bound protein was packed into a 5 cm diameter column and washed with Buffer I. The fusion protein was refolded on the $Ni^{2+}$NTA-agarose column at 11–12° C. using a gradient manager profile as described in table 4 and 0.5 M NaCl, 50 mM Tris-HCl pH 8, and 2.0 mM/0.2 mM reduced/oxidized glutathione as buffer A and 8 M urea, 1 M NaCl, 50 mM Tris-HCl pH 8, and 3 mM reduced glutathione as buffer B. The reduced/oxidized glutathione solution was freshly prepared as a 200 times stock solution by addition of 9.9 M $H_2O_2$ to a stirred solution of 0.2 M reduced glutathione before addition to buffer A.

After completion of the cyclic folding procedure the DB32 fusion protein was eluted from the $Ni^{2+}$NTA-agarose column with a buffer containing 0.5 M NaCl, 50 mM Tris-HCl, 25 mM EDTA pH 8 and adjusted to 5 mM GSH, 0.5 mM GSSG and incubated for 12 to 15 hours at 20° C. The fusion protein was then concentrated 50 fold by ultrafiltration using YM10 membranes and clarified by centrifugation.

The DB32 fusion protein dimer was purified by gel filtration using a Superose 12 column (Pharmacia, Sweden) with PBS as eluant.

The overall yield of correctly folded DB32 fusion protein from this procedure was 4 mg per liter.

An analysis by non-reducing SDS-PAGE from different stages of the purification is shown in FIG. 26.

The MGSHHHHHHGSIEGR (SEQ ID NO: 48) N-terminal fusion peptide was cleaved off the DB32 protein by cleavage with the restriction protease $FX_a$ (molar ratio 1:5 $FX_a$:DB32 fusion protein) at 37° C. for 20 hours. This is shown as the appearance of a lower molecular weight band just below the uncleaved fusion protein in FIG. 26.

The refolded DB32 protein was analyzed by Cambridge Antibody Technology Ltd. (CAT). DB32 was found to bind specifically to TNF-α and to compete with the Mab32 whole antibody for binding to TNF-α. Furthermore both DB32 and Mab32 were competed in binding to TNF-α by sheep anti-301 antiserum, which had been raised by immunizing sheep with a peptide encoding the first 18 amino acids of human TNF-α and comprised at least part of the epitope recognised by the murine Mab32.

Example 11

Production and refolding of human psoriasin in E. coli.

Psoriasin is a single domain $Ca^{2+}$-binding protein of 100 amino acid residues (11.5 kDa). Psoriasin contains a single disulphide bridge. The protein which is believed to be a member of the S100 Protein family is highly up-regulated in psoriatic skin and in primary human keratinocytes undergoing abnormal differentiation.

The plasmid $pT_7H_6FX$-PS.4 (kindly provided by Dr. P. Madsen, Insitute of Medical Biochemistry, University of Aarhus, Denmark) has previously been described by Hoffman et al., (1994). The nucleotide sequence encoding the psoriasin protein from $Ser_2$ to $Gln_{101}$ is in the 5'-end linked to the nucleotide sequence encoding the amino acid sequence MGSHHHHHHGSIEGR (SEQ ID NO: 48). A map of $pT_7H_6FX$-PS.4 is given in FIG. 24 and the amino acid sequence of human psoriasin is listed in FIG. 25 (SEQ ID NO: 58).

Recombinant human psoriasin was grown and expressed from the plasmid $pT_7H_6FX$-PS.4 in E. coli BL21 cells and total cellular protein extracted as described (Hoffmann et al., 1994). Ethanol precipitated total protein was dissolved in a buffer containing 6 M guanidinium chloride, 50 mM Tris-HCl pH 8 and 50 mM dithioerythriol. Following gel filtration on Sephadex G-25 (Pharmacia, LKB, Sweden) into 8 M Urea, 0.5 M NaCl, 50 mM Tris-HCl pH 8 and 5 mM 2-mercaptoethanol the crude protein preparation was applied to a $Ni^{2+}$ activated NTA agarose column ($Ni^{2+}$NTA-agarose) for purification (Hochuli et al., 1988) of the fusion protein, MGSHHHHHHGSIEGR-psoriasin (wherein MGSHHHHHHGSIEGR is SEQ ID NO: 48) and subsequently to undergo the cyclic folding procedure.

Preparation and "charging" of the $Ni^{2+}$NTA-agarose column is described under Example 1.

All buffers prepared for liquid chromatography were degassed under vacuum prior to addition of reductant and/or use.

Upon application of the crude protein extract on the $Ni^{2+}$NTA-agarose column, the fusion protein, MGSHHHHHHGSIEGR-psoriasin (wherein MGSHHHH-HHGSIEGR is SEQ ID NO: 48) was purified from the majority of E. coli and λ phage proteins by washing with one column volume of the loading buffer followed by 6 M guanidinium chloride, 50 mM Tris-HCl, and 5 mM 2-mercaptoethanol until the optical density (OD) at 280 nm of the eluate was stable.

The fusion protein was refolded on the $Ni^{2+}$NTA-agarose column using a gradient manager profile as described in table 4 and 0.5 M NaCl, 50 mM Tris HCl pH 8, 2 mM $CaCl_2$ and 1.0 mm/0.1 mM reduced/oxidized glutathione as buffer A and 8 M urea, 0.5 M NaCl, 50 mM Tris-HCl pH 8, 2 mM $CaCl_2$ and 5 mM reduced glutathione as buffer B. The reduced/oxidized glutathione solution was freshly prepared as a 200 times stock solution by addition of 9.9 M $H_2O_2$ to a stirred solution of 0.2 M reduced glutathione before addition to buffer A.

After completion of the cyclic folding procedure was psoriasin fusion protein was eluted from the $Ni^{2+}$NTA-agarose column with a buffer containing 0.5 M NaCl, 50 mM Tris-HCl, 10 mM EDTA pH 8. Fusion protein that was aggregated and precipitated on the $Ni^{2+}$NTA-agarose column was eluted in buffer B.

Approximately 95% of the fusion protein material was eluted by the non-denaturing elution buffer. As judged by non-reducing SDS-PAGE analysis 75% of the soluble fusion protein material appeared to be monomeric yielding an overall efficiency of the folding procedure of approximately 70%. The efficiency of the previously described refolding procedure for reproduction of recombinant human psoriasin (Hoffman et al., 1994) was estimated to be less than 25%.

The psoriasin fusion protein was cleaved with $FX_a$ in a molar ratio of 100:1 for 48 hours at room temperature. After gelfiltration into a buffer containing 20 mM Na-acetate pH 5 and 20 mM NaCl on Sephadex G-25 the protein sample was applied onto a S-Sepharose ion exchange column (Pharmacia). Monomeric recombinant psoriasin was eluted over 5 column volumes with a linear gradient from 20 mM Na acetate pH 5, 20 mM NaCl to 0.5 M NaCl. Monomeric psoriasin eluted at 150 mM NaCl. Dimeric and higher order multimers of psoriasin together with uncleaved fusion protein eluted later in the gradient. Fractions containing the cleaved purified recombinant protein were gelfiltrated on Sephadex G25 into a buffer containing 150 mM NaCl, 10 mM Tris-HCl pH 7.4 and stored at 4° C.

Example 12

Evaluation procedure for suitability testing of thiol compounds for use as reducing agents in cyclic refolding and determination of optimal levels of denaturants and disulphide reshuffling agents for optimization of cyclic refolding procedures.

In order to improve the yield of correctly folded protein obtainable from cyclic refolding the number of productive cycles should be maximized (see SUMMARY OF THE INVENTION). Productive cycles are characterized by steps of denaturation where misfolded protein, en route to dead-end aggregate conformational states, is salvaged into unfolded conformational states while most of the already correctly folded protein remains in conformational states able to snap back into the refolded state during the refolding step of the cycle.

A number of disulphide bridge containing proteins, like $\beta_2$-microglobulin, are known to refold with high efficiency (>95%) when subjected to high levels of denaturing agents as long as their disulphide bridges remain intact.

This example describes how to evaluate suitability of a thiol compound for use in cyclic refolding on the basis of its ability to discriminate correct from incorrect disulphide bridges and how to optimize levels of denaturing agent and/or reducing agent to be used in the denaturation steps in order to maximize the number of productive cycles. As model systems we chose a mixture of mono, di- and multimeric forms of purified recombinant human $\beta_2$-microglobulin. Our specific aim was to analyze the stability of different topological forms of human $\beta_2$-microglobulin against reduction by five different reducing agents at various concentrations of denaturing agent.

Human $\beta_2$-microglobulin (produced as described in Example 13) in 6 M guanidinium chloride, 50 mM Tris-HCl and 10 mM 2-mercaptoethanol pH 8 was gelfiltrated into non-denaturing buffer (50 mM Tris-HCl), 0.5 M NaCl pH 8). Only a fraction of the protein in the sample was soluble in the non-denaturing buffer. After 48 hours exposure to air, the protein solution appeared unclear. Non-reducing SDS-PAGE analysis showed that most of the protein had been oxidized into multimeric forms and only a small fraction was oxidized and monomeric (FIG. 27, lane 1).

The protein solution was aliquoted into a number of tubes and varying amounts of urea added while keeping the concentration of protein and salt at a constant level.

Reducing agent, either glutathione, cysteine ethyl ester, N-acetyl-L-cysteine, mercaptosuccinic acid or 2-mercaptoethanol was added to the ensemble of protein samples with varying urea concentrations. Each reducing agents was added to a final concentration of 4 mM. The protein samples were incubated at room temperature for 10 min and then free thiol groups were blocked by addition of iodoacetic acid to a final concentration of 12 mM. Finally, the protein samples were analyzed by non-reducing SDS-PAGE (FIGS 27–30, 31, and data not shown). The compositions of the test-samples used in the non-reducing SDS-PAGE as well as the results are given below in the following tables; in the rows indicating the ability of the chosen reducing agent to reduce disulphide bridges the marking "+++" indicated good ability, "++" indicated intermediate ability, "+" indicates weak ability, whereas no marking indicates that no measurable effect could be observed.

Figure 27:
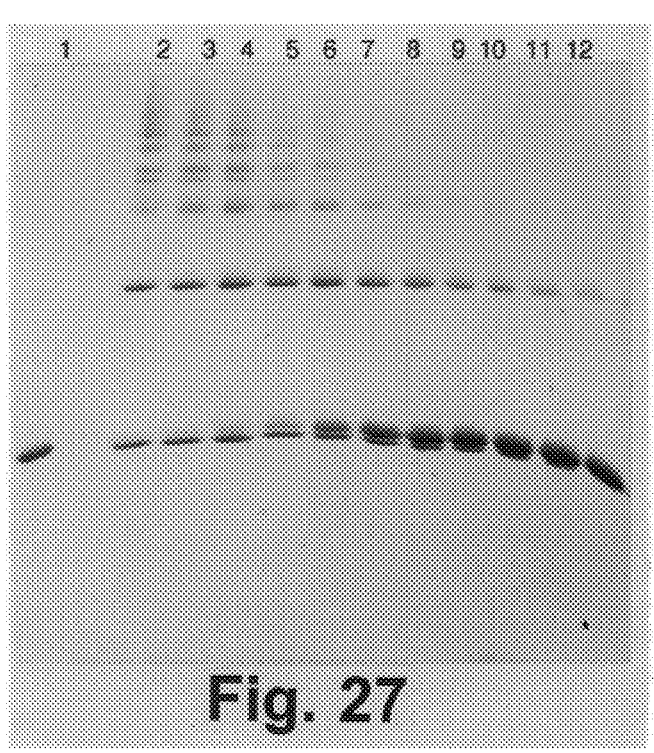

Composition of samples used in SDS-PAGE of FIG. 27

| Test no. | 1 | 2 | 3 | 4 | 5 | 6 | 7 | 8 | 9 | 10 | 11 |
|---|---|---|---|---|---|---|---|---|---|---|---|
| μl protein solution | 36 | 36 | 36 | 36 | 36 | 36 | 36 | 36 | 36 | 36 | 36 |
| μl Buffer A | 160 | 160 | 140 | 120 | 100 | 80 | 70 | 60 | 50 | 40 | 20 |
| μl Buffer B | 0 | 0 | 20 | 40 | 60 | 80 | 90 | 100 | 110 | 120 | 140 |
| μl GSH | 0 | 4 | 4 | 4 | 4 | 4 | 4 | 4 | 4 | 4 | 4 |
| M urea | 0 | 0 | 1 | 2 | 3 | 4 | 4.5 | 5 | 5.5 | 6 | 7 |
| Ability to reduce wrong disulphide bridges | | | I | I | II | II | III | III | III | III | III |
| Ability to reduce correct disulphide bridges | | | | | | | | | | + | +++ |

Buffer A: 50 mM Tris.HCl pH 8, 0.5 M NaCl
Buffer B: 10 M urea, 50 mM Tris.HCl pH 8, 0.5 M NaCl
GSH: 0.2 M Gluthatione
Protein solution: 2 mg/ml hβ$_2$m, 50 mM Tris.HCl pH 8, 0.5 M NaCl Composition of samples used in SDS-PAGE of FIG. 28

| Test no. | 1 | 2 | 3 | 4 | 5 | 6 | 7 | 8 | 9 |
|---|---|---|---|---|---|---|---|---|---|
| μl protein solution | 36 | 36 | 36 | 36 | 36 | 36 | 36 | 36 | 36 |
| μl Buffer A | 160 | 160 | 140 | 120 | 100 | 80 | 60 | 40 | 20 |
| μl Buffer B | 0 | 0 | 20 | 40 | 60 | 80 | 100 | 120 | 140 |
| μl CE | II | 4 | 4 | 4 | 4 | 4 | 4 | 4 | 4 |
| M urea | 0 | 0 | 1 | 2 | 3 | 4 | 5 | 6 | 7 |
| Ability to reduce wrong disulphide bridges | | ++ | ++ | ++ | +++ | +++ | +++ | +++ | +++ |
| Ability to reduce correct disulphide bridges | | | | | | | ++ | +++ | +++ |

Buffer A: 50 mM Tris.HCl pH 8, 0.5 M NaCl
Buffer B: 10 M urea, 50 mM Tris.HCl pH 8, 0.5 M NaCl
CE: 0.2 M L-cysteine ethyl ester
Protein solution: 2 mg/ml hβ$_2$m, 50 mM Tris.HCl pH 8, 0.5 M NaCl Composition of samples used in SDS-PAGE of FIG. 29

| Test no | 1 | 2 | 3 | 4 | 5 | 6 | 7 | 8 | 9 |
|---|---|---|---|---|---|---|---|---|---|
| μl protein solution | 36 | 36 | 36 | 36 | 36 | 36 | 36 | 36 | 36 |
| μl Buffer A | 160 | 160 | 140 | 120 | 100 | 80 | 60 | 40 | 20 |
| μl Buffer B | 0 | 0 | 20 | 40 | 60 | 80 | 100 | 120 | 140 |
| μl ME | 0 | 4 | 4 | 4 | 4 | 4 | 4 | 4 | 4 |
| M urea | 0 | 0 | 1 | 2 | 3 | 4 | 5 | 6 | 7 |
| Ability to reduce wrong disulphide bridges | | ++ | ++ | ++ | +++ | +++ | +++ | +++ | +++ |
| Ability to reduce correct disulphide bridges | | | | | | + | ++ | +++ | +++ |

Buffer A: 50 mM Tris.HCl pH 8, 0.5 M NaCl
Buffer B: 10 M urea, 50 mM Tris.HCl pH 8, 0.5 M NaCl
ME: 0.2 M 2-mercaptoethanol
Protein solution: 2 mg/ml hβ$_2$m, 50 mM Tris.HCl pH 8, 0.5 M NaCl Composition of samples used in SDS-PAGE of FIG. 30

| Test no. | 1 | 2 | 3 | 4 | 5 | 6 | 7 | 8 | 9 |
|---|---|---|---|---|---|---|---|---|---|
| μl protein solution | 36 | 36 | 36 | 36 | 36 | 36 | 36 | 36 | 36 |
| μl Buffer A | 160 | 160 | 140 | 120 | 100 | 80 | 60 | 40 | 20 |
| μl Buffer B | 0 | 0 | 20 | 40 | 60 | 80 | 100 | 120 | 140 |
| μl MSA | 0 | 4 | 4 | 4 | 4 | 4 | 4 | 4 | 4 |
| M urea | 0 | 0 | 1 | 2 | 3 | 4 | 5 | 6 | 7 |

-continued

Composition of samples used in SDS-PAGE of FIG. 30

| Test no. | 1 | 2 | 3 | 4 | 5 | 6 | 7 | 8 | 9 |
|---|---|---|---|---|---|---|---|---|---|
| Ability to reduce wrong disulphide bridges | | ++ | ++ | ++ | ++ | ++ | +++ | +++ | +++ |
| Ability to reduce correct disulphide bridges | | | | | | | ++ | +++ | +++ |

Buffer A: 50 mM Tris.HCl pH 8, 0.5 M NaCl
Buffer B: 10 M urea, 50 mM Tris.HCl pH 8, 0.5 M NaCl
MSA: 0.2 M Mercaptosuccinic acid
Protein solution: 2 mg/ml h$\beta_2$m, 50 mM Tris.HCl pH 8, 0.5 M NaCl Composition of samples used in SDS-PAGE of gel not shown

| Test no. | 1 | 2 | 3 | 4 | 5 | 6 | 7 | 8 | 9 |
|---|---|---|---|---|---|---|---|---|---|
| μl protein solution | 36 | 36 | 36 | 36 | 36 | 36 | 36 | 36 | 36 |
| μl Buffer A | 160 | 160 | 140 | 120 | 100 | 80 | 60 | 40 | 20 |
| μl Buffer B | 0 | 0 | 20 | 40 | 60 | 80 | 100 | 120 | 140 |
| μl AC | 0 | 4 | 4 | 4 | 4 | 4 | 4 | 4 | 4 |
| M urea | 0 | 0 | 1 | 2 | 3 | 4 | 5 | 6 | 7 |
| Ability to reduce wrong disulphide bridges | | + | ++ | ++ | +++ | +++ | +++ | +++ | +++ |
| Ability to reduce correct disulphide bridges | | | | | + | ++ | +++ | +++ | +++ |

Buffer A: 50 mM Tris.HCl pH 8, 0.5 M NaCl
Buffer B: 10 M urea, 50 mM Tris.HCl pH 8, 0.5 M NaCl
AC: 0.2 M N-acetyl-L-cysteine
Protein solution: 2 mg/ml h$\beta_2$m, 50 mM Tris.HCl pH 8, 0.5 M NaCl The different topological forms of $\beta_2$-m may be separated by non-reducing SDS-PAGE gel electrophoresis. The fastest migrating band represents the oxidized monomeric form. This band is immediately followed by the reduced $\beta_2$-m with a slightly slower migration rate, whereas the multimeric forms of the protein are migrating much slower in the gel.

In this analysis we are probing for the ability of each of the five reducing agents tested, to reduce the disulphide bridges of multimeric forms of $\beta_2$-microglobulin without significantly reducing the correctly formed disulphide bridge of the monomeric oxidized form.

The results from the analyses (FIGS. 27–30, 31, and data not shown) are, in summary, as follows: N-acetyl-L-cysteine and mercaptosuccinic acid are, under the conditions used, essentially unable to discriminate correct and incorrect disulphide bridges. Glutathione, cysteine ethyl ester and 2-mercaptoethanol are all capable of—within 10 min and within individual characteristic ranges of urea concentrations significantly reducing disulphide bridges of multimeric forms while most of the oxidised monomeric $\beta_2$-m remains in the oxidised form. Glutathione has clearly the capacity of selectively reducing incorrect disulphide bridges at higher concentrations of urea compared to cysteine ethyl ester and 2-mercaptoethanol and therefore glutathione among the selection of thiols tested would be the reducing agent of choice for cyclic refolding of human $\beta_2$-microglobulin. As a consequence of these experiments the concentration of urea in the reducing buffer B for the refolding procedure used in Example 13 was lowered from 8 M (Example 1) to 6 M, which led to an improvement of overall refolding yield of human $\beta_2$-microglobulin from 53% to 87%.

Example 13

Refolding of purified human $\beta_2$-microglobulin: Comparative analysis of three refolding procedures The following set of experiments were undertaken to obtain comparable quantitative data to evaluate the importance of cycling for refolding yield versus simple refolding procedures involving a stepwise or a gradual one-pass transition from strongly denaturing and reducing conditions to non-denaturing and non-reducing conditions.

Purified refolded recombinant human $\beta_2$-microglobulin fusion protein, obtained as described in EXAMPLE 1, was reduced and denatured to obtain starting materials devoid of impurities, such as proteolytic breakdown products or minor fractions of fusion protein damaged by irreversible oxidation or other chemical derivatization.

In a first step the optimization procedure described in EXAMPLE 12 was used to modify the conditions for cyclic refolding described in EXAMPLE 1 to increase the number of productive cycles. The optimized refolding protocol was identical to that described in EXAMPLE 1, as were buffers and other experimental parameters, except that the Buffer B in the present experiments was 6 M urea, 50 mM Tris-HCl pH 8, 0.5 M NaCl, 4 mM glutathione.

Three batches of pure fusion protein were refolded while attached to Ni$^{++}$-loaded NTA-agarose as described in EXAMPLE 1, using the present Buffer B composition. One batch was submitted to buffer cycling as described in EXAMPLE 1, for batch two and three cycling was replaced by a monotonous linear buffer gradient (100% B to 0% B over 24 hours) and a step gradient (100% B to 0% B in one step, followed by 0% B buffer for 24 hours), respectively. In each refolding experiment all of the polypeptide material was recovered as described in EXAMPLE 1 as a soluble fraction elutable under non-denaturing conditions and a remaining insoluble fraction elutable only under denaturing and reducing conditions. The yields of correctly folded fusion protein were then measured by quantitative densitometric analysis (Optical scanner HW and CS 370 Densitometric Analysis SW package from Hoeffer Scientific, Calif. USA) of Coomassie stained SDS-PAGE gels on which suitably diluted measured aliquots of soluble and insoluble fractions had been separated under reducing or non-reducing conditions, as required to allow separation of correctly disulphide-bridged monomer from soluble polymers in soluble fractions. Where required to obtain reliable densitometric data both for intense and faint bands in a gel lane several sample dilutions were scanned and analyzed to obtain re-scaled data sets.

Experimental details and results

Purified denatured and reduced fusion protein:

A batch of human $\beta_2$-microglobulin fusion protein was refolded as described in EXAMPLE 1. 96% of the fusion protein was recovered in the soluble fraction (FIG. 32, lanes 2–5). 56% of this soluble fraction was in the monomeric and disulphide-bridged form. Hence, the overall refolding efficiency obtained was 53%. Monomeric fusion protein was purified from multimers by ion exchange chromatography on S-Sepharose (Pharmacia, Sweden): The soluble fraction obtained after refolding was gel filtered on Sephadex G-25 (Pharmacia, Sweden) into a buffer containing 5 mM NaCl and 5 mM Tris-HCl pH 8, diluted to double volume with water and then applied to the S-Sepharose column, which was then eluted using a gradient (5 column volumes from 2.5 mM Tris-HCl pH 8, 2.5 mM NaCl to 25 mM Tris-HCl pH 8, 100 mM NaCl). The monomeric correctly folded fusion protein purified to >95% purity (FIG. 32, lanes 6 and 7) was then made 6 M in guanidinium hydrochloride and 0.1 M in DTE, gel filtrated into a buffer containing 8 M urea, 50 mM Tris-HCl pH 8, 1 M NaCl and 10 mM 2-mercaptoethanol and then divided into aliquots to be used as starting material for the refolding experiments described below.

Cyclic refolding or purified fusion protein:

An aliquot of denatured reduced fusion protein was applied to a $Ni^{++}$-loaded NTA column which was then washed with one column volume of a buffer containing 6 M guanidinium hydrochloride, 50 mM Tris-HCl pH 8 and 10 mM 2-mercaptoethanol.

The fusion protein was then subjected to buffer cycling according to the scheme shown in Table 1 using Buffer A: 50 mM Tris-HCl pH 8, 0.5 M NaCl and 3.2 mM/0.4 mM reduced/oxidized glutathione and Buffer B: 50 mM Tris-HCl pH 8, 0.5 M NaCl, 6 M urea and 4 mM reduced glutathione. After completion of buffer cycling the fusion protein was recovered quantitatively in a soluble form by elution of the column with a buffer containing 50 mM Tris-HCl pH 8, 0.5 M NaCl and 20 mM EDTA. 87% was obtained in the correct monomeric disulphide-bridged form (FIG. 32 lanes 8 and 9).

Refolding of purified fusion protein by linear gradient:

An aliquot of denatured reduced fusion protein was applied to a $Ni^{++}$-loaded NTA column which was then washed with one column volume of a buffer containing 6 M guanidinium hydrochloride, 50 mM Tris-HCl pH 8 and 10 mM 2-mercaptoethanol followed by 1 column volume of a buffer containing 50 mM Tris-HCl pH 8, 0.5 M NaCl, 6 M urea and 4 mM reduced glutathione.

A 24 hour linear gradient from 100% B to 100% A was then applied at 2 ml/min, using Buffer A: 50 mM Tris-HCl pH 8, 0.5 M NaCl and 3.2 mM/0.4 mM reduced/oxidized glutathione and Buffer B: 50 mM Tris-HCl pH 8, 0.5 M NaCl, 6 M urea and 4 mM reduced glutathione. After completion of the gradient the soluble fraction of fusion protein was eluted in a buffer containing 50 mM Tris-HCl pH 8, 0.5 M NaCl and 20 mM EDTA. The remaining insoluble fraction was extracted the column in a buffer containing 50 mM Tris-HCl pH 8, 1 M NaCl, 8 M urea, 10 mM 2-mercaptoethanol and 20 mM EDTA.

48% of the fusion protein was recovered in the soluble fraction and 60% of the soluble fraction was recovered in the correction monomeric disulphide-bridged form. The overall efficiency of folding obtained was therefore 29% (FIG. 33, lanes 5–7).

Refolding of purified fusion protein by buffer step:

An aliquot of denatured reduced fusion protein was applied to a $Ni^{++}$-loaded NTA column which was then washed with one column volume of a buffer containing 6 M guanidinium hydrochloride, 50 mM Tris-HCl pH 8 and 10 mM 2-mercaptoethanol.

Buffer containing 50 mM Tris-HCl pH 8, 0.5 M NaCl and 3.2 mM/0.4 mM reduced/oxidized glutathione was then applied to the column at 2 ml/min for 24 hours before recovering the soluble fraction of fusion protein in a buffer containing 50 mM Tris-HCl pH 8, 0.5 M NaCl and 20 mM EDTA. The remaining insoluble fraction was extracted from column in a buffer containing 50 mM Tris-HCl pH 8, 1 M NaCl, 8 M urea, 10 mM 2-mercaptoethanol and 20 mM EDTA.

34% of the fusion protein was recovered in the soluble fraction and 28% of the soluble fraction was recovered in the correction monomeric disulphide-bridged form. The overall efficiency of folding obtained was therefore 9.5% (FIG. 33, lanes 1–3).

Conclusions

In summary, using human $\beta_2$-microglobulin as a model protein, it may be concluded that (a) straightforward buffer optimization and improved purification of fusion protein prior to cyclic refolding increased refolding yield significantly (from 53% to 87%) and (b) progressive denaturation—renaturation cycling is superior to single-pass refolding under otherwise comparable experimental conditions by a very large factor (87% versus 29% or 9.5% yields).

REFERENCES:

Christensen, J. H., Hansen, P. K., Lillelund, O., and Thøgersen, H. C. (1991). Sequence-specific binding of the N-terminal three-finger fragment of Xenopus transcription factor IIIA to the internal control region of a 5S RNA gene. *FEBS Letters*, 295: 181–184.

Dalbøge, H., Dahl, H. -H., M., Pedersen, J., Hansen, J., W., and T., Kristensen (1987). A Novel Enzymatic Method for Production of Authentic hGH From an *Eschericia coli* Produced hGH-Precursor, *Bio/Technology*, 5: 161–164.

Datar, R., V., Cartwright, T., and C. -G. Rosen (1993). Process Economic of Animal Cell and Bacterial Fermentations: A Case Study Analysis of Tissue Plasminogen Activator. *Bio/Technology*, 11: 349–357.

Herz, J., Hanmann, U., Rogne, S., Myklebost, O., Gausepohl, H., and Stanley, K. K. (1988), Surface location and high affinity for calcium of a 500 kd liver membrane protein closely related to the LDL-receptor suggest a physiological role as lipoprotein receptor. *EMBO J.*, 7: 4119–4127.

Hoffmann, H. J., Olsen, E., Etzerodt, M., Madsen, P., Thøgersen, II. C., Kruse, T., and Celis J. E. (1994). Psoriasin Binds Calcium and Is Differentially Regulated With Respect to Other Members of the S100 Protein Family. *J. Dermatol. Invest.* in press.

Hochuli, E., W. Bannwarth, H. Döbeli, R. Gentz, and D. Stüber. 1988. Genetic approach to facilitate purification of recombinant proteins with a novel metal chelate absorbent. *Bio/Technology*, 6: 1321–1325.

Holliger., P., Prospero, T., and G. Winter (1993). "Diabodies": Small bivalent and bispecific antibody fragments. *Proc. Natl. Acad. Sci. USA*. 90: 6444–6448.

Maniatis, T., E. F. Fritsch, and J. Sambrook, 1982. *Molecular cloning.* Cold Spring Harbor Laboratory, Cold Spring Harbor, N.Y.

Nagai, K., and H. C. Thøgersen, 1987. Synthesis and Sequence-Specific Proteolysis of Hybrid Proteins Produced in *Escherichia coli. Methods in Enzymology,* 152: 461–481.

Nagai, K., Nakaseko, Y., Nasmyth, K., and Rhodes, D. (1988). Zinc-finger motifs expressed in *E. coli* and folded in vitro direct specific binding to DNA. *Nature,* 332: 284–286.

Nykjaer A., Petersen C. M., Møller B., Jensen P. H., Moestrup S. K., Holtet T. L., Etzerodt M., Thøgersen H. C., Munch M., Andreasen P. A., and Gliemann J. (1992). Purified $\alpha_2$-Macroglobulin Receptor/LDL Receptor-related Protein Binds Urokinase-Plasminogen Activator Inhibitor Type-I Complex. *J. Biol. Chem.* 267: 14543–14546.

Rathjen, D. et al. (1991), *Mol. Immunol.* 28, p29.

Rathjen, D. et al. (1992), *Brit. J. Cancer* 65, 852–856.

Saiki, R. K., Gelfant, D. H., Stoffel, S., Scharf, S. J., Higuchi, R., Horn, G. T., Mullis, K. B., and Erlich, H. A. (1988). Primer-directed enzymatic amplification of DNA with a thermostable DNA polymerase. *Science* 239: 487–491.

Studier, F. W. and Moffat, B. A. 1986. Use of Bacteriophage T7 RNA Polymerase to Direct Selective High level Expression of Cloned Genes. *J. Mol. Biol.,* 189: 113–130.

The regents of the University of California. Enterokinase-cleavable linker sequence. EP 035384.

---

What is claimed is:

1. A method for generating a processed ensemble of polypeptide molecules, in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformational states represented contain a substantial fraction of polypeptide molecules in unfolded or misfolded conformations, the method comprising subjecting the initial ensemble of polypeptide molecules to a series of at least five successive cycles, each of which comprises a sequence of 1) at least one denaturing step comprising conditions exerting a denaturing or unfolding influence on the polypeptide molecule of the ensemble so as to denature a fraction of the polypeptides in the ensemble, followed by 2) at least one renaturing step comprising conditions having a renaturing influence on the polypeptide molecules having conformations resulting from the preceding step so as to refold a fraction of the denatured or unfolded polypeptides in the ensemble, wherein:

A) the series of at least five successive cycles results in the processed ensemble of polypeptide molecules having a high fraction of polypeptide molecules in the particular folded conformation than
      a) the initial ensemble, and
      b) the corresponding processed ensemble which has been subjected to one of the cycles only and B) the polypeptide molecules are molecules which have an amino acid sequence identical to that of an authentic polypeptide, or are molecules which comprise an amino acid sequence corresponding to that of an authentic polypeptide joined to one or two additional polypeptide segments via a cleavable junction or similar or dissimilar cleavable junctions.

2. A method for generating a processed ensemble of polypeptide molecules, in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformational states represented contain a substantial fraction of polypeptide molecules in unfolded or misfolded conformations, the method comprising subjecting the initial ensemble of polypeptide molecules to a series of at least five successive cycles, each of which comprises a sequence of 1) at least one denaturing step comprising conditions exerting a denaturing or unfolding influence on the polypeptide molecules of the ensemble so as to denature a fraction of the polypeptides in the ensemble, followed by 2) at least one renaturing step comprising conditions having a renaturing influence on the polypeptide molecules having conformations resulting from the preceding step so as to refold a fraction of the denatured or unfolded polypeptides in the ensemble, wherein the polypeptide molecules are non-covalently adsorbed to a solid or semisolid carrier through a moiety having affinity to a component of the carrier, said polypeptide molecules being substantially confined to said carrier and in contact with an aqueous or an organic liquid phase during the denaturing step and the renaturing step, wherein the liquid can be changed or exchanged substantially without entraining the polypeptide molecules, wherein the series of at least five successive cycles results in the processed ensemble of polypeptide molecules having a higher fraction of polypeptide molecules in the particular folded conformation than
  a) the initial ensemble, and
  b) the corresponding processed ensemble which has been subjected to one of the cycles only.

3. A method according to claim 1, wherein the moiety has an amino acid sequence identical to SEQ ID NO: 47, the carrier comprising aa Nitrilotriacetic Acid derivative (NTA) charged with $Ni^{++}$ ions.

4. A method for generating a processed ensemble of polypeptide molecules, in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformational states represented contain a substantial fraction of polypeptide molecules in unfolded or misfolded conformations, the method comprising subjecting the initial ensemble of polypeptide molecules to a series of at least five successive cycles, each of which comprises a sequence of 1) at least one denaturing step comprising conditions exerting a denaturing or unfolding influence on the polypeptide molecule of the ensemble so as to denature a fraction of the polypeptides in the ensemble, followed by
2) at least one renaturing step comprising conditions having a renaturing influence on the polypeptide molecules having conformations resulting from the preceding step so as to refold a fraction of the denatured or unfolded polypeptides in the ensemble, wherein:
  A) the series of at least five successive cycles results in the processed ensemble of polypeptide molecules having a high fraction of polypeptide molecules in the particular folded conformation than
    a) the initial ensemble, and
    b) a corresponding processed ensemble which has been subjected to one of the cycles only and
  B) the polypeptide molecules comprise a polypeptide segment which is a substrate for preferential cleavage by a cleaving agent at a specific peptide bond, and said segment is a sequence which is selectively recognized by the bovine coagulation factor $X_a$.

5. A method for generating a processed ensemble of polypeptide molecules in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformational states represented contain a substantial fraction of polypeptide molecules in unfolded or misfolded conformations, the method comprising subjecting the initial ensemble of polypeptide molecules to a series of at least five successive cycles, each of which comprises a sequence of 1) at least one denaturing step comprising conditions exerting a denaturing or unfolding influence on the polypeptide molecule of the ensemble so as to denature a fraction of the polypeptides in the ensemble, followed by
2) at least one renaturing step comprising conditions having a renaturing influence on the polypeptide molecules having conformations resulting from the preceding step so as to refold a fraction of the denatured or unfolded polypeptides in the ensemble, wherein:
  A) the series of at least five successive cycles results in the processed ensemble of polypeptide molecules having a high fraction of polypeptide molecules in the particular folded conformation than
    a) the initial ensemble, and
    b) a corresponding processed ensemble which has been subjected to one of the cycles only and
  B) the polypeptide molecules comprise a polypeptide segment which is in vitro-convertible into a derivatized polypeptide segment which is a substrate for preferential cleavage by a cleaving agent at a specific peptide bond, the polypeptide segment being selectively recognized by the bovine coagulation factor $X_a$, and which polypeptide segment has an amino acid sequence selected from the group consisting of SEQ ID NO: 43, SEQ ID NO: 44, SEQ ID NO: 45, and SEQ ID NO: 46.

6. A method according to claim 5 wherein the polypeptide molecules comprise a polypeptide segment with either
  a) the amino acid sequence SEQ ID NO: 43 or SEQ ID NO: 44, which is converted into a derivatized polypeptide, which is selectively recognized by bovine coagulation factor $X_a$, by reacting the cysteine residue with N-(2-mercaptoethyl)morpholyl-2-thiopyridyl disulphide or mercaptothioacetate-2-thiopyridyl disulphide, or
  b) with the amino acid sequence SEQ ID NO: 45 or SEQ ID NO: 46, which is converted into a derivatized polypeptide, which is selectively recognized by bovine coagulation factor $X_a$ by oxidation of the thioether moiety in the methionine side group to a sulphoxide or sulphone derivative.

7. A method according to claim 4, wherein the polypeptide segment selected from the group consisting of SEQ ID NO: 38, SEQ ID NO: 40, SEQ ID NO: 41 and SEQ ID NO: 42 is linked N-terminally to the authentic polypeptide.

8. A method according to claim 4, wherein the polypeptide segment selected from the group consisting of SEQ ID NO: 43, SEQ ID NO: 44, SEQ ID NO: 45 and SEQ ID NO: 46 is linked N-terminally to the authentic polypeptide.

9. A method for generating a processed ensemble of polypeptide molecules in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformational states represented contain a substantial fraction of polypeptide molecules in unfolded or misfolded conformations, the method comprising subjecting the initial ensemble of polypeptide molecules to a series of at least five successive cycles, each of which comprises a sequence of 1) at least one denaturing step comprising conditions exerting a denaturing or unfolding influence on the polypeptide molecule of the ensemble so as to denature a fraction of the polypeptides in the ensemble, followed by 2) at least one renaturing step comprising conditions having a renaturing influence on the polypeptide molecules having conformations resulting from the preceding step so as to refold a fraction of the denatured or unfolded polypeptides in the ensemble, wherein:
A) the series of at least five successive cycles results in the processed ensemble of polypeptide molecules having a high fraction of polypeptide molecules in the particular folded conformation than
a) the initial ensemble, and
b) a corresponding initial ensemble which has been subjected to one of the cycles only;
B) the duration of each denaturing step is at least 1 millisecond and at most 1 hour, and the duration of each renaturing step is at least 1 second and at most 12 hours;
C) the denaturing conditions of each individual denaturing step are kept substantially constant for a period of time, and the renaturing conditions of each individual renaturing step are kept substantially constant for a period of time, the periods of time during which conditions are kept substantially constant being separated by transition periods during which the conditions are changed, the change of conditions being accomplished by changing the chemical composition of a liquid phase with which the polypeptide molecules are in contact; and
D) the denaturing of the polypeptide molecules is achieved or enhanced by decreasing or increasing pH of the liquid phase.

10. A method for generating a processed ensemble of polypeptide molecules in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformational states represented contain a substantial fraction of polypeptide molecules in unfolded or misfolded conformations, the method comprising subjecting the initial ensemble of polypeptide molecules to a series of at least five successive cycles, each of which comprises a sequence of
1) at least one denaturing step comprising conditions exerting a denaturing or unfolding influence on the polypeptide molecule of the ensemble so as to denature a fraction of the polypeptides in the ensemble, followed by
2) at least one renaturing step comprising conditions having a renaturing influence on the polypeptide molecules having conformations resulting from the preceding step so as to refold a fraction of the denatured or unfolded polypeptides in the ensemble, wherein:
A) the series of at least five successive cycles results in the processed ensemble of polypeptide molecules having a high fraction of polypeptide molecules in the particular folded conformation than
a) the initial ensemble, and
b) a corresponding initial ensemble which has been subjected to one of the cycles only;
B) the substantial fraction of polypeptide molecules in one particular folded conformation constitutes at least 5% (W/W) of the initial ensemble of polypeptide molecules;
C) the polypeptide molecules of the processed ensemble comprise cysteine-containing molecules, and the processed ensemble comprises a substantial fraction of polypeptide molecules in one particular uniform conformation which, in addition, have substantially identical disulphide bridging topology;
D) the polypeptide molecules are in contact with an aqueous or organic liquid phase during the denaturing step and the renaturing step, and wherein the liquid phase used in at least one of the denaturing steps and/or in at least one of the renaturing steps contains at least one disulphide-reshuffling system, X;
E) the disulphide-reshuffling system contains glutathione, 2-mercaptoethanol or thiocholine, each of which is in admixture with its corresponding symmetrical disulphide; and
F) the conversion of the cysteine residues to mixed disulphide products is accomplished by reacting the fully denatured and fully reduced ensemble of polypeptide molecules with an excess of a reagent which is a high-energy mixed disulphide compound.

11. A method according to claim 10, wherein the high-energy mixed disulphide compound is aliphatic-aromatic.

12. A method according to claim 10, wherein the high-energy mixed, disulphide compound has the general formula:

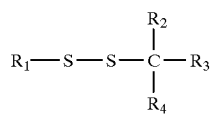

wherein $R_1$ is a pyridyl, $R_2$, $R_3$ and $R_4$ are hydrogen or an optionally substituted lower aromatic or aliphatic hydrocarbon group.

13. A method according to claim 11, wherein the high-energy mixed disulphide compound is selected from the group consisting of glutathionyl-2-thiopyridyl disulphide, 2-thiocholyl-2-thiopyridyl disulphide, 2-mercaptoethanol-2-thiopyridyl disulphide and mercaptoacetate-2-thiopyridyl disulphide.

14. A method according to claim 10, wherein
1) the chemical changes in the liquid phase are accomplished by changing between a denaturing solution B and a renaturing solution A and
2) the concentration of one or more denaturing compounds in B is decremented after each cycle.

15. A method for generating a processed ensemble of polypeptide molecules in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformational states represented contain a substantial fraction of polypeptide molecules in unfolded or misfolded conformations, the method comprising subjecting the initial ensemble of polypeptide molecules to a series of at least five successive cycles, each of which comprises a sequence of
1) at least one denaturing step comprising conditions exerting a denaturing or unfolding influence on the polypeptide molecule of the ensemble in the presence of a denaturing solution B so as to denature a fraction of the polypeptides in the ensemble, followed by
2) at least one renaturing step comprising conditions having a renaturing influence on the polypeptide molecules having conformations resulting from the preceding step so as to refold a fraction of the denatured or unfolded polypeptides in the ensemble, wherein:
  A) the series of at least five successive cycles results in the processed ensemble of polypeptide molecules having a high fraction of polypeptide molecules in the particular folded conformation than
    a) the initial ensemble, and
    b) a corresponding initial ensemble which has been subjected to one of the cycles only;
  B) the denaturing and renaturing of the polypeptide molecules is accomplished by direct changes in physical parameters to which the polypeptide molecules are exposed or by changes in physical parameters which enhance or moderate the denaturing and renaturing conditions; and
  C) the concentration of one or more denaturing compounds in denaturing solution B is kept constant in each cycle.

16. A method for generating a processed ensemble of polypeptide molecules in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformational states represented contain a substantial fraction of polypeptide molecules in unfolded or misfolded conformations, the method comprising subjecting the initial ensemble of polypeptide molecules to a series of at least five successive cycles, each of which comprises a sequence of
  1) at least one denaturing step comprising conditions exerting a denaturing or unfolding influence on the polypeptide molecules of the ensemble so as to denature a fraction of the polypeptides in the ensemble, followed by
  2) at least one renaturing step comprising conditions having a renaturing influence on the polypeptide molecules having conformations resulting from the preceding step so as to refold a fraction of the denatured or unfolded polypeptides in the ensemble, wherein:
    A) the series of at least five successive cycles results in the processed ensemble of polypeptide molecules having a high fraction of polypeptide molecules in the particular folded conformation than
      a) the initial ensemble, and
      b) a corresponding processed ensemble which has been subjected to one of the cycles only and
    B) the series comprises at least 10 and at most 1000 cycles.

17. A method according to claim 16, wherein the series comprises at least 25 cycles and at most 500 cycles.

18. A method according to claim 17, wherein the series comprises at most 200 cycles.

19. A method according to claim 18, wherein the series comprises at most 100 cycles.

20. A method according to claim 19, wherein the series comprises at most 50 cycles.

21. A method according to claim 2, wherein the moiety having affinity to a component of the carrier is a biotin group or an analogue thereof bound to an amino acid moiety of the polypeptide, the carrier having avidin, streptavidin, or analogues thereof attached thereto.

22. A method according to claim 4, wherein the polypeptide segment has an amino acid sequence selected from the group consisting of SEQ ID NO: 38, SEQ ID NO: 40, SEQ ID NO: 41 and SEQ ID NO: 42.

23. A method according to claim 8, wherein
  A) denaturing of the polypeptide molecules is accomplished by contacting the polypeptide molecules with a liquid phase in which at least one denaturing compound is dissolved, and wherein renaturing of the polypeptide molecules is accomplished by contacting the polypeptide molecules with a liquid phase which either contains at least one dissolved denaturing compound in such a concentration that the contact with the liquid phase will tend to renature rather than denature the ensemble of polypeptide molecules in their respective conformational states resulting from the preceding step, or contains no denaturing compound and
  B) the denaturing compound is selected from the group consisting of urea, guanidine-HCl, dimethylformamide and di-$C_{1-6}$-alkylsulphone.

24. A method for generating a processed ensemble of polypeptide molecules, in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformational states represented contain a substantial fraction of polypeptide molecules in unfolded or misfolded conformations, the method comprising subjecting the initial ensemble of polypeptide molecules to a series of at least five successive cycles, each of which comprises a sequence of
  1) at least one denaturing step comprising conditions exerting a denaturing or unfolding influence on the polypeptide molecules of the ensemble so as to denature a fraction of the polypeptides in the ensemble, followed by
  2) at least one renaturing step comprising conditions having a renaturing influence on the polypeptide molecules having conformations resulting from the preceding step so as to refold a fraction of the denatured or unfolded polypeptides in the ensemble, wherein:
    A) the series of at least five successive cycles results in the processed ensemble of polypeptide molecules having a higher fraction of polypeptide molecules in the particular folded conformation than
      a) the initial ensemble, and
      b) a corresponding initial ensemble which has been subjected to one of the cycles only;
    B) the polypeptide molecules are in contact with an aqueous or an organic liquid phase during the denaturing step and the renaturing step; and
    C) the polarity of the liquid phase used in the renaturing of the polypeptide molecules has been modified by the addition of a salt, a polymer, trifluoroethanol or a combination thereof.

* * * * *